United States Patent
Gielen-Haertwig et al.

(10) Patent No.: US 7,230,017 B2
(45) Date of Patent: Jun. 12, 2007

(54) DIHYDROPYRIDINONE DERIVATIVES

(75) Inventors: Heike Gielen-Haertwig, Monheim (DE); Volkhart Min-Jian Li, Velbert (DE); Ulrich Rosentreter, Wuppertal (DE); Karl-Heinz Schlemmer, Wuppertal (DE); Swen Allerheiligen, Essen (DE); Leila Telan, Wuppertal (DE); Lars Bärfacker, Oberhausen (DE); Jörg Keldenich, Wuppertal (DE); Mary F. Fitzgerald, Oxford (GB); Kevin Nash, Herts (GB); Barbara Albrecht, Wülfrath (DE); Dirk Meurer, Pulheim (DE)

(73) Assignee: Bayer Healthcare AG, Leverkusen (DE)

( * ) Notice: Subject to any disclaimer, the term of this patent is extended or adjusted under 35 U.S.C. 154(b) by 50 days.

(21) Appl. No.: 10/525,608

(22) PCT Filed: Aug. 18, 2003

(86) PCT No.: PCT/EP03/09108

§ 371 (c)(1),
(2), (4) Date: Oct. 13, 2005

(87) PCT Pub. No.: WO2004/020410

PCT Pub. Date: Mar. 11, 2004

(65) Prior Publication Data

US 2006/0100207 A1    May 11, 2006

(30) Foreign Application Priority Data

Aug. 27, 2002 (GB) ................. 0219894.3
Sep. 12, 2002 (GB) ................. 0221143.1

(51) Int. Cl.
| | | |
|---|---|---|
| A61K 31/4412 | (2006.01) | |
| A61K 31/444 | (2006.01) | |
| A61K 31/5377 | (2006.01) | |
| A61K 31/4439 | (2006.01) | |
| A61K 31/4436 | (2006.01) | |
| A61K 31/496 | (2006.01) | |
| A61K 31/4545 | (2006.01) | |
| C07D 401/02 | (2006.01) | |
| C07D 413/02 | (2006.01) | |
| C07D 211/86 | (2006.01) | |
| C07D 213/22 | (2006.01) | |
| C07D 417/02 | (2006.01) | |

(52) U.S. Cl. ............. 514/350; 514/351; 514/343; 514/342; 514/334; 514/318; 514/253.12; 514/237.2; 514/235.5; 544/131; 546/299; 546/298; 546/257; 546/279.1; 546/269.7; 546/194

(58) Field of Classification Search ............ 514/350, 514/351, 343, 342, 334, 318, 253.12, 237.2, 514/235.5; 544/131; 546/299, 298, 257, 546/279.1, 269.7, 194
See application file for complete search history.

(56) References Cited

U.S. PATENT DOCUMENTS 3,925,395 A    12/1975    Bayer ................. 206/294.8

FOREIGN PATENT DOCUMENTS

WO    02 053541    11/2002

OTHER PUBLICATIONS

Palomo et al. (J. Org. Chem. 1991, 56, 4418-4428).*
Walker et al. (CMLS, Cell. Mol. Life Sci. 58 (2001) 596-624.*
Abbenante et al (Medicinal Chemistry, 2005, 1, 71-104.*
Abstract of Chughtai et al. (Journal of Aerosol Medicine, 2004, 17(4), 289-298).*

* cited by examiner

*Primary Examiner*—Joseph K. McKane
*Assistant Examiner*—Jason M. Nolan

(57) ABSTRACT

The invention relates to novel dihydropyridinone derivatives, processes for their preparation, and their use in medicaments, especially for the treatment of chronic obstructive pulmonary diseases, acute coronary syndrome, acute myocardial infarction and heart failure development.

17 Claims, No Drawings

DIHYDROPYRIDINONE DERIVATIVES

The present invention relates to novel dihydropyridinone derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HNE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49–S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., *Inhibition of elastase improves myocardial function after repetitive ischaemia and myocardial infarction in the rat heart*, Eur. J. Physiol. 433, S563–S570 (1997); Dinerman et al, *Increased neutrophil elastase release in unstable angina pectoris and acute myocardial infarction*, J. Am. Coll. Cardiol. 15, 1559–1563 (1990)], of the development of heart failure [S. J. Gilbert et al., *Increased expression of promatrix metalloproteinase-9 and neutrophil elastase in canine dilated cardiomyopathy*, Cardiov. Res. 34, S377–S383 (1997)] and of atherosclerosis [Dollery et al., *Neutrophil elastase in human atherosclerotic plaque*, Circulation 107, 2829–2836 (2003)].

Ethyl 6-amino-1,4-bis(4-chlorophenyl)-5-cyano-2-methyl-1,4-dihydro-3-pyridinecarboxylate has been synthesized and tested for potential antimicrobial activity as described in A. W. Erian et al., *Pharmazie* 53 (11), 748–751 (1998).

The present invention relates to compounds of the general formula (I)

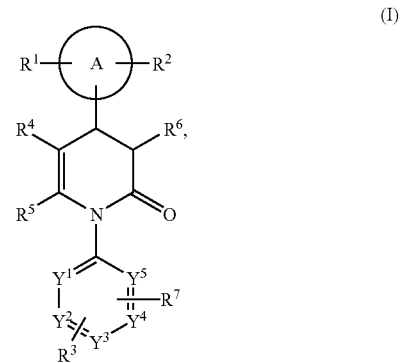

wherein

A represents an aryl or heteroaryl ring, $R^1$, $R^2$ and $R^3$ independently from each other represent hydrogen, halogen, nitro, cyano, trifluoromethyl, $C_1$–$C_6$-alkyl, hydroxy, $C_1$–$C_6$-alkoxy or trifluoromethoxy, wherein $C_1$–$C_6$-alkyl and $C_1$–$C_6$-alkoxy can be further substituted with one to three identical or different radicals selected from the group consisting of hydroxy and $C_1$–$C_4$-alkoxy, $R^4$ represents $C_1$–$C_6$-alkylcarbonyl, $C_1$–$C_6$-alkoxycarbonyl, $C_2$–$C_6$-alkenoxycarbonyl, hydroxycarbonyl, aminocarbonyl, mono- or di-$C_1$–$C_6$-alkylaminocarbonyl, $C_3$–$C_8$-cycloalkylaminocarbonyl, N-(heterocyclyl)-aminocarbonyl or cyano, wherein $C_1$–$C_6$-alkylcarbonyl, $C_1$–$C_6$-alkoxycarbonyl, mono- and di-$C_1$–$C_6$-alkylaminocarbonyl can be substituted with one to three identical or different radicals selected from the group consisting of hydroxy, $C_1$–$C_4$-alkoxy, hydroxycarbonyl, $C_1$–$C_4$-alkoxycarbonyl, amino, mono- and di-$C_1$–$C_4$-alkylamino, aminocarbonyl, mono- and di-$C_1$–$C_4$-alkylaminocarbonyl, $C_1$–$C_4$-alkylcarbonylamino, phenyl, heteroaryl and heterocyclyl, and wherein phenyl can be further substituted with halogen and wherein N-(heterocyclyl)-aminocarbonyl can be further substituted with $C_1$–$C_4$-alkyl or benzyl, $R^5$ represents $C_1$–$C_4$-alkyl, $R^6$ represents hydrogen, cyano, aminocarbonyl, mono- or di-$C_1$–$C_6$-alkylaminocarbonyl, $C_3$–$C_8$-cycloalkylaminocarbonyl, arylaminocarbonyl, N-aryl-N-$C_1$–$C_6$-alkylaminocarbonyl, $C_1$–$C_6$-alkylcarbonyl, $C_3$–$C_8$-cycloalkylcarbonyl, arylcarbonyl, hydroxycarbonyl, $C_1$–$C_6$-alkoxycarbonyl, $C_2$–$C_6$-alkenoxycarbonyl or aryloxycarbonyl, wherein mono- and di-$C_1$–$C_6$-alkylaminocarbonyl, arylaminocarbonyl, $C_1$–$C_6$-alkylcarbonyl and $C_1$–$C_6$-alkoxycarbonyl can be substituted with one to three identical or different radicals selected from the group consisting of halogen, hydroxy, $C_1$–$C_4$-alkoxy, benzyloxy, tri-($C_1$–$C_6$-alkyl)-silyloxy, $C_1$–$C_4$-alkylsulfonyloxy, hydroxycarbonyl, $C_1$–$C_4$-alkoxycarbonyl, amino, mono- and di-$C_1$–$C_4$-alkylamino, aminocarbonyl, mono- and di-$C_1$–$C_4$-alkylaminocarbonyl, $C_3$–$C_6$-cycloalkylaminocarbonyl, heterocyclylcarbonyl, $C_1$–$C_4$-alkylcarbonylamino, phenyl, heteroaryl and heterocyclyl, and wherein mono- and di-$C_1$–$C_4$-alkylaminocarbonyl can be further substituted with hydroxy or $C_1$–$C_4$-alkoxy, or
R$^6$ represents a moiety of the formula

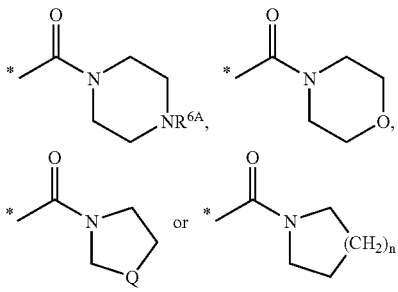

wherein R$^{6A}$ is selected from the group consisting of hydrogen, C$_1$–C$_6$-alkyl and C$_1$–C$_4$-alkylcarbonyl, Q represents O or S, and n represents an integer of 1 or 2,
or
R$^6$ represents a moiety of the formula

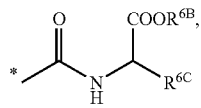

wherein R$^{6B}$ is selected from the group consisting of hydrogen and C$_1$–C$_6$-alkyl, and R$^{6C}$ is an amino acid side chain, R$^7$ represents hydrogen, halogen, nitro, cyano, trifluoromethyl, C$_1$–C$_6$-alkyl, hydroxy, C$_1$–C$_6$-alkoxy or trifluoromethoxy, wherein C$_1$–C$_6$-alkyl and C$_1$–C$_6$-alkoxy can be further substituted with one to three identical or different radicals selected from the group consisting of hydroxy and C$_1$–C$_4$-alkoxy, and
Y$^1$, Y$^2$, Y$^3$, Y$^4$ and Y$^5$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylamino, alkoxycarbonyl and alkoxycarbonylamino.

Alkoxy illustratively and preferably represents methoxy, ethoxy, n-propoxy, iso-propoxy, tert.-butoxy, n-pentoxy and n-hexoxy.

Alkenoxy illustratively and preferably represents allyloxy, but-2-en-1-oxy, pent-3-en-1-oxy und hex-2-en-1-oxy.

Alkylcarbonyl in general represents a straight-chain or branched hydrocarbon radical having 1 to 6, preferably 1 to 4 carbon atoms which has a carbonyl function at the position of attachment. Non-limiting examples include formyl, acetyl, n-propionyl, n-butyryl, isobutyryl, pivaloyl, n-hexanoyl.

Alkylcarbonylamino in general represents a straight-chain or branched hydrocarbon radical having 1 to 6, preferably 1 to 4 carbon atoms which has a carbonylamino (—CO—NH—) function at the position of attachment and which is bonded to the carbonyl group. Non-limiting examples include formylamino, acetylamino, n-propionylamino, n-butyrylamino, isobutyrylamino, pivaloylamino, n-hexanoylamino.

Alkoxycarbonyl illustratively and preferably represents methoxycarbonyl, ethoxycarbonyl, n-propoxycarbonyl, isopropoxycarbonyl, tert.-butoxycarbonyl, n-pentoxycarbonyl and n-hexoxycarbonyl.

Alkenoxycarbonyl illustratively and preferably represents allyloxycarbonyl, but-2-en-1-oxycarbonyl, pent-3-en-1-oxycarbonyl und hex-2-en-1-oxycarbonyl.

Alkylamino represents an alkylamino radical having one or two (independently selected) alkyl substituents, illustratively and preferably representing methylamino, ethylamino, n-propylamino, isopropylamino, tert.-butylamino, n-pentylamino, n-hexyl-amino, N,N-diethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert.-butyl-N-methylaminocarbonyl, N-ethyl-N-n-pentylamino-carbonyl and N-n-hexyl-N-methylaminocarbonyl.

Alkylsulfonyloxy in general represents a straight-chain or branched hydrocarbon radical having 1 to 4, preferably 1 to 3 carbon atoms which has a sulfonyloxy (—SO$_2$—O—) function at the position of attachment and which is bonded to the sulfonyl group. Non-limiting examples include methylsulfonyloxy, ethylsulfonyloxy, n-propylsulfonyloxy, isopropylsulfonyloxy, n-butylsulfonyloxy, tert.-butylsulfonyloxy.

Cycloalkyl in general represents a cyclic saturated hydrocarbon radical having 3 to 8, preferably 3 to 6 carbon atoms. Non-limiting examples include cyclopropyl, cyclobutyl, cyclopentyl, cyclohexyl and cycloheptyl.

Cycloalkylaminocarbonyl represents a cycloalkylaminocarbonyl radical having one or two (independently selected) cycloalkyl substituents with 3 to 8, preferably 4 to 6 ring carbon atoms which is bound via a carbonyl group, illustratively and preferably representing cyclopropylaminocarbonyl, cyclobutylaminocarbonyl, cyclopentylaminocarbonyl, cyclohexylaminocarbonyl and cycloheptylaminocarbonyl.

Aryl per se and in arylcarbonyl, aryloxycarbonyl or arylaminocarbonyl represents a mono- to tricyclic aromatic carbocyclic radical having generally 6 to 14 carbon atoms, illustratively and preferably representing phenyl, naphthyl and phenanthrenyl.

Arylcarbonyl illustratively and preferably represents benzoyl and naphthoyl.

Aryloxycarbonyl illustratively and preferably represents phenoxycarbonyl and naphthoxycarbonyl.

Arylaminocarbonyl illustratively and preferably represents phenylaminocarbonyl and naphthylaminocarbonyl.

Heteroaryl represents an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 heteroatoms and/or hetero groups selected from the group consisting of N, O, S, SO and SO$_2$. The heterocyclyl radicals can be saturated or partially unsaturated. Preference is given to 5- to 8-membered monocyclic saturated heterocyclyl radicals having up to two heteroatoms selected from the group consisting of O, N and S, such as illustratively and preferably tetrahydrofuran-2-yl, pyrrolin-1-yl, pyrrolidin-2-yl, pyrrolidin-3-yl, pyrrolinyl, piperidinyl, morpholinyl, thiomorpholinyl, perhydroazepinyl.

Heterocyclylcarbonyl illustratively and preferably represents tetrahydrofuran-2-carbonyl, pyrrolidine-1-carbonyl, pyrrolidine-2-carbonyl, pyrrolidine-3-carbonyl, pyrrolinecarbonyl, piperidinecarbonyl, morpholinecarbonyl, perhydroazepinecarbonyl.

Halogen represents fluorine, chlorine, bromine and iodine.

Amino acid side chain represents the organic substituent of an α-amino acid, which is bound to the α-carbon atom of the amino acid. Preferred are the side chains of natural α-amino acids.

These are for example hydrogen(glycine), methyl(alanine), propan-2-yl(valine), 2-methyl-propan-1-yl(leucine), 1-methyl-propan-1-yl(isoleucine), (3-indolyl)-methyl(tryptophan), benzyl(phenylalanine), methylthioethyl(methionine), hydroxymethyl(serine), p-hydroxybenzyl(tyrosine), 1-hydroxy-ethan-1-yl(threonine), mercaptomethyl(cysteine), carbamoylmethyl(asparagine), carbamoylethyl(glutarmine), carboxymethyl(aspartic acid), carboxyethyl (glutamic acid), 4-aminobutan-1-yl(lysine), 3-guanidinopropan-1-yl(arginine), imidazol-4-ylmethyl(histidine), 3-ureidopropan-1-yl(citrulline), mercaptoethyl(homocysteine), hydroxyethyl(homoserine), 4-amino-3-hydroxybutan-1-yl(hydroxylysine), 3-amino-propan-1-yl (ornithine).

When stated, that $Y^1$, $Y^2$, $Y^3$, $Y^4$ and $Y^5$ represent CH or N, CH shall also stand for a ring carbon atom, which is substituted with a substituent $R^3$ or $R^7$.

A * symbol next to a bond denotes the point of attachment in the molecule.

In another embodiment, the present invention relates to compounds of general formula (I), wherein A represents an aryl or heteroaryl ring, $R^1$, $R^2$ and $R^3$ independently from each other represent hydrogen, halogen, nitro, cyano, trifluoromethyl, $C_1$–$C_6$-alkyl, hydroxy, $C_1$–$C_6$-alkoxy or trifluoromethoxy, wherein $C_1$–$C_6$-alkyl and $C_1$–$C_6$-alkoxy can be further substituted with one to three identical or different radicals selected from the group consisting of hydroxy and $C_1$–$C_4$-alkoxy, $R^4$ represents $C_1$–$C_6$-alkylcarbonyl, $C_1$–$C_6$-alkoxycarbonyl, hydroxycarbonyl, aminocarbonyl, mono- or di-$C_1$–$C_4$-alkylaminocarbonyl or cyano, wherein $C_1$–$C_6$-alkylcarbonyl, $C_1$–$C_6$-alkoxycarbonyl, mono- and di-$C_1$–$C_4$-alkylaminocarbonyl can be substituted with one to three identical or different radicals selected from the group consisting of hydroxy, $C_1$–$C_4$-alkoxy, hydroxycarbonyl, $C_1$–$C_4$-alkoxycarbonyl, amino, mono- and di-$C_1$–$C_4$-alkylamino, aminocarbonyl, mono- and di-$C_1$–$C_4$-alkylaminocarbonyl, $C_1$–$C_4$-alkylcarbonylamino and heteroaryl, $R^5$ represents $C_1$–$C_4$-alkyl, $R^6$ represents hydrogen, cyano, aminocarbonyl, mono- or di-$C_1$–$C_4$-alkylaminocarbonyl, $C_3$–$C_8$-cycloalkylaminocarbonyl, $C_1$–$C_6$-alkylcarbonyl, hydroxycarbonyl or $C_1$–$C_6$-alkoxycarbonyl, wherein mono- and di-$C_1$–$C_4$-alkylaminocarbonyl, $C_1$–$C_6$-alkylcarbonyl and $C_1$–$C_6$-alkoxycarbonyl can be substituted with one to three identical or different radicals selected from the group consisting of hydroxy, $C_1$–$C_4$-alkoxy, hydroxycarbonyl, $C_1$–$C_4$-alkoxycarbonyl, amino, mono- and di-$C_1$–$C_4$-alkylamino, aminocarbonyl, mono- and di-$C_1$–$C_4$-alkylaminocarbonyl, $C_1$–$C_4$-alkylcarbonylamino, phenyl and heteroaryl, or $R^6$ represents a moiety of the formula

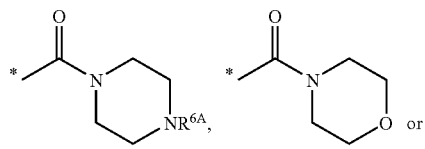

-continued

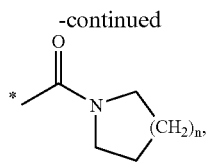

wherein $R^{6A}$ is selected from the group consisting of hydrogen and $C_1$–$C_6$-alkyl, and n represents an integer of 1 or 2, or $R^6$ represents a moiety of the formula

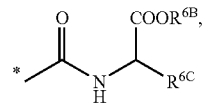

wherein $R^{6B}$ is selected from the group consisting of hydrogen and $C_1$–$C_6$-alkyl, and $R^{6C}$ is an amino acid side chain, $R^7$ represents hydrogen, halogen, nitro, cyano, trifluoromethyl, $C_1$–$C_6$-alkyl, hydroxy, $C_1$–$C_6$-alkoxy or trifluoromethoxy, wherein $C_1$–$C_6$-alkyl and $C_1$–$C_6$-alkoxy can be further substituted with one to three identical or different radicals selected from the group consisting of hydroxy and $C_1$–$C_4$-alkoxy, and $Y^1$, $Y^2$, $Y^3$, $Y^4$ and $Y^5$ independently from each other represent CH or N, wherein the ring contains either 0, 1 or 2 nitrogen atoms.

In another embodiment, the present invention relates to compounds of general formula (I), wherein A represents an aryl ring, $R^1$, $R^2$ and $R^3$ independently from each other represent hydrogen, fluoro, chloro, bromo, nitro, cyano, methyl, ethyl, trifluoromethyl or trifluoromethoxy, $R^4$ represents $C_1$–$C_6$-alkylcarbonyl, $C_1$–$C_6$-alkoxycarbonyl or cyano, wherein $C_1$–$C_6$-alkylcarbonyl and $C_1$–$C_6$-alkoxycarbonyl can be substituted with one to two identical or different radicals selected from the group consisting of hydroxy, methoxy, hydroxycarbonyl, methoxycarbonyl, amino, mono- and di-$C_1$–$C_4$-alkylamino, $R^5$ represents methyl or ethyl, $R^6$ represents hydrogen, cyano, aminocarbonyl, mono- or di-$C_1$–$C_4$-alkylaminocarbonyl, hydroxycarbonyl or $C_1$–$C_6$-alkoxycarbonyl, or $R^6$ represents a moiety of the formula

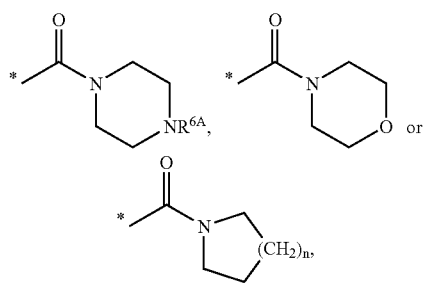

wherein $R^{6A}$ is selected from the group consisting of hydrogen, methyl and ethyl, and n represents an integer of 1 or 2, or $R^6$ represents a moiety of the formula

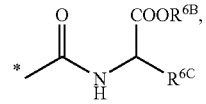

wherein $R^{6B}$ is selected from the group consisting of hydrogen, methyl and ethyl, and $R^{6C}$ is an amino acid side chain, $R^7$ represents hydrogen, halogen, nitro, cyano, trifluoromethyl, trifluoromethoxy, methyl or ethyl, and $Y^1$, $Y^2$, $Y^3$, $Y^4$ and $Y^5$ each represent CH.

In another embodiment, the present invention relates to compounds of general formula (I), wherein A represents a phenyl ring, $R^1$ represents hydrogen or methyl, $R^2$ represents cyano, bromo or nitro, $R^3$ represents hydrogen, $R^4$ represents $C_1$–$C_4$-alkylcarbonyl, $C_1$–$C_4$-alkoxycarbonyl or cyano, wherein $C_1$–$C_4$-alkylcarbonyl and $C_1$–$C_4$-alkoxycarbonyl can be substituted with hydroxycarbonyl or $C_1$–$C_4$-alkoxycarbonyl, $R^5$ represents methyl, $R^6$ represents hydrogen, cyano, aminocarbonyl, mono- or di-$C_1$–$C_4$-alkylaminocarbonyl, hydroxycarbonyl or $C_1$–$C_6$-alkoxycarbonyl, $R^7$ represents trifluoromethyl or nitro, and $Y^1$, $Y^2$, $Y^3$, $Y^4$ and $Y^5$ each represent CH.

In another embodiment, the present invention relates to compounds according to general formula (I), wherein A is phenyl.

In another embodiment, the present invention relates to compounds according to general formula (I), wherein $R^1$ is hydrogen.

In another embodiment, the present invention relates to compounds according to general formula (I), wherein $R^2$ is cyano, especially wherein A is phenyl and $R^2$ is cyano located in para-position relative to the dihydropyridinone ring.

In another embodiment, the present invention relates to compounds according to general formula (I), wherein $R^3$ is hydrogen.

In another embodiment, the present invention relates to compounds according to general formula (I), wherein $R^4$ is $C_1$–$C_6$-alkylcarbonyl, $C_1$–$C_6$-alkoxycarbonyl or cyano.

In another embodiment, the present invention relates to compounds according to general formula (I), wherein $R^5$ is methyl.

In another embodiment, the present invention relates to compounds according to general formula (I), wherein $R^6$ is hydrogen, cyano, aminocarbonyl, mono- and di-methyl- or -ethylaminocarbonyl, methoxycarbonyl or ethoxycarbonyl.

In another embodiment, the present invention relates to compounds according to general formula (I), wherein $R^7$ is trifluoromethyl or nitro.

In another embodiment, the present invention relates to compounds of general formula (IA)

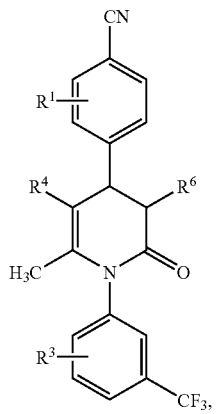

(IA)

wherein $R^1$, $R^3$, $R^4$ and $R^6$ have the meaning indicated above.

The compounds of the present invention can enolize into the corresponding enoles:

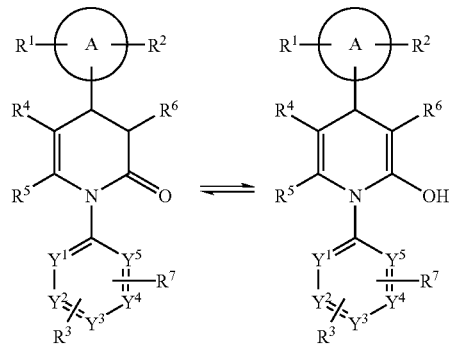

In another embodiment, the present invention relates to processes for synthesizing the compounds of general formula (I), characterized in that

[A] compounds of the general formula (II)

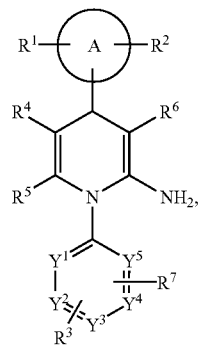

(II)

wherein $R^1$ to $R^7$, A and $Y^1$ to $Y^5$ have the meaning described above,
are hydrolyzed with water, or

[B] compounds of the General Formula (III)

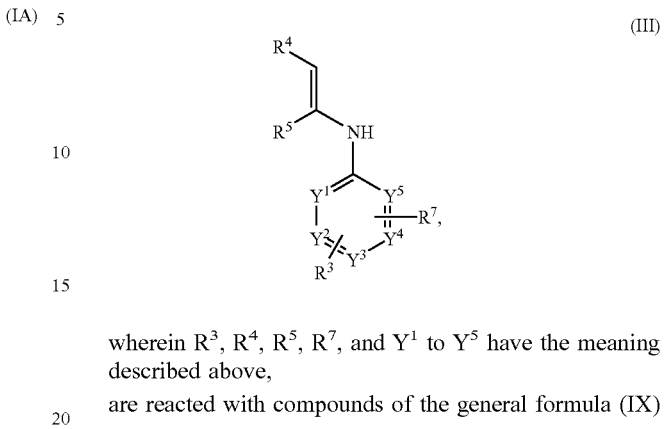

(III)

wherein $R^3$, $R^4$, $R^5$, $R^7$, and $Y^1$ to $Y^5$ have the meaning described above,
are reacted with compounds of the general formula (IX)

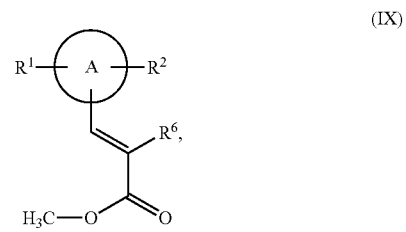

(IX)

wherein $R^1$, $R^2$, $R^6$ and A have the meaning described above, or

[C] compounds of the general formula (II)

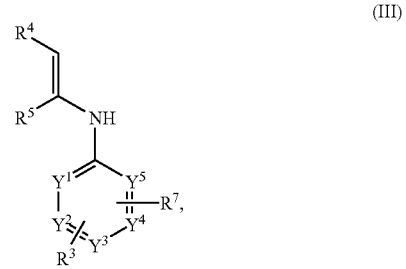

(III)

wherein $R^3$, $R^4$, $R^5$, $R^7$, and $Y^1$ to $Y^5$ have the meaning described above,
are reacted with compounds of the general formula (VIII)

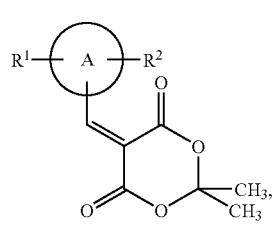

(VIII)

wherein $R^1$ and $R^2$ have the meaning described above.

Process [A]

Suitable solvents for the process are generally customary organic solvents which do not change under the reaction conditions. These include ethers such as diethyl ether, diisopropyl ether, 1,2-dimethoxyethane, dioxan or tetrahydrofiran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is water and acetic acid.

The process can take place in the presence of an acid. Suitable acids for the process are generally inorganic or organic acids. These preferably include carboxylic acids, such as, for example acetic acid or trifluoroacetic acid, or sulfonic acids, such as, for example, methanesulfonic acid or p-toluenesulfonic acid. Preference is given to acetic acid or trifluoroacetic acid. The acid is employed in an amount from 0.25 mol to 100 mol, relative to 1 mol of the compound of the general formula (II).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of general formula (II) can be synthesized by condensing compounds of general formula (III)

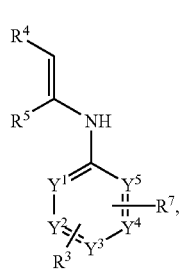

(III)

wherein $R^3$, $R^4$, $R^5$, $R^7$, and $Y^1$ to $Y^5$ have the meaning described above, in the presence of a base, in a three-component-reaction, with compounds of the general formulas (IV) and (V)

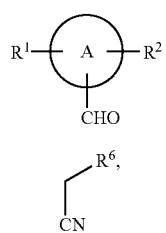

(IV)

(V)

wherein $R^1$, $R^2$, $R^6$ and A have the meaning described above.
Alternatively, in a first step compounds of the general formulas (IV) and (V) can be reacted, and the resulting product is reacted with or without isolation with compounds of the general formula (III) in a second step.

Suitable solvents for the process are generally customary organic solvents which do not change under the reaction conditions. These include ethers such as diethyl ether, diisopropyl ether, 1,2-dimethoxyethane, dioxan or tetrahydrofiran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is ethanol.

Suitable bases for the process are generally inorganic or organic bases. These preferably include cyclic amines, such as, for example, piperidine, morpholine, N-methylmorpholine, pyridine or 4-N,N-dimethylaminopyridine, or ($C_1$–$C_4$)-trialkyl-amines, such as, for example, triethylamine or diisopropylethylamine. Preference is given to piperidine. The base is employed in an amount from 0.1 mol to 10 mol, preferably from 0.1 mol to 1 mol, relative to 1 mol of the compound of the general formula (II).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of general formula (III) can be synthesized by reacting compounds of general formula (VI)

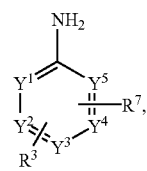

(VI)

wherein $R^3$, $R^7$, and $Y^1$ to $Y^5$ have the meaning described above, with compounds of the general formula (VII)

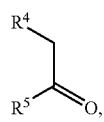

(VII)

wherein $R^4$ and $R^5$ have the meaning described above.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. For the process also acetic acid can be employed as solvent. It is also possible to use mixtures of the abovementioned solvents. Preferred for the process is ethanol, toluene or benzene.

Suitable acids for the process are generally inorganic or organic acids. These preferably include carboxylic acids, such as, for example acetic acid or trifluoroacetic acid, or sulfonic acids, such as, for example, methanesulfonic acid or p-toluenesulfonic acid. Preference is given to acetic acid or trifluoroacetic acid. The acid is employed in an amount from 0.25 mol to 100 mol, relative to 1 mol of the compounds of the general formulas (V) and (VI), respectively.

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formulas (IV), (V), (VI) and (VII) are known per se, or they can be prepared by customary methods.

Process [B]

For process [B], compounds of the general formula (IX) can be prepared in situ or in a first step compounds of the general formulas (I) and (X) can be reacted, and the resulting product is reacted with compounds of the general formulas (III) in a second step.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the abovementioned solvents. Preferred for the process is ethanol.

Suitable bases for the process are generally inorganic or organic bases. These preferably include cyclic amines, such as, for example, piperidine, morpholine, N-methylmorpholine, pyridine or 4-N,N-dimethylaminopyridine, or ($C_1$–$C_4$)-trialkyl-amines, such as, for example, triethylamine or diisopropylethylamine. Preference is given to piperidine. The base is employed in an amount from 0.1 mol to 10 mol, preferably from 0.1 mol to 1 mol, relative to 1 mol of the compound of the general formula (II).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formula (IX) are known per se, or they can be prepared by reacting compounds of general formula (IV), wherein $R^1$, $R^2$ and A have the meaning described above, with compounds of general formula (X)

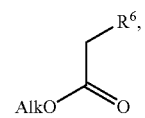

(X)

wherein $R^6$ has the meaning described above and Alk stands for alkyl, in the presence of a base.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the abovementioned solvents. Preferred for the process is methanol, ethanol or toluene.

Suitable bases for the process are generally inorganic or organic bases. These preferably include cyclic amines, such as, for example, piperidine, morpholine, N-methylmorpholine, pyridine or 4-N,N-dimethylaminopyridine, or ($C_1$–$C_4$)-trialkyl-amines, such as, for example, triethylamine or diisopropylethylamine. Preference is given to piperidine. The base is employed in an amount from 0.1 mol to 10 mol, preferably from 1 mol to 3 mol, relative to 1 mol of the compound of the general formula (X).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formula (X) are known per se, or they can be prepared by customary methods.

Process [C]

Suitable solvents for the process are generally customary organic solvents which do not change under the reaction conditions. These include ethers such as diethyl ether, diisopropyl ether, 1,2-dimethoxyethane, 1-methoxy-2-(2-methoxyethoxy)-ethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is 1-methoxy-2-(2-methoxyethoxy)-ethane or acetic acid.

The process is in general carried out in a temperature range from +20° C. to +200° C., preferably from +100° C. to +180° C.

The process is generally carried out at normal pressure. However, it is also possible to carry it out at elevated pressure or at reduced pressure (for example in a range from 0.5 to 5 bar).

The compounds of the general formula (VIII) can be synthesized by reacting compounds of general formula (IV), wherein $R^1$ and $R^2$ have the meaning described above, with 2,2-dimethyl-1,3-dioxane-4,6-dione.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is water.

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The above-mentioned methods can be illustrated by the following schemes:

[A]
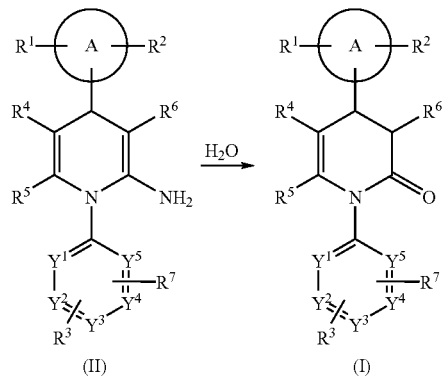

[B]
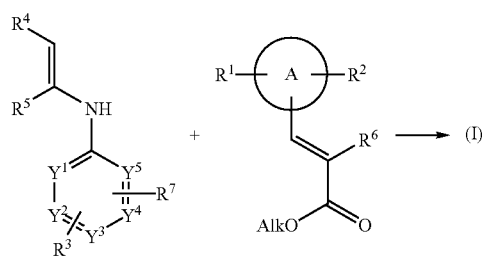

[C]
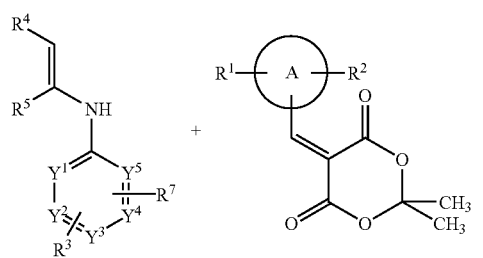

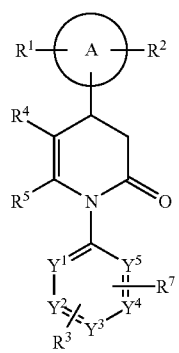

Compounds of the general formula (IB)

(IB)

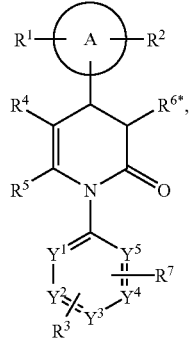

wherein $R^1$ to $R^5$, $R^7$, A, and $Y^1$ to $Y^5$ have the meaning described above, and $R^{6*}$ represents di-$C_1$–$C_6$-alkylaminocarbonyl, N-aryl-N—$C_1$–$C_6$-alkylaminocarbonyl or a moiety of the formula

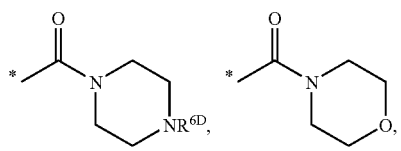

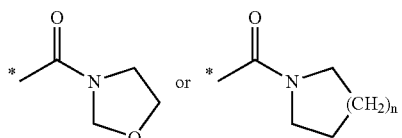

wherein $R^{6D}$ selected from the group consisting of $C_1$–$C_6$-alkyl and $C_1$–$C_4$-alkylcarbonyl, Q represents O or S, and n represents an integer of 1 or 2, can also be prepared by reacting compounds of general formula (XI)

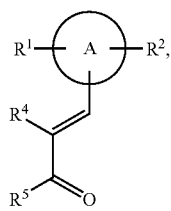
(XI)

wherein $R^1$, $R^2$, $R^4$, $R^5$ and A have the meaning described above, with compounds of general formula (XII)

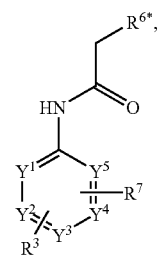
(XII)

wherein $R^3$, $R^{6*}$, $R^7$, and $Y^1$ to $Y^5$ have the meaning described above, in the presence of N-tetrabutylammoniumfluoride to give compounds of general formula (XIII)

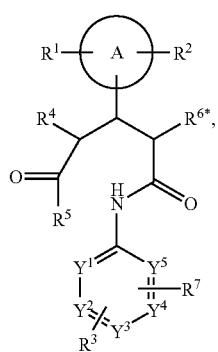
(XIII)

wherein $R^1$ to $R^5$, $R^{6*}$, $R^7$, A, and $Y^1$ to $Y^5$ have the meaning described above, which are then cyclized to compounds of general formula (IB) in the presence of an acidic ion exchange resin, such as Amberlyst®-15, and a dehydrating agent, such as magnesium sulfate.

The process (XI)+(XII)→(XIII) is preferably carried out at room temperature in tetrahydrofuran as solvent. The process (XIII)→(IB) is preferably carried out in alcoholic solvents, such as methanol or ethanol, at a temperature range from +20° C. to +80° C.

The compounds of the general formula (XI) are available by Knoevenagel condensation between the compounds of general formula (IV) and (VII).

The compounds of the general formula (XII) can be synthesized following the reaction sequence illustrated below:

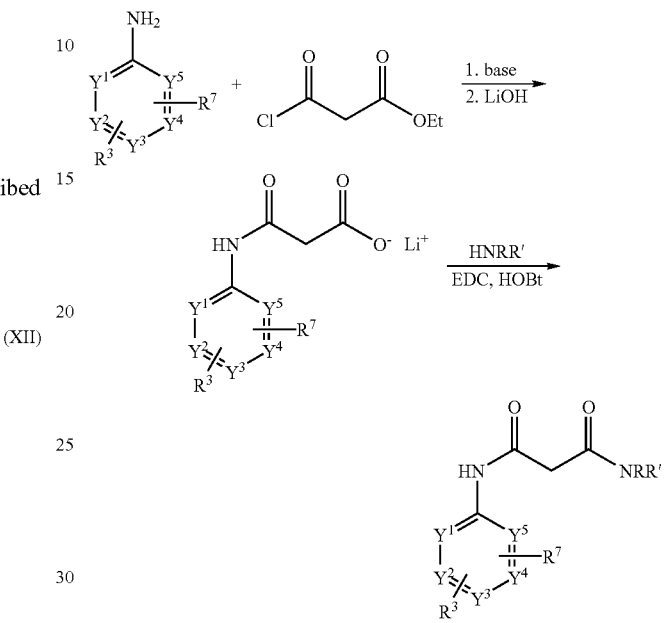

The compounds according to the invention exhibit an unforeseeable, useful pharmacological and pharmacokinetic activity spectrum.

They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty (PTCA), inflammation after open heart surgery and for pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharmacologically safe excipient or carrier substances, and also their use for the above-mentioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinyl-pyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. Evaluation of Physiological Activity

The potential of the compounds of the invention to inhibit neutrophil elastase activity may be demonstrated, for example, using the following assays:

I. In Vitro Enzyme Assays of Human Neutrophil Elastase (HNE)

Assay Contents assay buffer: 0.1 M HEPES-NaOH buffer pH 7.4, 0.5 M NaCl, 0.1% (w/v) bovine serum albumin;

suitable concentration (see below) of HNE (18 U/mg lyophil., #20927.01, SERVA Electrophoresis GmbH, Heidelberg, Germany) in assay buffer;

suitable concentration (see below) of substrate in assay buffer;

suitable concentration of test compounds diluted with assay buffer from a 10 mM stock solution in DMSO.

EXAMPLE A

In Vitro Inhibition of HNE Using a Fluorogenic Peptide Substrate (Continuous Read-out Signal, 384 MTP Assay Format)

In this protocol, the elastase substrate MeOSuc-Ala-Ala-Pro-Val-AMC (#324740, Calbiochem-Novabiochem Corporation, Merck KGaA, Darmstadt, Germany) is used. The test solution is prepared by mixing 10 µl of test compound dilution, 20 µl of HNE enzyme dilution (final concentration 8–0.4 µU/ml, routinely 2.1 µU/ml) and 20 µl of substrate dilution (final concentration 1 mM–1 µM, routinely 20 µM), respectively. The solution is incubated for 0–2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 nm, em. 460 m) is proportional to elastase activity. $IC_{50}$ values are determined by RFU-versus-[I] plots. $K_m$ and $K_{m(app.)}$ values are determined by Lineweaver-Burk plots and converted to $K_i$ values by Dixon plots.

The preparation examples had $IC_{50}$ values within the range of 5 nM-5 µM in this assay. Representative data are given in Table 1:

TABLE 1

| Example No. | $IC_{50}$ [nM] |
| --- | --- |
| 1 | 30 |
| 3 | 20 |
| 4 | 40 |
| 7 | 13 |
| 12 | 25 |
| 13 | 25 |
| 14 | 70 |
| 15 | 200 |
| 19 | 25 |
| 20 | 30 |
| 43 | 20 |
| 68 | 15 |
| 77 | 350 |
| 98 | 8 |

EXAMPLE B

In Vitro Inhibition of HNE Using a Fluorogenic, Unsoluble Elastin Substrate (Discontinuous Read-out Signal, 96 MTP Assay Format)

In this protocol the elastase substrate elastin-fluorescein (#100620, ICN Biomedicals GmbH, Eschwege, Germany) is used. The test solution is prepared by mixing 3 µl of test compound dilution, 77 µl of HNE enzyme dilution (final concentration 0.22 U/ml–2.2 mU/ml, routinely 21.7 µU/ml) and 80 µl substrate suspension (final concentration 2 mg/ml). The suspension is incubated for 0–16 hrs at 37° C. (routinely four hours) under slightly shaking conditions. To stop the enzymatic reaction, 160 µl of 0.1 M acetic acid are added to the test solution (final concentration 50 mM). The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In Vitro Human Neutrophil Assays

EXAMPLE A

In Vitro PMN Elastolysis Assay

This assay is used to determine the elastolytic potential of human polymorphonuclear cells (PMNs) and assess the proportion of degradation due to neutrophil elastase [cf. Z. W. She et al., Am. J. Respir. Cell. Mol. Biol. 9, 386–392 (1993)].

Tritiated elastin, in suspension, is coated on to a 96 well plate at 10 µg per well. Test and reference [ZD-0892 (J. Med. Chem. 40, 1876–1885, 3173–3181 (1997), WO 95/21855) and al protease inhibitor (α1PI)] compounds are added to the wells at the appropriate concentrations. Human PMNs are separated from peripheral venous blood of healthy donors and resuspended in culture media. The neutrophils are added to the coated wells at concentrations ranging between $1 \times 10^6$ to $1 \times 10^5$ cells per well. Porcine pancreatic elastase (1.3 µM) is used as a positive control for the assay, and α1PI (1.2 µM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 µl volumes to corresponding wells of a 96 well Lumaplate™ (solid scintillant containing plates). The plates are dried until no liquid is visible in the wells and read in a beta counter for 3 minutes per well.

Elastolysis of the ³H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 µM (n=3 different donors at $3.6 \times 10^5$ cells per well). $IC_{50}$ values were obtained for the reference compound ZD-0892 of 45.50±7.75 nM (mean±s.e.m.) (n=2 different donors at $3.6 \times 10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

EXAMPLE B

In Vitro Inhibition of Membrane Bound Elastase

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeOSuc-Ala-Ala-Pro-Val-AMC (#324740, Calbiochem-Novabiochem Corporation, Merck KGaA, Darmstadt, Germany) at 200 µM. Following a 25 min incubation at 37° C., the reaction is terminated with PMSF (phenylmethanesulfonyl fluoride), and the fluorescence is read at ex: 400 nm and em: 505 nm. $IC_{50}$ values are determined by interpolation from plots of relative fluorescence vs. inhibitor concentration.

III. In Vivo Models

EXAMPLE A

In Vivo Model of Acute Lung Injury in the Rat

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4–10° C. The supernatant is discarded and the cell pellet resuspended in PBS and the sample spun down again. The supernatant is again discarded and the cell pellet resuspended in 1 ml 0.1% cetyltrimethyl-ammonium bromide (CTAB)/PBS to lyse the cells. Samples are frozen until blood content is assayed. Prior to the haemorrhage assay the samples are defrosted and mixed. 100 µl of each sample are placed into a separate well of a 96 well flat-bottomed plate. All samples are tested in duplicate. 100 µl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced haemorrhage in the rat.

EXAMPLE B

In Vivo Model of Acute Myocardial Infarction in the Rat

Elastase inhibitors are tested in a rat thread infarct model. Male Wistar rats (weighing>300 g) receive 10 mg/kg aspirin 30 min prior to surgery. They are anaesthetized by isofluran and ventilated (120–130 strokes/min, 200–250 µl stroke volume; MiniVent Type 845, Hugo Sachs Elektronik, Germany) during the whole surgery. Following a left thoracotomy at the fourth intercostal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 min, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the re-occluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. EXAMPLE

Abbreviations:
DCI direct chemical ionisation (for MS)
DMSO dimethylsulfoxide
EDC N'-(3-dimethylaminopropyl)-N-ethylcarbodiimide×HCl
EI electron impact ionisation (for MS)
ESI electro-spray ionisation (for MS)
HOBt 1-hydroxy-1H-benzotriazol×$H_2O$
HPLC high pressure liquid chromatography
LC-MS liquid chromatography coupled with mass spectroscopy
Mp. melting point
MS mass spectroscopy
NMR nuclear magnetic resonance
of th. of theoretical (yield)
RP reverse phase (for HPLC)
$R_t$ retention time (for HPLC)
THF tetrahydrofiran General Methods:

All reactions were carried out under an argon atmosphere unless otherwise noted. Solvents were used as purchased from Aldrich without further purification. "Silica gel" or "Silica" refers to Silica gel 60 (0.040 mm–0.063 mm) from Merck KGaA company. Compounds purified over preparative HPLC were purified over a RP18-column with acetonitrile and water as the eluent, using a 1:9 to 9:1 gradient.

LC-MS and HPLC Methods:

Method 1 (LC-MS)
Instrument MS: Micromass ZQ; Instrument HPLC: Waters Alliance 2790; Column: Symmetry C 18, 50 mm×2.1 mm, 3.5 µm; Eluent A: water+0.05% formic acid; Eluent B: acetonitrile+0.05% formic acid; Gradient: 0.0 min 10% B→3.5 min 90% B→5.5 min 90% B; Oven: 50° C.; Flow: 0.8 ml/min; UV-detection: 210 nm.

Method 2 (LC-MS)
Instrument: Micromass Quattro LCZ, HP1 100; Column: Symmetry C18, 50 mm×2.1 mm, 3.5 µm; Eluent A: water+0.05% formic acid; Eluent B: acetonitrile+0.05% formic acid; Gradient: 0.0 min 90% A→4.0 min 10% A→6.0 min 10% A; Oven: 40° C.; Flow: 0.5 ml/min; UV-detection: 208–400 nm.

Method 3 (LC-MS)
Instrument: Micromass Platform LCZ, HP1100; Column: Symmetry C18, 50 mm×2.1 mm, 3.5 µm; Eluent A: water+0.05% formic acid; Eluent B: acetonitrile+0.05% formic acid; Gradient: 0.0 min 90% A→4.0 min 10% A→6.0 min 10% A; Oven: 40° C.; Flow: 0.5 ml/min; UV-detection: 208–400 nm.

Method 4 (LC-MS)
Instrument: Waters Alliance 2790 LC; Column: Symmetry C18, 50 mm×2.1 mm, 3.5 µm; Eluent A: water+0.1% formic acid; Eluent B: acetonitrile+0.1% formic acid; Gradient: 0.0 min 5% B→5.0 min 10% B→6.0 min 10% B; Temperature: 50° C.; Flow: 1.0 ml/min; UV-detection: 210 nm.

Method 5 (HPLC)
Instrument: HP 1100 with DAD-detection; Column: Kromasil RP-18, 60 mm×2 mm, 3.5 µm; Eluent A: 5 ml $HClO_4$/l $H_2O$; Eluent B: acetonitrile; Gradient: 0 min 2% B, 0.5 min 2% B, 4.5 min 90% B, 6.5 min 90% B; Temperature: 30° C.; Flow: 0.75 ml/min; UV-detection: 210 nmn.

Method 6 (LC-MS)
Instrument MS: Micromass ZQ; Instrument HPLC: Waters Alliance 2790; Column: Uptisphere HDO, 50 mm×2.0 mm, 3.0 µm; Eluent A: water+0.05% formic acid; Eluent B: acetonitrile+0.05% formic acid; Gradient: 0.0 min 5% B→2.0 mnin 40% B→4.5 min 90% B→5.5 min 90% B; Oven: 45° C.; Flow: 0.75 ml/min; UV-detection: 210 nm.

Method 7 (LC-MS)
Instrument: Micromass Platform LCZ, HP1100; Column: Grom-Sil 120 ODS-4 HE, 50 mm×2.0 mm, 3 µm; Eluent A: water+0.05% formic acid; Eluent B: acetonitrile+0.05% formic acid; Gradient: 0.0 min 100% A→0.2 min 100% A→2.9 min 30% A→3.1 min 10% A→4.5 min 10% A; Oven: 55° C.; Flow: 0.8 ml/min; UV-detection: 208–400 nm.

Method 8 (LC-MS)
Instrument MS: Micromass ZQ; Instrument HPLC: Waters Alliance 2790; Column: Grom-Sil 120 ODS-4 HE 50 mm×2 mm, 3.0 µm; Eluent B: acetonitrile+0.05% formic acid; Eluent A: water+0.05% formic acid; Gradient: 0.0 min 5% B→2.0 min 40% B→4.5 min 90% B→5.5 min 90% B; Oven: 45° C.; Flow: 0.0 min 0.75 ml/min→4.5 min 0.75 ml/min→5.5 min 1.25 ml/min; WV-detection: 210 nm.

Method 9 (HPLC)
Instrument: HP 1100; Column: Kromasil RP-18, 60 mm×2 mm, 3.5 µm; Eluent A: 5 ml $HClO_4$/l $H_2O$; Eluent B: acetonitrile; Gradient: 0 min 2% B→0.5 min 2% B→4.5 min 90% B→9 min 90% B; Flow: 0.75 ml/min; Temperature: 30° C.; UV-detection: 210 nm.

Method 10 (HPLC)
Instrument: BP 1100; Column: Kromasil RP-18, 125 mm×2 mm, 3.5 µm; Eluent A: PIC B7 Heptanesulfonic acid (Waters Part-No. WAT084282); Eluent B: acetonitrile; Gradient: 0 min 2% B→1 min 2% B→9 min 90% B→13 min 90% B; Flow: 2 ml/min; Temperature: 30° C.; UV-detection: 210 nm.

Method 11 (LC-MS)

Instrument: Micromass Quattro LCZ with HPLC Agilent series 1100; column: Grom-Sil 120 ODS-4 HE, 50 mm×2.0 mm, 3 μm; Eluent A: 1 l water+1 ml 50% formic acid; Eluent B: 1 l acetonitrile+1 ml 50% formic acid; Gradient: 0.0 min 100% A→0.2 min 100% A→2.9 min 30% A→3.1 min 10% A→4.5 min 10% A; Oven: 55° C.; Flow: 0.8 ml/nin; UV-detection: 208–400 mn.

Starting Materials:

Example 1A

Ethyl-3-{[3-(trifluoromethyl)phenyl]amino}-2-butenoate

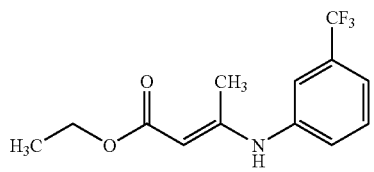

3-Trifluoromethylaniline (2.50 g, 15.5 mmol) and ethyl acetoacetate (2.32 g, 17.8 mmol) are dissolved in absolute ethanol in a 500 ml round bottom flask equipped with a stir bar and a reflux condenser. Magnesium sulphate monohydrate (2.58 g, 18.6 mmol) and glacial acetic acid (14 mg, 0.23 mmol) are added. The suspension is stirred rigorously at reflux for 16 hours under an argon atmosphere. The crude reaction mixture is cooled to room temperature, filtered and concentrated in vacuo to give an oil. The oil is chromatographed over silica gel with cyclohexane/ethyl acetate mixtures as eluent to yield a pale yellow oil which is analytically pure.

Yield: 1 g (27% of th.) $^1$H-NMR (300 MHz, DMSO-$d_6$): δ=1.2 (t, 3H); 2.0 (s, 3H); 4.1 (q, 2H); 4.8 (s, 1H); 7.5 (m, 4H); 10.4 (s, 1H) ppm.

Example 2A

3-{[3-(Trifluoromethyl)phenyl]amino}-2-butenenitrile

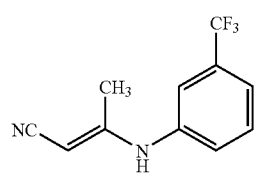

3-Aminocrotonitrile (1.0 g, 12.2 mmol), 3-trifluoromethylaniline (2.0 g, 12.4 mmol), and acetic acid (1.23 g, 20.5 mmol) are dissolved in water (8 ml). The reaction mixture is stirred at room temperature for 30 minutes. The mixture is extracted with toluene three times and the organic phase is dried over sodium sulfate. The solvent is removed in vacuo and the residue is purified by column chromatography on silica with cyclohexane/ethyl acetate mixtures as eluent.

Yield: 0.64 g (23% of th.) $^1$H-NMR (300 MHz, DMSO-$d_6$): δ=2.2 (s, 3H); 4.6 (s, 1H); 7.4–7.6 (m, 4H); 9.0 (s, 1H) ppm.

Example 3A (1R)-2-Methoxy-1-methyl-2-oxoethyl 3-oxobutanoate

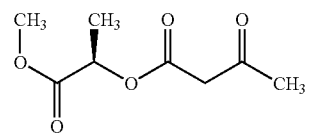

Methyl (2R)-2-hydroxypropanoate (5.0 g, 48 mmol) and triethylamine (49 mg, 0.48 mmol) are dissolved in toluene (40 ml). At 90° C., diketene (5.2 g, 62.4 mmol) is added dropwise. The reaction mixture is stirred at 100° C. for one hour. After cooling to room temperature, the mixture is poured into ice-water. The phases are separated and the aqueous phase is extracted with toluene two times. The combined organic phases are dried over sodium sulfate, the solvent is removed in vacuo and the residue is purified by column chromatography on silica with cyclohexane/ethyl acetate mixtures as eluent.

Yield: 8 g (89% of th.) $^1$H-NMR (300 MHz, DMSO-$d_6$): δ=1.4 (d, 3H); 2.2 (s, 3H); 3.7 (s, 3H, s, 2H); 5.1 (q, 1H) ppm.

Example 4A (1R)-2-Methoxy-1-methyl-2-oxoethyl (2E)-3-{[3-(trifluoromethyl)phenyl]amino}-2-butenoate

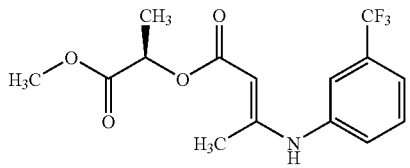

Example 3A (1 g, 5.31 mmol) and 3-trifluoromethylaniline (0.98 g, 6.11 mmol) are dissolved in ethanol (20 ml), and acetic acid (6 mg, 0.11 mmol) and magnesium sulfate monohydrate (1.28 g, 10.63 mmol) are added. The reaction mixture is stirred at reflux overnight. The mixture is filtrated, the solution is evaporated to dryness in vacuo and the residue is purified by column chromatography on silica with cyclo-hexane/ethyl acetate mixtures as eluent.

Yield: 0.8 g (45% of th.) $^1$H-NMR (200 MHz, DMSO-$d_6$): δ=1.3 (d, 3H); 2.3 (s, 3H); 3.6 (s, 3H); 4.8 (s, 1H); 5.0 (m, 1H); 7.5 (m, 4H); 8.9 (s, 1H) ppm.

Example 5A

4-{[3-(Trifluoromethyl)phenyl]amino}-3-penten-2-one

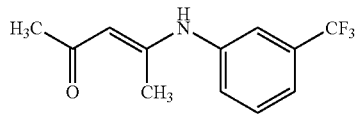

Acetylacetone (15.53 g, 155 mmol), 3-trifluoromethylaniline (5.00 g, 31 mmol), and 4-toluenesulfonic acid (0.53 g, 3.1 mmol) are dissolved in toluene (50 ml). The reaction mixture is refluxed overnight with a Dean-Stark trap to remove water. After cooling to room temperature, the solvent is removed in vacuo and the residue is purified by column chromatography on silica with cyclohexane/ethyl acetate mixtures as eluent.

Yield: 5.46 g (72% of th.) $^1$H-NMR (200 MHz, DMSO-$d_6$): δ=2.0 (s, 3H); 2.1 (s, 3H); 5.3 (s, 1H); 7.5 (m, 4H); 12.5 (s, 1H) ppm.

Example 6A

Ethyl 5-acetyl-2-amino-4-(4-cyanophenyl)-6-methyl-1-[3-(trifluoromethyl)phenyl]-1,4-dihydro-3-pyridinecarboxylate

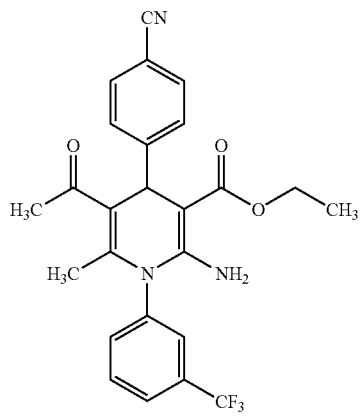

Example 5A (100 mg, 0.41 mmol) is dissolved in ethanol (2 ml), and 4-cyanobenzaldehyde (54 mg, 0.41 mmol), ethyl cyanoacetate (47 mg, 0.41 mmol) and piperidine (70 mg, 0.82 mmol) are added. The reaction mixture is stirred at reflux overnight. After cooling to room temperature, the solvent is removed in vacuo and the residue is purified by column chromatography on silica with dichloromethane as the eluent.

Yield: 26 mg (14% of th.) $^1$H-NMR (400 MHz, DMSO-$d_6$): δ=1.2 (t, 3H); 1.8 (s, 3H); 2.2 (s, 3H); 4.0 (m, 2H); 5.0 (s, 1H); 6.7 (br.s, 2H); 7.5 (m, 2H); 7.7 (m, 1H); 7.8 (m, 4H); 7.9 (m, 1H) ppm.

Example 7A

5-Acetyl-2-amino-4-(4-cyanophenyl)-6-methyl-1-[3-(trifluoromethyl)phenyl]-1,4-dihydro-3-pyridinecarboxamide

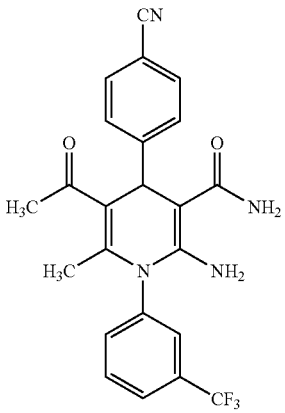

Example 5A (750 mg, 3.08 mmol) is dissolved in ethanol (5 ml), and 4-cyanobenzaldehyde (404 mg, 3.08 mmol), cyanoacetamide (260 mg, 3.08 mmol) and piperidine (26 mg, 0.31 mmol) are added. The reaction mixture is stirred at reflux overnight. After cooling to room temperature, the solvent is removed in vacuo and the residue is purified by column chromatography on silica with dichloromethane as the eluent.

Yield: 160 mg (12% of th.) $^1$H-NMR (300 MHz, DMSO-$d_6$): δ=1.8 (s, 3H); 2.2 (s, 3H); 4.9 (s, 1H); 6.7 (br.s, 2H); 6.9 (br.s, 2H); 7.5 (m, 3H); 7.8 (m, 2H); 7.9 (m, 1H); 8.0 (m, 2H) ppm.

Example 8A

5-Acetyl-4-(4cyanophenyl)-2-imino-N,N,6-trimethyl-1-[3-(trifluoromethyl)phenyl]-1,2,3,4-tetrahydro-3-pyridinecarboxamide

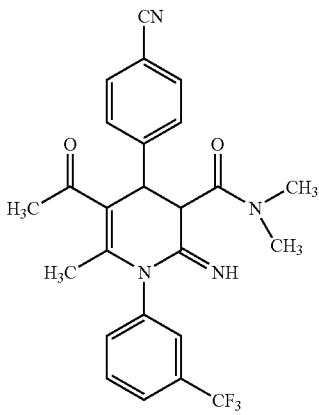

Example 5A (750 mg, 3.08 mmol) is dissolved in ethanol (5 ml), and 4-cyanobenzaldehyde (404 mg, 3.08 mmol), 2-cyano-N,N-dimethylacetamide (260 mg, 3.08 mmol) and piperidine (26 mg, 0.31 mmol) are added. The reaction mixture is stirred at reflux overnight. After cooling down to room temperature, the solvent is removed in vacuo and the residue is purified by column chromatography on silica with dichloromethane as the eluent.

Yield: 88 mg (6% of th.) ¹H-NMR (300 MHz, DMSO-d₆): δ=2.0 (s, 3H); 2.1 (s, 3H); 2.5 (s, 3H); 2.9 (s, 3H); 4.1 (d, 1H); 4.5 (d, 1H); 7.6 (m, 3H); 7.7 (m, 1H); 7.8 (m, 3H); 8.2 (s, 1H) ppm.

Example 9A

2-Amino-5-cyano4-(4-cyanophenyl)-6-methyl-1-[3-(trifluoromethyl)phenyl]-1,4-dihydro-3-pyridinecarboxamide

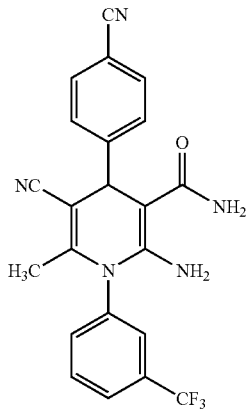

Example 2A (100 mg, 0.44 mmol), 4-formylbenzonitrile (57.97 mg, 0.44 mmol) and 2-cyanoacetamide (37.17 mg, 0.44 mmol) are dissolved in ethanol (2 ml) under an argon atmosphere. Piperidine (3.76 mg, 0.04 mmol) is added, and the mixture is stirred at reflux overnight. The product is precipitated from the reaction mixture at 4° C. The precipitate is filtered, washed twice with ethanol and dried. The solid is purified by column chromatography with dichloromethane/methanol 100:1 as eluent.

Yield: 63 mg (34% of th.) LC-MS (method 3): $R_t$=4.21 min MS (EI): m/z=424 [M+H]⁺ HPLC (method 5): $R_t$=3.99 min ¹H-NMR (200 MHz, DMSO-d₆): δ=1.68 (s, 3H); 4.76 (s, 1H); 6.42 (br.s, 2H); 7.24 (br.s, 2H); 7.63 (d, 2H); 7.77 (d, 2H); 7.82–7.95 (m, 4H) ppm.

Example 10A

Ethyl 6-amino-5-(aminocarbonyl)-4-(4-cyanophenyl)-2-methyl-1-[3-(trifluoromethyl)-phenyl]-1,4-dihydro-3-pyridinecarboxylate

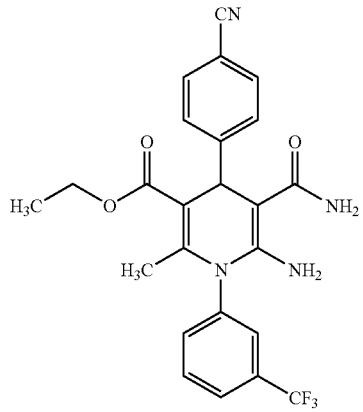

Example 1A (100 mg, 0.37 mmol), 4-formylbenzonitrile, (48.00 mg, 0.37 mmol) and 2-cyanoacetamide (30.77 mg, 0.37 mmol) are dissolved in ethanol (2 ml). Piperidine (1.56 mg, 0.02 mmol) is added, and the mixture is stirred at reflux. After one hour, piperidine (9.35 mg, 0.11 mmol) is again added, and the reaction is stirred overnight at reflux. After the reaction is finished, the mixture is purified by flash chromatography over silica gel with dichloromethane and dichloromethane/methanol 100:1→80:1 as eluent.

Yield: 40 mg (23% of th.) HPLC (method 5): $R_t$=4.18 min MS (EI): m/z=471 [M+H]⁺ ¹H-NMR (300 MHz, DMSO-d₆): δ=1.19 (t, 3H); 1.87 (s, 3H); 4.06 (q, 2H); 4.90 (s, 1H); 6.45 (br.s, 2H); 7.03 (br.s, 2H); 7.61 (d, 2H); 7.68 (d, 2H); 7.72–7.79 (m, 3H); 7.89 (d, 1H) ppm.

Example 11A

Ethyl 2-amino-5-cyano-4-(4cyanophenyl)-6-methyl-1-[3-(trifluoromethyl)phenyl]-1,4-dihydro-3-pyridinecarboxylate

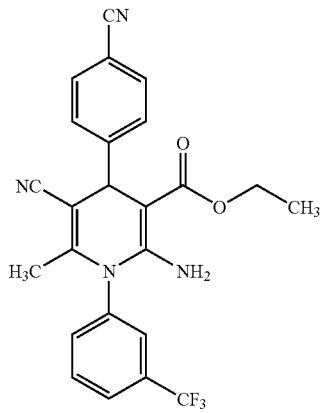

Example 2A (100 mg, 0.44 mmol), 4-formylbenzonitrile (57.97 mg, 0.44 mmol) and ethyl cyanoacetate (50.01 mg, 0.44 mmol) are dissolved in ethanol (2 ml) under an argon atmosphere. Piperidine (3.76 mg, 0.04 mmol) is added, and the mixture is stirred at reflux overnight. After cooling to room temperature, the precipitate is filtered and washed twice with ethanol. The crude solid product is purified by column chromatography over silica gel with cyclohexane/ethyl acetate mixtures as eluent.

Yield: 63 mg (32% of th.) HPLC (method 5): $R_t$=4.89 min MS (EI): m/z=453 [M+H]⁺ ¹H-NMR (300 MHz, DMSO-d₆): δ=0.97 (t, 3H); 1.72 (s, 3H); 3.88 (q, 2H); 4.59 (s, 1H); 7.04 (br.s, 2H); 7.56 (d, 2H); 7.76–7.86 (m, 4H); 7.91–7.96 (m, 1H); 7.98 (s, 1H) ppm.

Example 12A

5-Cyano-4-(4-cyanophenyl)-2-imino-N,N,6-trimethyl-1-[3-(trifluoromethyl)phenyl]-1,2,3,4-tetrahydro-3-pyridinecarboxamide

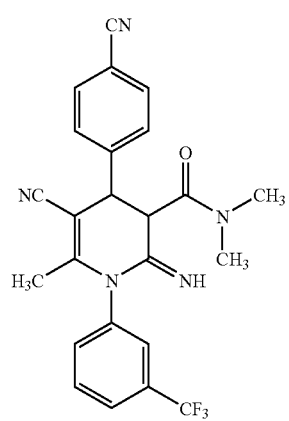

Example 2A (100 mg, 0.44 mmol), 4-formylbenzonitrile (57.97 mg, 0.44 mmol) and 2-cyano-N,N-dimethylacetamide (49.57 mg, 0.44 mmol) are dissolved in ethanol (2 ml). Piperidine (3.76 mg, 0.04 mmol) is added, and the mixture is stirred at reflux overnight. After cooling to room temperature, the crude product is purified by column chromatography with cyclohexane/ethyl acetate 20:1, 10:1, 8:1, 6:1, 4:1, 2:1, 1:1, 1:2 and dichloromethane/methanol 100:1, 50:1, 20:1 as eluent. The product fractions are re-purified by HPLC.

Yield: 70 mg (35% of th.) LC-MS (method 1): $R_t$=2.49 min MS (EI): m/z=452 [M+H]$^+$ $^1$H-NMR (300 MHz, DMSO-$d_6$): δ=1.90 (s, 3H); 2.89 (s, 3H); 3.14 (s, 3H); 4.12–4.17 (m, 1H); 4.28–4.33 (m, 1H); 7.60 (d, 2H); 7.66–7.85 (m, 4H); 7.89 (d, 2H); 8.52 (s, 1H) ppm.

Example 13A

Ethyl 4-(4-cyanophenyl)-5-[(dimethylamino)carbonyl]-6-imino-2-methyl-1-[3-(trifluoromethyl)phenyl]-1,4,5,6-tetrahydro-3-pyridinecarboxylate

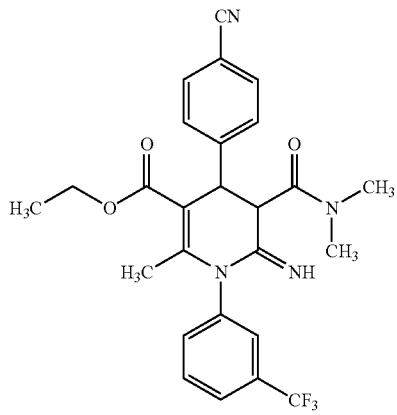

Example 1A (200 mg, 0.73 mmol), 4-formylbenzonitrile (95.98 mg, 0.73 mmol) and 2-cyano-N,N-dimethylacetamide (82.07 mg, 0.73 mmol) are dissolved in ethanol (4 ml). Piperidine (6.23 mg, 0.07 mmol) are added, and the mixture is stirred at reflux overnight. After cooling down to room temperature, the crude product is purified by column chromatography on silica with cyclohexane/ethyl acetate 2:1 and dichloromethane/methanol 100:1, 40:1 as eluent.

Yield: 29 mg (8% of th.) LC-MS (method 2): $R_t$=3.31 min MS (EI): m/z=498 [M]$^+$ $^1$H-NMR (400 MHz, DMSO-$d_6$): δ=1.04 (t, 3H); 2.08 (s, 3H); 2.89 (s, 3H); 3.21 (s, 3H); 3.97 (q, 2H); 4.20 (s, 1H); 4.35 (s, 1H); 7.54 (d, 2H); 7.59–7.65 (m, 2H); 7.67–7.76 (m, 2H); 7.83 (d, 2H); 8.27 (s, 1H) ppm.

Example 14A

3-Ethyl 5-[(1R)-2-methoxy-1-methyl-2-oxoethyl]2-amino-4-(4-cyanophenyl)-6-meth-yl-1-[3-(trifluoromethyl)phenyl]-1,4dihydro-3,5-pyridinedicarboxylate

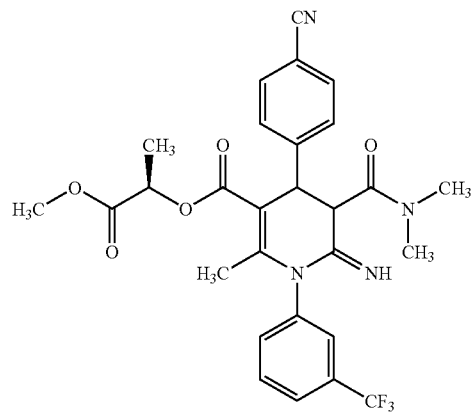

Example 4A (100 mg, 0.30 mmol) and 4-formylbenzonitrile (39.58 mg, 0.30 mmol) are dissolved in ethanol (2 ml). To this mixture, ethyl cyanoacetate (34.14 mg, 0.30 mmol) and piperidine (2.57 mg, 0.03 mmol) are added. The reaction is stirred for 30 min at room temperature and at reflux overnight. After cooling to room temperature, a precipitate is obtained. The solid is filtered and the crude product is purified by column chromatography on silica gel with dichloromethane and dichloromethane/methanol 100:1, 40:1 as eluent.

Yield: 55 mg (34% of th.) as a mixture of diastereomers HPLC (method 5): $R_t$=4.63 min MS (EI): m/z=558 [M+H]$^+$ $^1$H-NMR (300 MHz, DMSO-$d_6$): δ=1.10 (t, 6H); 1.3 (d, 3H); 1.4 (d, 3H); 1.91 (s, 3H); 1.96 (s, 3H); 3.54 (s, 3H); 3.63 (s, 3H); 3.92–4.05 (m, 4H); 4.85–4.96 (m, 2H); 4.98 (s, 2H); 6.83 (br.s, 4H); 7.51 (m, 4H); 7.73 (m, 6H); 7.77–7.93 (m, 6H) ppm.

Example 15A

Ethyl 6-amino-5-cyano-4-(4-cyanophenyl)-2-methyl-1-[3-(trifluoromethyl)phenyl]-1,4-dihydro-3-pyridinecarboxylate

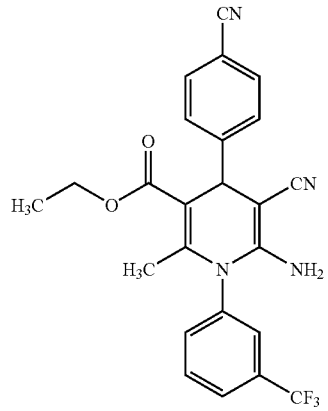

The compound is prepared as described for Example 14A with 100 mg (0.37 mmol) of the compound of Example 1A, 48 mg (0.37 mmol) 4-formylbenzonitrile, 24.18 mg (0.37 mmol) malononitrile and 3.12 mg (3.6 μl, 0.04 mmol) piperidine in 2 ml ethanol. The product is purified by HPLC.

Yield: 33 mg (20% of th.) HPLC (method 5): $R_f$=4.91 min LC-MS (method 4): $R_t$=3.59 min MS (EI): m/z =453 [M+H]$^+$ $^1$H-NMR (300 MHz, DMSO-$d_6$): δ=1.04 (t, 3H); 1.94 (s, 3H); 3.96 (q, 2H); 4.60 (s, 1H); 5.53 (s, 2H); 7.50 (d, 2H); 7.66 (d, 1H); 7.72–7.91 (m, 5H) ppm.

Example 16A

Ethyl-2-cyano-3-(4-cyanophenyl)-2-propenoate

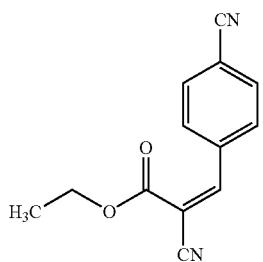

4-Cyanobenzaldehyde (3.00 g, 22.9 mmol) ad ethyl cyanoacetate (2.59 g, 22.9 mmol) are dissolved in absolute ethanol (100 ml). Piperidine (0.097 g, 1.14 mmol) is added, and the solution is stirred at room temperature until no more starting material is apparent by tlc. This takes approx. 2 hours during which time a precipitate is formed. The precipitate is filtered and recrystallised, or alternatively, the crude reaction mixture is concentrated in vacuo and chromatographed over silica with cyclohexane/ethyl acetate mixtures as eluent to yield a white solid.

Yield: 5 g (96% of th.) Mp.: 173–174° C. HPLC (method 5): $R_t$=4.47 min. $^1$H-NMR (300 MHz, CDCl$_3$): δ=8.24 (s, 1H); 8.05 (d, 2H); 7.78 (d, 2H); 4.41 (q, 2H); 1.41 (t, 3H) ppm.

Example 17A

Diethyl 2-amino-4-(4-cyanophenyl)-6-methyl-1-[3-(trifluoromethyl)phenyl]-1,4-dihydro-3,5-pyridinedicarboxylate

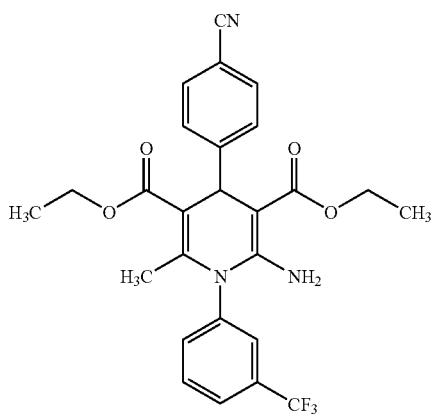

Cyanoethylacetate (2.07 g, 18.3 mmol) and 4-cyanobenzaldehyde (2.40 g, 18.3 mmol) are dissolved in ethanol (125 ml) under an argon atmosphere. Piperidine (46.7 mg, 0.55 mmol) is added, and the reaction mixture is stirred for 2 hours at room temperature. An ethanol (300 ml) solution of Example 1A (5.00 g, 18.3 mmol) and additional piperidine (0.156 g, 1.83 mmol) is added, and the reaction mixture is stirred at reflux for 16 hours. The reaction mixture is concentrated in vacuo and chromatographed over silica get with cyclohexane/ethyl acetate mixtures to give a pale yellow oil.

Yield: 4.55 g (42.8% of th.) HPLC (method 5): $R_t$=4.59 min $^1$H-NMR (300 MHz, DMSO-$d_6$): δ=7.84–7.47 (m, 8H); 4.97 (s, 1H); 4.18 (q, 2H); 4.02 (q, 2H); 1.92 (s, 3H); 1.11 (t, 3H); 1.10 (t, 3H) ppm.

Example 18A

4-[(2,2-Dimethyl-4,6-dioxo-1,3-dioxan-5-ylidene)methyl]benzonitrile

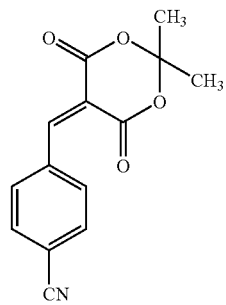

4-Cyanobenzaldehyde (5.30 g, 50.0 mmol) and 2,2-dimethyl-1,3-dioxane-4,6-dione (7.93 g, 55.0 mmol) are stirred in water (100 ml) at 75° C. in analogy to the described procedure of Bigi et al. [*Tetrahedron Lett.*, 2001, 42, 5203–5205]. The precipitate is filtered and recrystallised from ethanol.

Yield: 3.04 g (24% of th.) Mp.: 180° C. (with decomposition) MS (DCI, NH$_3$): m/z=275 [M+NH$_4$]$^+$ $^1$H-NMR (200 MHz, DMSO-$d_6$): δ=8.45 (s, 1H1); 8.03 (d, 2H); 7.95 (d, 2H); 1.78 (s, 6H) ppm.

Example 19A

Dimethyl 2-(4-cyanobenzylidene)malonate

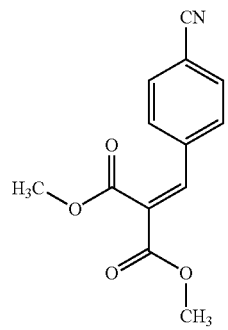

Dimethyl malonate (5.04 g, 38.13 mmol), 4-cyanobenzaldehyde (5.00 g, 38.13 mmol) and piperidine (0.097 g, 1.1 mmol) are dissolved in methanol (150 ml). The reaction mixture is stirred for two days (48 hours) at room temperature. The solvent is removed in vacuo to afford a viscous oil which is recrystallised from methanol.

Yield: 5.3 g (57% of th.) Mp.: 98–99° C. HPLC (method 5): $R_t$=3.94 min $^1$H-NMR (300 MHz, DMSO-$d_6$): δ=8.0–7.6 (m, 5H); 3.81 (s, 3H); 3.80 (s, 3H) ppm.

Example 20A

Diethyl 2-amino-4-(5-cyano-1-benzofuran-2-yl)-6-methyl-1-[3-(trifluoromethyl)-phenyl]-1,4-dihydro-3,5-pyridinedicarboxylate

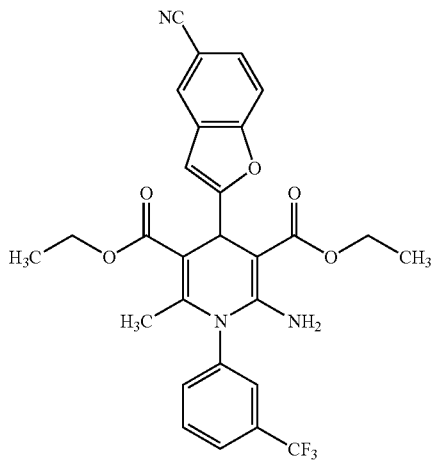

2-Formyl-1-benzofuran-5-carbonitrile (157 mg, 0.915 mmol) and ethyl cyanoacetate (103 mg, 0.915 mmol) are dissolved in ethanol (8 ml). Piperidine (2.3 mg, 0.027 mmol) is added, and the reaction mixture is stirred for two hours at room temperature. A solution of Example 1A (253 mg, 0.915 mmol) and piperidine (7.8 mg, 0.091 ml) in ethanol (2 ml) is added, and the reaction mixture is stirred at reflux (95° C.) overnight (18 h). The crude reaction mixture is concentrated in vacuo, dissolved in DMSO (7 ml) and purified by preparative HPLC.

Yield: 249 mg (50% of th.) LC-MS (method 2): $R_t$=5.34 min. MS (EI): m/z=540 $[M+H]^+$ $^1$H-NMR (200 MHz, DMSO-$d_6$): δ=8.11 (s, 1H); 7.99–7.64 (m, H); 6.87 (br.s, 2H); 6.63 (s, 1H); 4.25–3.92 (m, 4H); 1.98 (s, 3H); 1.31–1.09 (m, 6H) ppm.

The following compounds are prepared analogously as described for Example 7A:

| Ex.-No. | Starting material | Structure | Analytical data |
|---|---|---|---|
| 21A | Example 1A | (structure shown) | LC-MS (method 4): $R_t$ = 2.17 + 2.98 min. MS (EI): m/z = 511 $[M + H]^+$ |
| 22A | Example 1A | (structure shown) | LC-MS (method 4): $R_t$ = 2.26 + 2.92 min. MS (EI): m/z = 513 $[M + H]^+$ |

Example 23A

Ethyl 3-[(2-methoxyethyl)amino]-3-oxopropanoate

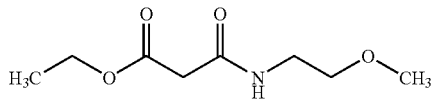

2.0 g (13.3 mmol) Ethyl 3-chloro-3-oxopropanoate are dissolved in 50 ml tetrahydrofuran and 2.99 g (39.85 mmol) 2-methoxyethylamine are added at 0° C. The reaction mixture is stirred at room temperature for 18 hours. The solvent is removed in vacuo and the product is isolated by column chromatography (silica, eluent dichloromethane/methanol 50:1).

Yield: 2.0 g (80% of th.) $^1$H-NMR (200 MHz, DMSO-d$_6$): δ=1.2 (t, 3H); 3.2 (m, 2H; s, 3H; s, 2H); 3.3 (m, 2H); 4.1 (q, 2H); 8.2 (br.t, 1H) ppm.

Example 24A

Ethyl 3-[(3-tert.-butoxy-3-oxopropyl)amino]-3-oxopropanoate

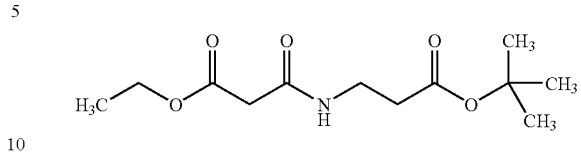

10 g (55.05 mmol) tert.-butyl β-alaninate hydrochloride are dissolved in 50 ml tetrahydrofuran, and 11.14 g (110.1 mmol) triethylamine and 5.53 g (36.7 mmol) ethyl 3-chloro-3-oxopropanoate are added at 0° C. The reaction mixture is stirred at room temperature for 18 hours. The solvent is removed in vacuo and the product is isolated by column chromatography (silica, eluent dichloromethane/methanol 100:1→50:1).

Yield: 7.25 g (76% of th.) $^1$H-NMR (200 MHz, DMSO-d$_6$): δ=1.2 (t, 3H); 1.4 (s, 9H); 2.3 (t, 2H); 3.2 (s, 2H); 3.3 (q, 2H); 4.1 (q, 2H); 8.2 (t, 1H) ppm.

The following compounds are prepared analogously as described for Example 24A:

| Ex.-No. | Starting material | Structure | Analytical data |
|---|---|---|---|
| 25A | tert.-butyl L-alaninate hydrochloride | 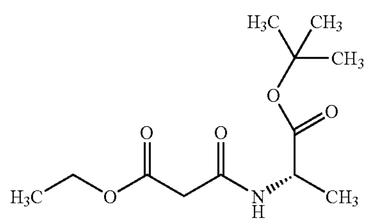 | LC-MS (method 2): R$_t$ = 4.04 min. MS (EI): m/z = 282 [M + Na]$^+$ |
| 26A | ethyl D,L-alaninate hydrochloride | 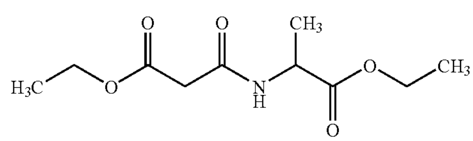 | LC-MS (method 4): R$_t$ = 2.50 min. MS (EI): m/z = 254 [M + Na]$^+$ |
| 27A | (1S)-1-phenylethyl-amine | 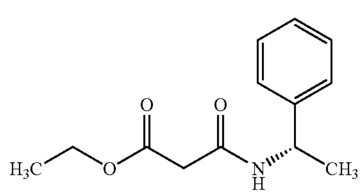 | LC-MS (method 4): R$_t$ = 2.98 min. MS (EI): m/z = 236 [M + H]$^+$ |
| 28A | (1R)-1-phenylethyl-amine | 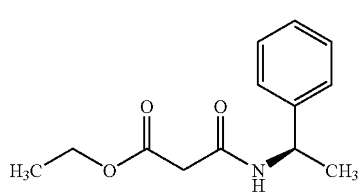 | LC-MS (method 7): R$_t$ = 3.82 min. MS (EI): m/z = 258 [M + Na]$^+$ |
| 29A | methylamine | 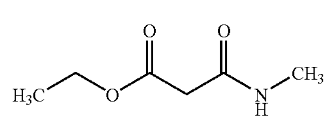 | LC-MS (method 6): R$_t$ = 2.25 min. MS (EI): m/z = 146 [M + H]$^+$ |

Example 30A 5-(Trifluoromethyl)-3-pyridinamine

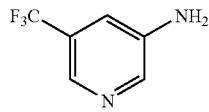

Prepared according to the method of Barlin et al., *Aust. J Chem.*, 1990, 43, 1175: 3-Chloro-5-(trifluoromethyl)pyridine (3.0 g, 16.52 mmol) is suspended in water (67.5 ml) and treated with copper(I)chloride (8.18 g, 82.62 mmol). Aqueous ammonia solution (25%, 67.5 ml) is added, and the reaction is stirred for 48 hours at 170° C. in the autoclave. The reaction mixture is cooled to room temperature and extracted three times with dichloromethane. The combined organic phases are washed with brine, dried with magnesium sulphate, filtered and concentrated in vacuo to yield analytically pure product.

Yield: 2.09 g (78% of th.) HPLC (method 8): $R_t$=1.73 min. MS (DCI): m/z=180 [M+NH$_4$]$^+$ $^1$H-NMR (200 MHz, DMSO-d$_6$): δ=5.85 (s, 2H); 7.16 (s, 1H); 8.02 (s, 1H); 8.17 (s, 1H) ppm.

Example 31A

Ethyl 3-oxo-3-{[5-(trifluoromethyl)-3-pyridinyl]amino}propanoate

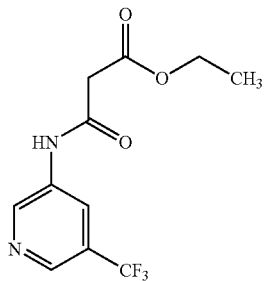

To a stirred solution of Example 30A (100 mg, 0.62 mmol) and triethylamine (75 mg, 0.74 mmol) at 0° C. in dichloromethane (5 ml) is added ethyl malonyl chloride (108 mg, 0.65 mmol) dropwise over 15 minutes. The solution is allowed to warm to room temperature, and stirring is continued overnight (18 h). The crude reaction solution is concentrated in vacuo and the residue is purified by preparative RP-HPLC (acetonitrile/water 1:9 to 9:1 gradient) to afford a colourless oil.

Yield: 144.4 mg (85% of th.) HPLC (method 5): $R_t$=3.80 min., $\lambda_{max}$ 196 nm, 244 nm MS (ESIpos): m/z=277 [M+H]$^+$ $^1$H-NMR (300 MHz, CDCl$_3$): δ=9.74 (s, 1H); 8.81 (s, 1H); 8.64 (s, 1H); 8.47 (s, 1H); 4.30 (q, 2H); 3.53 (s, 2H); 1.35 (t, 3H) ppm.

Example 32A

Ethyl (2Z)-2-acetyl-3-(4-cyanophenyl)-2-propenoate

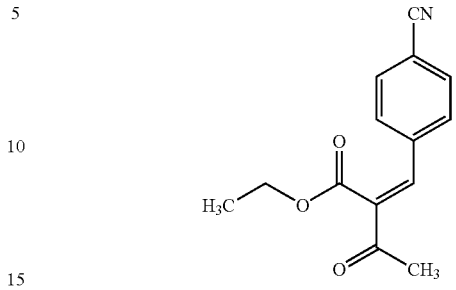

A solution of 4-cyanobenzaldehyde (2 g, 15.3 mmol), ethyl acetoacetate (1.98 g, 15.3 mmol), piperidine (65 mg, 0.76 mmol), and p-toluenesulfonic acid (131 mg, 0.76 mmol) in toluene (100 ml) is stirred under an argon atmosphere at reflux for 72 hours in a flask equipped with a Dean-Stark trap. The crude reaction mixture is concentrated in vacuo to afford an oil which is chromatographed over silica gel with cyclohexane/ethyl acetate 20:1 as eluent.

Yield: 1.12 g (30% of th.) HPLC (method 5): $R_t$=4.28 min., $\lambda_{max}$ 288 nm MS (ESIpos): m/z=261 [M+NH$_4$]$^+$ $^1$H-NMR (300 MHz, CDCl$_3$): δ=7.69 (d, 2H); 7.54 (d, 2H); 4.32 (q, 2H); 2.44 (s, 3H); 1.26 (t, 3H) ppm.

Example 33A

Diethyl 2-acetyl-3-(4-cyanophenyl)-4-({[5-(trifluoromethyl)-3-pyridinyl]amino}-carbonyl)pentanedioate

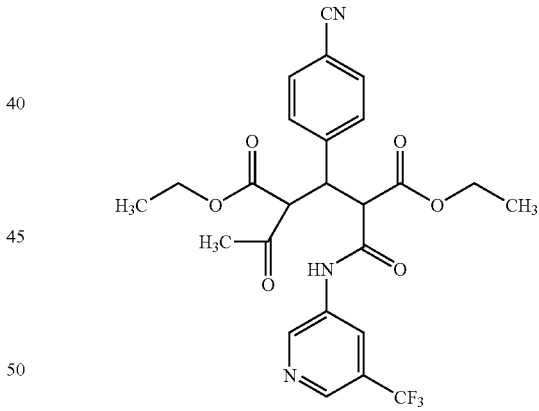

To a stirred solution of Example 31A (100 mg, 0.36 mmol) and Example 32A (80 mg, 0.36 mmol) in tetrahydrofuran (2 ml) is added tetrabutylammonium fluoride (0.182 ml of a 1 M solution in THF, 0.18 mmol) under an argon atmosphere. The reaction solution is stirred at room temperature for three hours, concentrated in vacuo and purified by preparative RP-HPLC using an acetonitrile/water (1:9 to 9:1) gradient.

Yield: 132 mg (61% of th.) as mixture of diastereomers HPLC (method 5): $R_t$=4.69 min., $\lambda_{max}$ 194 nm MS (ESIpos): m/z=520 [M+H]$^+$ $^1$H-NMR (300 MHz, DMSO-d$_6$): δ=10.94 (s, 1H, diastereomer A); 10.78 (d, 1H, diastereomer B); 8.94–8.04 (m, 3H); 7.87–7.35 (m, 4H); 4.54–3.68 (m, 7H); 2.24–1.94 (m, 3H); 1.34–0.76 (m, 6H) ppm.

Example 34A

Ethyl 3-oxo-3-{[3-(trifluoromethyl)phenyl]amino}propanoate

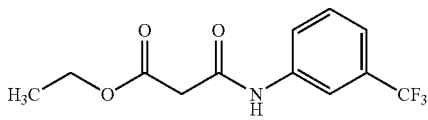

To a stirred solution of 3-trifluoromethylaniline (1.90 g, 11.8 mmol), triethylamine (1.43 g, 14.5 mmol ), and 4-N,N-dimethylaminopyridine (1 mg) in dichloromethane (20 ml) is added at 0° C. ethyl malonyl chloride (1.78 g, 11.8 mmol). The reaction mixture is warmed to room temperature overnight, then allowed to stand for two days. Water (20 ml) is added and the product is extracted with dichloromethane (1 l). The organic phase is washed with saturated ammonium chloride solution (500 ml) and saturated sodium chloride solution (200 ml), dried over magnesium sulphate monohydrate, filtered and concentrated. The crude product is chromatographed over silica gel with cyclohexane/ethyl acetate mixtures as eluent.

Yield: 3 g (92% of th.) HPLC (method 5): $R_t$=4.38 min. MS (ESIpos): m/z=276 [M+H]$^+$ $^1$H-NMR (200 MHz, CDCl$_3$): δ=9.55 (s, 1H); 7.86 (s, 1H); 7.77 (d, 1H); 7.52–7.32 (m, 2H); 4.37–4.16 (m, 2H); 3.51 (s, 21H); 1.34 (m, 3H) ppm.

Example 35A

Lithium 3-oxo-3-{[3-(trifluoromethyl)phenyl]amino}propanoate

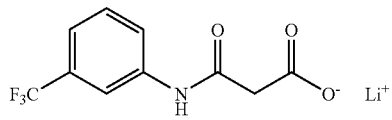

To a tetrahydrofuran (350 ml) solution of Example 34A (5 g, 18.17 mmol) is added lithium hydroxide (435 mg, 18.17 mmol) in water (150 ml). The solution is stirred at room temperature for 4 hours, and then concentrated to afford a white solid. The product is used without further purification.

Yield: 4.62 g (99% of th.) HPLC (method 5): $R_t$=3.88 min., $λ_{max}$ 202 nm MS (ESIpos): m/z=254 [M+H]$^+$ $^1$H-NMR (300 MHz, DMSO): δ=12.84 (s, 1H); 8.10 (s, 1H); 7.66 (d, 1H); 7.51 (t, 1H); 7.33 (d, 1H); 2.90 (s, 2H) ppm.

Example 36A

3-Oxo-3-(1-pyrrolidinyl)-N-[3-(trifluoromethyl)phenyl]propanamide

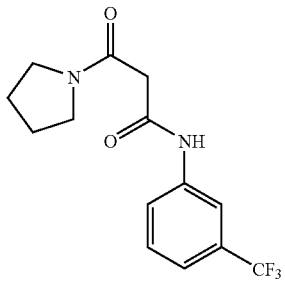

A solution of Example 35A (200 mg, 0.79 mmol), pyrrolidine (62 mg, 0.869 mmol), ethyldiisopropylamine (224 mg, 1.7 mmol), 1-hydroxy-1H-benzotriazol hydrate (129 mg, 0.95 mmol), 4-N,N-dimethylaminopyridine (1 mg), and 1-ethyl-3-(3-(dimethylamino)propyl)carbodiimide hydrochloride (197 mg, 1.03 mmol) in dimethyl formamide (8 ml) is stirred at room temperature overnight (18 h). The crude reaction mixture is purified directly by preparative RP-HPLC to afford a yellow solid.

Yield: 159 mg (67% of th.) HPLC (method 5): $R_t$=4.10 min. MS (ESIpos): m/z=301 [M+H]$^+$ $^1$H-NMR (300 MHz, CDCl$_3$): δ=10.81 (s, 1H); 7.90 (s, 1H); 7.78 (d, 1H); 7.42 (t, 1H); 7.34 (d, 1H); 3.53 (q, 4H); 3.41 (s, 2H); 2.09–1.87 (m, 4H) ppm.

Example 37A

Ethyl 2-acetyl-3-(4-cyanophenyl)-5-oxo-5-(1-pyrrolidinyl)-4-({[3-(trifluoromethyl)-phenyl]amino}carbonyl)pentanoate

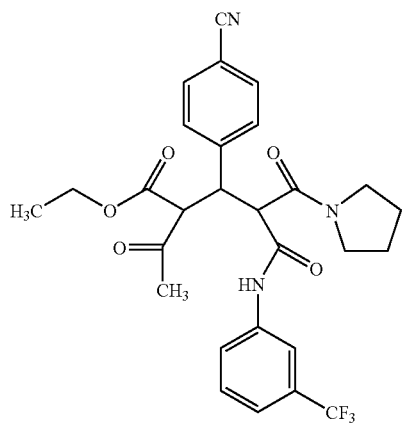

Prepared according to the procedure described in Example 33A from Example 36A (100 mg, 0.33 mmol) and Example 32A (81 mg, 0.33 mmol).

Yield: 143 mg (60% of th.) HPLC (method 5): $R_t$=4.84 min., $λ_{max}$ 200 nm MS (ESIpos): m/z=544 [M+H]$^+$.

Example 38A

N¹-(2-Methoxyethyl)-N¹-methyl-N³-[3-(trifluoromethyl)phenyl]malonamide

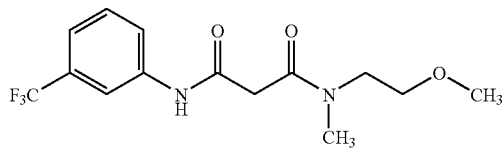

Prepared according to the procedure described in Example 36A from (2-methoxyethyl)methyl amine (77 mg, 0.87 mmol) and Example 35A (200 mg, 0.79 mmol).

Yield: 179 mg (79% of th.) HPLC (method 5): $R_t$=4.0 min., $\lambda_{max}$ 202 nm MS (ESIpos): m/z=319 [M+H]⁺ ¹H-NMR (300 MHz, CDCl₃): δ=10.70 (s, 0.5H, NH, rotamer 1); 10.55 (s, 0.5H, NH, rotamer 2); 7.88 (s, 1H); 7.79 (d, 1H); 7.42 (t, 1H); 7.34 (d, 1H); 3.67–3.44 (m, 6H); 3.37–3.31 (m, 3H); 3.15 (s, 1.5H, rotamer); 3.15 (s, 1.5H, rotamer) ppm.

Example 39A

Ethyl 2-acetyl-3-(4-cyanophenyl)-5-[(2-methoxyethyl)(methyl)amino]-5-oxo-4-({[3-(trifluoromethyl)phenyl]amino}carbonyl)pentanoate

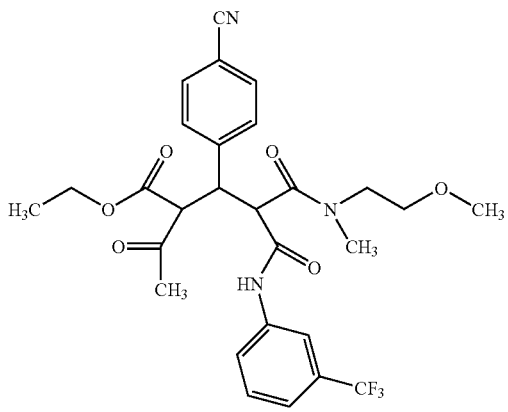

Prepared according to the procedure described in Example 33A from Example 38A (100 mg, 0.314 mmol) and Example 32A (76 mg, 0.314 mmol).

Yield: 122.8 mg (49% of th.) as mixture of diastereomers HPLC (method 5): $R_t$=4.81 min., $\lambda_{max}$ 198 nm MS (ESIpos): m/z=562 [M+H]⁺.

Example 40A

N¹,N¹-Diethyl-N³-[3-(trifluoromethyl)phenyl]malonamide

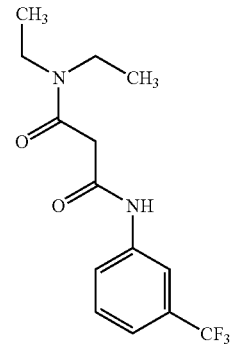

Prepared according to the procedure described in Example 36A from diethylamine (64 mg, 0.87 mmol) and Example 35A (200 mg, 0.79 mmol).

Yield: 82 mg (34% of th.) HPLC (method 5): $R_t$=4.29 min., $\lambda_{max}$ 202 nm MS (ESIpos): m/z=303 [M+H]⁺ ¹H-NMR (300 MHz, CDCl₃): δ=10.67 (s, 1H); 7.89 (s, 1H); 7.78 (d, 1H); 7.42 (t, 1H); 7.34 (d, 1H); 3.53–3.34 (m, 6H); 1.25 (t, 3H); 1.18 (t, 3H) ppm.

Example 41A

Ethyl 2-acetyl-3-(4-cyanophenyl)-5-(diethylamino)-5-oxo-4-({[3-(trifluoromethyl)-phenyl]amino}carbonyl)pentanoate

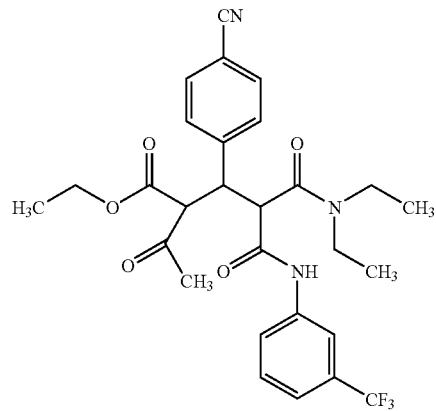

Prepared according to the procedure described in Example 33A from Example 40A (150 mg, 0.496 mmol) and Example 32A (120 mg, 0.496 mmol).

Yield: 163 mg (43% of th.) HPLC (method 5): $R_t$=5.04 min., $\lambda_{max}$ 198 nm MS (ESIpos): m/z=568 [M+Na]⁺.

Example 42A 3-(4-Morpholinyl)-3-oxo-N-[3-(trifluoromethyl)phenyl]propanamide

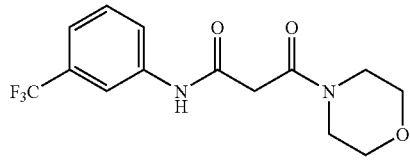

Prepared according to the procedure described in Example 36A from morpholine (75 mg, 0.87 mmol) and Example 35A (200 mg, 0.79 mmol).

Yield: 82 mg (33% of th.) HPLC (method 5): $R_t$=3.92 min., $\lambda_{max}$ 202 nm MS (ESIpos): m/z=317 [M+H]$^+$ $^1$H-NMR (200 MHz, CDCl$_3$): δ=10.29 (s, 1H); 7.88 (s, 1H); 7.77 (d, 1H); 7.50–7.31 (m, 2H); 3.78–3.57 (m, 8H); 3.48 (s, 2H) ppm.

Example 43A

Ethyl 2-acetyl-3-(4-cyanophenyl)-5-(4-morpholinyl)-5-oxo-4-({[3-(trifluoromethyl)-phenyl]amino}carbonyl)pentanoate

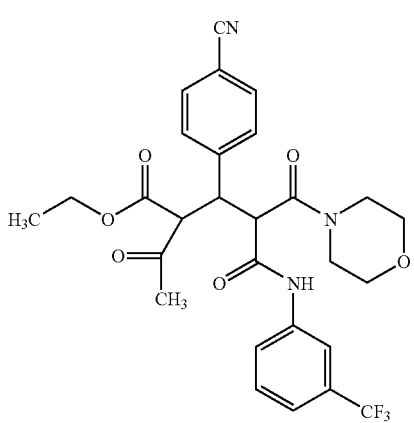

Prepared according to the procedure described in Example 33A from Example 42A (150 mg, 0.474 mmol) and Example 32A (115 mg, 0.474 mmol).

Yield: 145 mg (54% of th.) HPLC (method 5): $R_t$=4.72 min., $\lambda_{max}$ 198 nm MS (ESIpos): m/z=560 [M+H]$^+$.

Example 44A

3-Oxo-3-(1,3-thiazolidin-3-yl)-N-[3-(trifluoromethyl)phenyl]propanamide

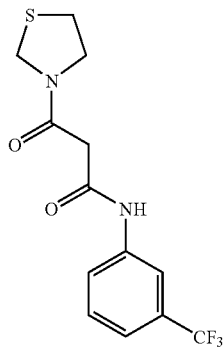

Prepared according to the procedure described in Example 36A from thiazolidine hydrochloride (273 mg, 2.173 mmol) and Example 35A (500 mg, 1.975 mmol).

Yield: 457 mg (73% of th.) HPLC (method 5): $R_t$=4.16 min., $\lambda_{max}$ 202 nm MS (ESIpos): m/z=319 [M+H]$^+$.

Example 45A

Ethyl 2-acetyl-3-(4-cyanophenyl)-5-oxo-5-(1,3-thiazolidin-3-yl)-4-({[3-(trifluoromethyl)phenyl]amino}carbonyl)pentanoate

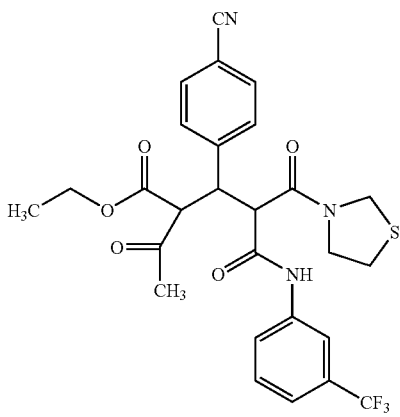

Prepared according to the procedure described in Example 33A from Example 44A (200 mg, 0.628 mmol) and Example 32A (153 mg, 0.628 mmol).

Yield: 196 mg (55% of th.) HPLC (method 9): $R_t$=4.84 min., $\lambda_{max}$ 200 nm MS (ESIpos): m/z=560 [M+H]$^+$.

Example 46A

Ethyl 3-(4-methyl-1-piperazinyl)-3-oxopropanoate

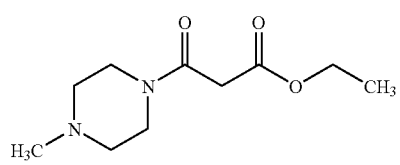

Prepared according to the procedure described in Example 31A from 1-methyl-piperazine (2.0 g, 20 mmol).

Yield: 3.19g (75% of th.) HPLC (method 5): $R_t$=1.24 min., $\lambda_{max}$ 198 nm MS (ESIpos): m/z=215 [M+H]$^+$.

Example 47A

Lithium 3-(4-methyl-1-piperazinyl)-3-oxopropanoate

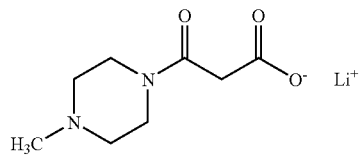

Example 46A (1.0 g, 4.7 mmol) is dissolved in 50 ml tetrahydrofuran, and lithium hydroxide (112 mg, 4.7 mmol) dissolved in 30 ml water is added dropwise. The reaction mixture is stirred at room temperature for 4 h. The mixture is diluted with 30 ml water and most of the tetrahydrofuran is removed in vacuo. The aqueous mixture is washed three times with 50 ml of ethyl acetate. The aqueous layer is evaporated to dryness in vacuo, and the crude product is stirred with 100 ml dichloromethane/30 ml ethyl acetate at 35° C. for 20 minutes. The precipitate is filtered and dried in vacuo.

Yield: 0.76g (84% of th.) HPLC (method 10): $R_t$=1.85 min., $\lambda_{max}$ 198 nm MS (ESIpos): m/z=193 [M+H]$^+$.

Example 48A 3-(4-Methyl-1-piperazinyl)-3-oxo-N-[3-(trifluoromethyl)phenyl]propanamide

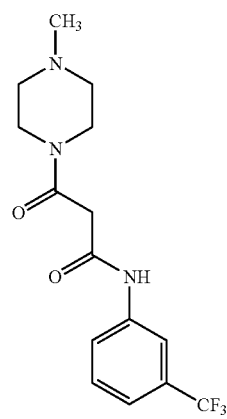

A solution of Example 47A (700 mg, 3.64 mmol), 3-trifluoromethylaniline (646 mg, 4.01 mmol), ethyldiisopropylamine (1036 mg, 8.01 mmol), 1-hydroxy-1H-benzotriazol hydrate (591 mg, 4.37 mmol), and 1-ethyl-3-(3-(dimethylamino)propyl)carbodiimide hydrochloride (908 mg, 4.74 mmol) in dimethyl formamide (30 ml) is stirred at room temperature overnight (18 h). The solvent is removed in vacuo and the residue is dissolved in 300 ml water/ethyl acetate. The phases are separated and the aqueous phase is extracted three times with ethyl acetate. The organic layers are combined, washed with brine, and the solvent is removed in vacuo. The crude product is purified by flash chromatography over silica gel with cyclohexane/ethyl acetate as eluent. The resulting product is further purified by preparative HPLC (acetonitrile/water 1:9 to 9:1 gradient) to afford a pale yellow solid.

Yield: 305 mg (25% of th.) HPLC (method 5): $R_t$=3.73 min., $\lambda_{max}$ 202 nm MS (ESIpos): m/z=330 [M+H]$^+$ $^1$H-NMR (300 MHz, DMSO-d$_6$): δ=2.2 (s, 3H); 2.27 (t, 2H); 2.33 (t, 2H); 3.47 (t, 4H); 3.54 (s, 2H); 7.40 (d, 1H); 7.55 (t, 1H); 7.74 (d, 1H); 8.08 (s, 1H); 10.41 (s, 1H) ppm.

Example 49A

Ethyl 2-acetyl-3-(4-cyanophenyl)-5-(4-methyl-1-piperazinyl)-5-oxo-4-({[3-(trifluoromethyl)phenyl]amino}carbonyl)pentanoate

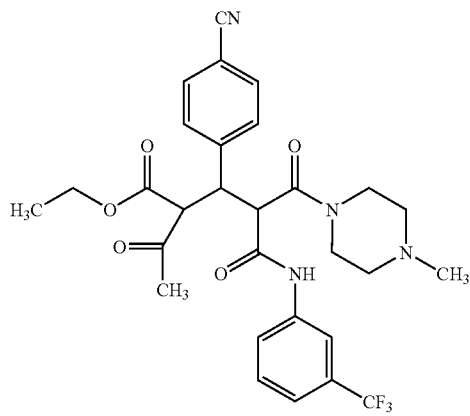

Prepared according to the procedure described in Example 33A from Example 48A (135 mg, 0.410 mmol) and Example 32A (100 mg, 0.410 mmol).

Yield: 190 mg (81% of th.) HPLC (method 7): $R_t$=2.91+2.94 min. MS (ESIpos): m/z=573 [M+H]$^+$.

Example 50A

5-Methyl-2-pyridinecarbonitrile

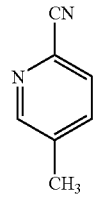

36 g (209 mmol) 2-Bromo-5-methylpyridine and 37.5 g (418 mmol) copper cyanide are refluxed for two hours in 500 ml dimethylformamide. After cooling down to 50° C., 10% aqueous armnoia solution (500 ml) is added with stirring. The product is extracted with dichloromethane, the organic phase is dried over magnesium sulfate, and the solvent is removed in vacuo. The product is purified by column chromatography (silica, eluent cyclohexane/ethyl acetate 9:1).

Yield: 18 g (73% of th.) $^1$H-NMR (300 MHz, CDCl$_3$): δ=2.4 (s, 3H); 7.6 (m, 2H); 8.6 (s, 1H) ppm.

Example 51A 5-(Hydroxymethyl)-2-pyridinecarbonitrile

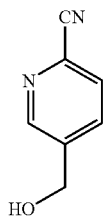

Example 50A (13 g, 110 mmol) is dissolved in 400 ml tetrachloromethane, and 29.4 g (165 mmol) N-bromosuccinimide and 0.4 g (1.6 mmol) dibenzoylperoxide are added. The reaction mixture is refluxed for three hours, cooled down to room temperature and filtered. The solution is washed with aqueous sodium thiosulfate, dried over magnesium sulfate and the solvent is removed in vacuo. The residue is dissolved in 200 ml dioxane and 200 ml water, calciumcarbonate (44 g, 440 mmol) is added and the mixture is stirred at reflux for 2 hours. After cooling down to room temperature, the mixture is filtered and dichloromethane is added. After phase separation, the organic phase is dried over magnesium sulfate and the solvent is removed in vacuo. The product is purified by chromatography (silica, eluent cyclohexane/ethyl acetate 2:1).

Yield: 5.2 g (35% of th.) $^1$H-NMR (300 MHz, DMSO-d$_6$): δ=4.7 (d, 2H); 5.6 (t, 1H); 8.0 (m, 2H); 8.7 (s, 1H) ppm.

Example 52A

5-Formyl-2-pyridinecarbonitrile

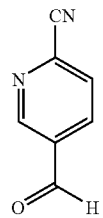

1.04 g (8.2 mmol) oxalylchloride are dissolved in 8 ml dichloromethane. At −78° C., 1.28 g (16.4 mmol) dimethylsulfoxide are added dropwise. The solution is stirred at −78° C. for 20 minutes, then 1 g (7.46 mmol) of Example 51A, dissolved in 7 ml dichloromethane, is added, and stirring at −78° C. is continued for another 2 hours. 3.4 g (33.6 mmol) triethylamine are then added dropwise, and after warming up to room temperature, the mixture is purified by column chromatography (silica, eluent cyclohexane to cyclohexane/ethyl acetate 2:1).

Yield: 0.76 g (77% of th.) Mp.: 80–82° C. HPLC (method 4): R$_t$=2.13 min. MS (ESIpos): m/z=133 [M+H]$^+$ $^1$H-NMR (400 MHz, DMSO-d$_6$): δ=10.18 (s, 1H); 9.21 (m, 1H); 8.49 (m, 1H); 8.27 (m, 1H) ppm.

Example 53A

Allyl 2-acetyl-3-(4-cyanophenyl)-5-oxo-5-{[3-(trifluoromethyl)phenyl]amino}-pentanoate

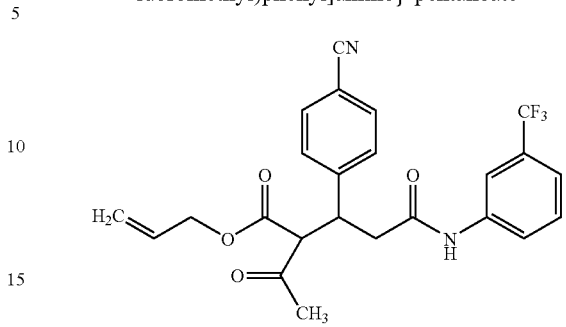

To a solution of 4-formylbenzonitrile (10.00 g, 76.3 mmol), allyl 3-oxobutanoate (10.84 g, 76.3 mmol), 2,2-dimethyl-1,3-dioxane-4,6-dione (10.99 g, 76.3 mmol) and 3-(trifluoromethyl)aniline (12.29 g, 76.3 mmol) in 150 ml THF are added 4.00 g potassium fluoride on alumina (40 wt.-%). The reaction mixture is stirred at reflux temperature overnight. The solvent is removed in vacuo, the residue is dissolved in methylene chloride and then purified by column chromatography using a methylene chloride/ethyl acetate gradient as eluent.

Yield: 12.60 g (36% of th.) LC-MS (method 8): R$_t$=4.02 min. MS (EI): m/z=459 [M+H]$^+$.

Example 54A

Ethyl 4-(4-chlorophenyl)-2-methyl-6-oxo-1-[3-(trifluoromethyl)phenyl]-1,4,5,6-tetrahydro-3-pyridinecarboxylate

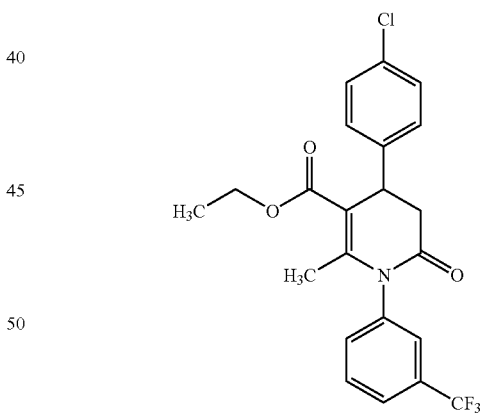

Example 1A (136 mg, 0.5 mmol) is dissolved in 1 ml toluene, pyridine (47mg, 0.6 mmol) is added, and the reaction mixture is heated to reflux. At this temperature, (2E)-3-(4-chlorophenyl)-2-propenoyl chloride (100 mg, 0.5 mmol), dissolved in 1 ml toluene, is added dropwise. The mixture is refluxed for 2 h and then stored for 60 hours at +4° C. The solvent is removed in vacuo, and the residue is purified by preparative HPLC to afford an amorphous colourless solid.

Yield: 67 mg (31% of th.) LC-MS (method 7): R$_t$=4.11 min. $^1$H-NMR (200 MHz, DMSO-d$_6$): δ=1.22 (t, 3H); 2.13 (s, 3H); 2.93 (dd, 1H); 3.13 (dd, 1H); 4.17 (q, 2H); 4.32–4.39 (m, 1H); 7.17–7.69 (m, 8H) ppm.

The following compounds are prepared analogously as described for Example 24A:

| Ex.-No. | Starting material | Structure | Analytical data |
|---|---|---|---|
| 55A | 2-morpholin-4-yl-ethylamine | 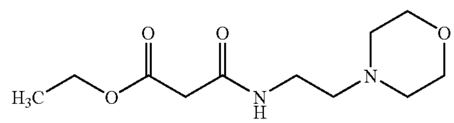 | HPLC (method 5): $R_t$ = 2.0 min. MS (DCI): m/z = 245 $[M + H]^+$ |
| 56A | 3-methoxy-propylamine | 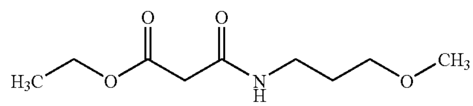 | HPLC (method 5): $R_t$ = 2.89 min. MS (DCI): m/z = 204 $[M + H]^+$ |
| 57A | sec.-butylamine | 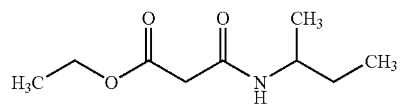 | LC-MS (method 8): $R_t$ = 2.35 min. MS (EI): m/z = 188 $[M + H]^+$ |
| 58A | butylamine | 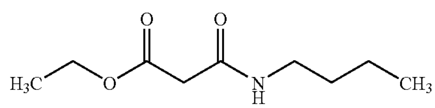 | LC-MS (method 8): $R_t$ = 2.42 min. MS (EI): m/z = 188 $[M + H]^+$ |
| 59A | isobutylamine | 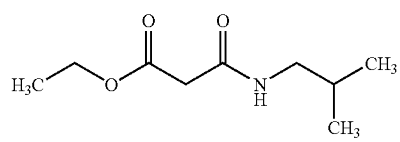 | LC-MS (method 8): $R_t$ = 2.45 min. MS (EI): m/z = 188 $[M + H]^+$ |
| 60A | $N^1,N^1$-dimethyl-ethane-1,2-diamine | 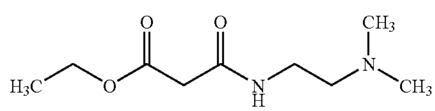 | LC-MS (method 2): $R_t$ = 0.57 min. MS (EI): m/z = 203 $[M + H]^+$ |
| 61A | 2-(tert.-butyl-dimethyl-silanyloxy)-ethylamine | 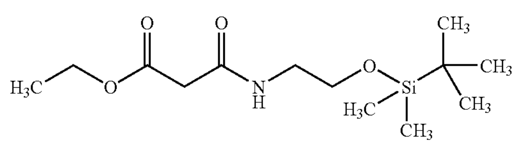 | LC-MS (method 8): $R_t$ = 3.63 min. MS (EI): m/z = 290 $[M + H]^+$ |
| 62A | aminoacetic acid tert.-butyl ester | 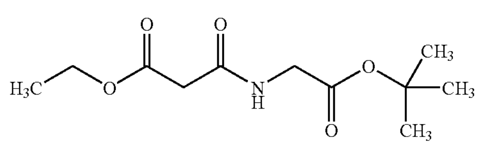 | LC-MS (method 7): $R_t$ = 2.93 min. MS (EI): m/z = 268 $[M + Na]^+$ |

Example 63A

3-{[3-Methylphenyl]amino}-2-butenenitrile

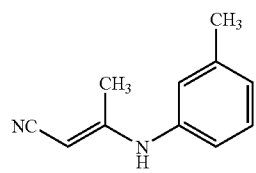

3-Aminocrotonitrile (5.0 g, 60.9 mmol), 3-methylaniline (7.18 g, 66.99 mmol) and acetic acid (6.22 g, 103.5 mmol) are dissolved in water (20 ml). The reaction mixture is stirred at room temperature for 60 minutes and the precipitate is isolated.

Yield: 5.03 g (48% of th.) $^1$H-NMR (300 MHz, DMSO-$d_6$): δ=2.1 (s, 3H); 2.3 (s, 3H); 4.4 (s, 1H); 6.9 (m, 3H); 7.2 (m, 1H); 8.7 (s, 1H) ppm.

Example 64A

3-{[3-Chlorophenyl]amino}-2-butenenitrile

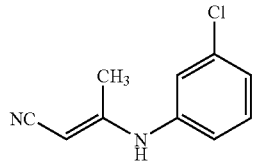

3-Aminocrotonitrile (5.0 g, 60.9 mmol), 3-chloroaniline (8.55 g, 66.99 mmol) and acetic acid (6.22 g, 103.5 mmol) are dissolved in water (20 ml). The reaction mixture is stirred at room temperature for 60 minutes and the precipitate is isolated.

Yield: 3.92 g (33% of th.) $^1$H-NMR (200 MHz, DMSO-$d_6$): δ=2.1 (s, 3H); 4.6 (s, 1H); 7.1 (m, 3H); 7.4 (m, 1H); 8.9 (s, 1H) ppm.

PREPARATION EXAMPLES

Example 1

Diethyl 4-(4-cyanophenyl)-6-methyl-2-oxo-1-[3-(trifluoromethylphenyl]-1,2,3,4-tetrahydro-3,5-pyridinedicarboxylate

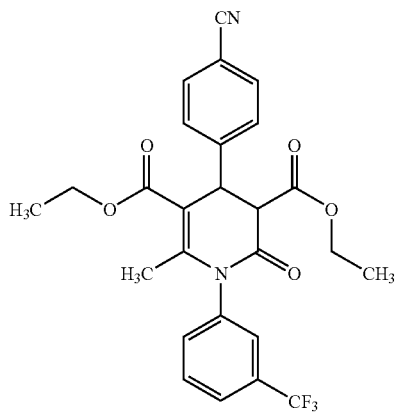

The compound of Example 1A (65% pure, 1.8 g, 4.3 mmol), 1,8-diazabicyclo[5.4.0]-undec-7-ene (0.065 g, 0.43 mmol) and the compound of Example 19A (1.05 g, 4.3 mmol) are dissolved in ethanol (200 ml) and stirred at reflux for 48 hours. The reaction is cooled to room temperature and the ethanol is removed in vacuo. The residue is chromatographed over silica gel with cyclohexane/ethyl acetate mixtures as eluent.

Yield: 0.4 g (14% of th.) HPLC (method 5): $R_t$=5.12 min. MS (ESIneg): m/z=499 [M–H]$^+$ $^1$H-NMR (300 MHz, DMSO-$d_6$): δ=7.9–7.5 (m, 8H); 4.75 (d, 1H); 4.01 (d, 1H); 4.30–3.95 (m, 4H); 2.09 (d, 3H); 1.27–1.05 (m, 6H) ppm.

Example 2

(+)-Diethyl 4-(4-cyanophenyl)-6-methyl-2-oxo-1-[3-(trifluoromethyl)phenyl]-1,2,3,4-tetrahydro-3,5-pyridinedicarboxylate

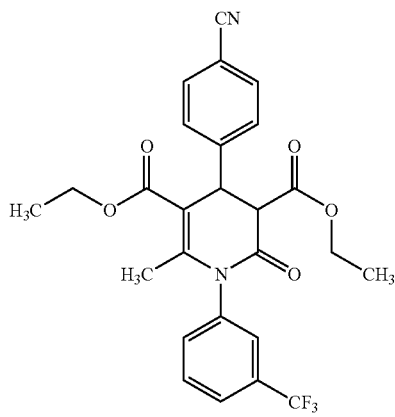

The compound of Example 1 is separated into the enantiomers via HPLC on a chiral stationary KBD 7644 silica gel column (silane-modified N-methacryloyl-D-valine-3-pentylamide fixed on silica, cf. EP-A-379 917) with an eluent mixture of i-hexane and ethyl acetate (1:4 v/v).

(+)-Enantiomer:
Yield: 0.4 g (14% of th.) HPLC (method 5): $R_t$=5.12 min [α]$^{20}_D$=+23° (0.7 M in dichloromethane) MS (ESIneg): m/z=499 [M–H]$^+$

Example 3

Ethyl 5-(aminocarbonyl)-4-(4-cyanophenyl)-2-methyl-6-oxo-1-[3-trifluoromethyl)-phenyl]-1,4,5,6-tetrahydro-3-pyridinecarboxylate

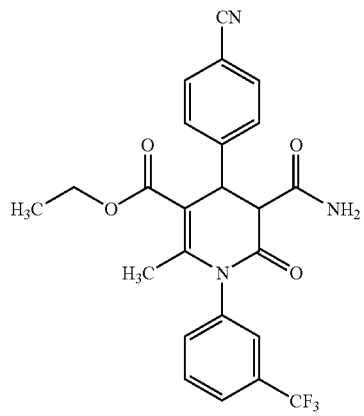

Example 10A (1 g, 2.13 mmol) is dissolved in acetic acid (20 ml) and water (1 ml). The mixture is stirred at reflux for 18 hours. After cooling to room temperature, the solvent is removed in vacuo and the residue is purified by column chromatography on silica with cyclohexane/ethyl acetate mixtures as eluent.

Yield: 0.27 g (27% of th.) $^1$H-NMR (300 MHz, DMSO-$d_6$): δ=1.1 (t, 3H); 2.1 (s, 3H); 3.6 (d, 1H); 4.1 (q, 2H); 4.7 (d, 1H); 7.4 (m, 1H); 7.6 (m, 2H); 7.7 (m, 2H); 7.8 (m, 1H); 7.9 (m, 4H) ppm.

Example 4

Ethyl 5-acetyl-4-(4-cyanophenyl)-6-methyl-2-oxo-1-[3-(trifluoromethyl)phenyl]-1,2,3,4-tetrahydro-3-pyridinecarboxylate

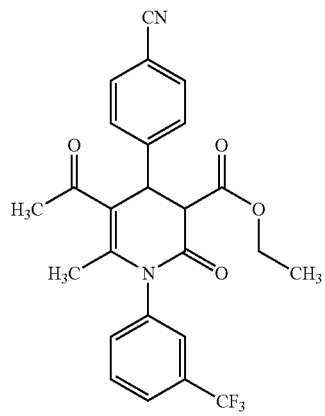

Example 6A (100 mg, 0.21 mmol) is dissolved in acetic acid (2 ml) and water (0.2 ml). The mixture is stirred at reflux for 18 hours. After cooling to room temperature, the solvent is removed in vacuo and the residue is purified by column chromatography on silica with cyclohexane/ethyl acetate mixtures as eluent.

Yield: 11 mg (11% of th.) $^1$H-NMR (200 MHz, DMSO-$d_6$): δ=1.2 (t, 3H); 2.0 (s, 3H); 2.2 (s, 3H); 4.1 (d, 1H); 4.2 (q, 2H); 4.8 (d, 1H); 7.5 (m, 2H); 7.6 (m, 1H); 7.7 (m, 2H); 7.8 (m, 5H) ppm.

Example 5

Ethyl 4-(4-cyanophenyl)-5-[(dimethylamino)carbonyl]-2-methyl-6-oxo-1-[3-(trifluoromethyl)phenyl]-1,4,5,6-tetrahydro-3-pyridinecarboxylate

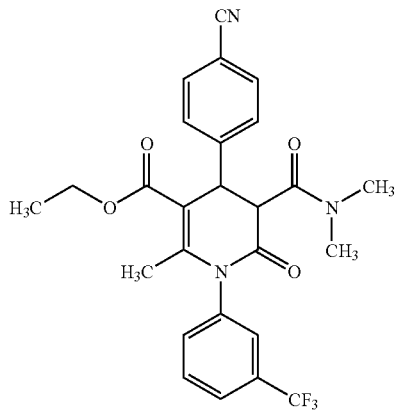

Example 13A (190 mg, 0.38 mmol) is dissolved in acetic acid (2 ml) and water (0.2 ml). The mixture is stirred at reflux for 18 hours. After cooling to room temperature, the solvent is removed in vacuo and the residue is purified by column chromatography on silica with cyclohexane/ethyl acetate mixtures as eluent.

Yield: 36 mg (19% of th.) $^1$H-NMR (300 MHz, DMSO-$d_6$): δ=1.0 (t, 3H); 2.0 (s, 3H); 2.8 (s, 3H); 3.1 (s, 3H); 4.0 (q, 2H); 4.2 (d, 1H); 4.5 (d, 1H); 7.6 (m, 4H); 7.7 (m, 1H); 7.8 (m, 3H) ppm.

Example 6

Ethyl 5-cyano-4-(4-cyanophenyl)-2-methyl-6-oxo-1-[3-(trifluoromethyl)phenyl]-1,4,5,6-tetrahydro-3-pyridinecarboxylate

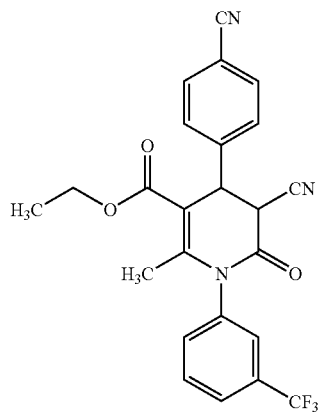

Example 15A (35 mg, 0.08 mmol) is dissolved in acetic acid (2 ml) and water (0.2 ml). The mixture is stirred at reflux for 18 hours. After cooling to room temperature, the solvent is removed in vacuo and the residue is purified by column chromatography on silica with dichloromethane as the eluent.

Yield: 11 mg (32% of th.) $^1$H-NMR (300 MHz, DMSO-$d_6$): δ=1.1 (t, 3H); 2.1 (s, 3H); 4.1 (m, 2H); 4.7 (d, 1H); 5.2 (br.m, 1H); 7.6 (m, 2H); 7.7 (m, 2H); 7.9 (m, 4H) ppm.

Example 7

5-Cyano-4-(4-cyanophenyl)-6-methyl-2-oxo-1-[3-(trifluoromethyl)phenyl]-1,2,3,4-tetrahydro-3-pyridinecarboxamide

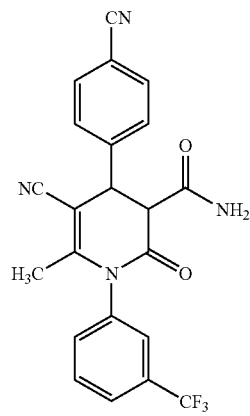

Example 9A (49 mg, 0.12 mmol) is dissolved in acetic acid (3 ml) and water (0.3 ml). The mixture is stirred at reflux for 18 hours. After cooling to room temperature, the solvent is removed in vacuo and the residue is purified by preparative HPLC.

Yield: 34 mg (69% of th.) $^1$H-NMR (300 MHz, DMSO-$d_6$): δ=1.9 (s, 3H); 3.9 (d, 1H); 4.5 (d, 1H); 7.3 (s, 1H); 7.6 (m, 3H); 7.7 (m, 3H); 7.8 (m, 1H); 7.9 (m, 2H) ppm.

Example 8

3-Ethyl 5-[(1R)-2-methoxy-1-methyl-2-oxoethyl]4-(4-cyanophenyl)-6-methyl-2-oxo-1-[3-(trifluoromethyl)phenyl]-1,2,3,4-tetrahydro-3,5-pyridinedicarboxylate

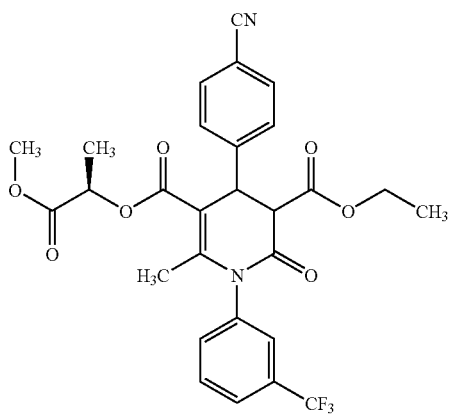

Example 14A (50 mg, 0.09 mmol) is dissolved in acetic acid (2 ml) and water (0.2 ml). The mixture is stirred at reflux for 18 hours. After cooling to room temperature, the solvent is removed in vacuo and the residue is purified by preparative HPLC.

Yield: 9 mg (18% of th.) as a mixture of diastereoisomers
¹H-NMR (300 MHz, DMSO-d₆): δ=1.2 (t, 3H, t, 3H, d, 3H); 1.4 (d, 3H); 2.1 (s, 3H, s, 3H); 3.6 (s, 3H); 3.7 (s, 3H); 4.1 (d, 1H); 4.2 (d, 1H); 4.3 (m, 4H); 4.8 (d, 1H, d, 1H; 5.0 (q, 1H); 5.1 (q, 1H); 7.5 (m, 4H); 7.6 (m, 4H); 7.8 (m, 2H); 7.9 (m, 6H) ppm.

Example 9

(2R)-2-[({4-(4-Cyanophenyl)-5-(ethoxycarbonyl)-2-methyl-6-oxo-1-[3-(trifluoromethyl)phenyl]-1,4,5,6-tetrahydro-3-pyridinyl}carbonyl)oxy]propanoic acid

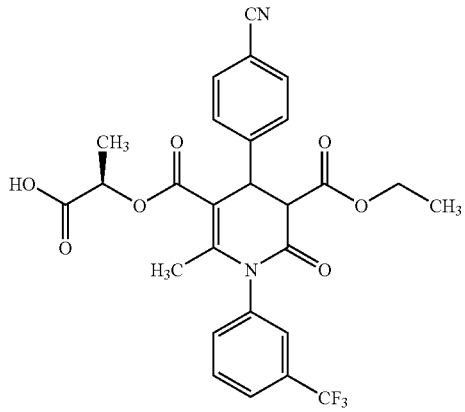

This compound is obtained as a by-product of the preparation of Example 8.

Yield: 7 mg (14% of th.) as a mixture of diastereoisomers
¹H-NMR (300 MHz, DMSO-d₆): δ=1.2 (t, 3H, t, 3H, d, 3H); 1.4 (d, 3H); 2.0 (s, 3H, s, 3H); 4.1 (d, 1H); 4.1 (d, 1H); 4.3 (m, 4H); 4.8 (d, 1H, d, 1H); 4.9 (q, 1H); 4.9 (q, 1H); 7.5 (m, 4H); 7.6 (m, 4H);, 7.8 (m, 2H); 7.9 (m, 6H) ppm.

Example 10

Ethyl 5-cyano-4-(4-cyanophenyl)-6-methyl-2-oxo-1-[3-(trifluoromethyl)phenyl]-1,2,3,4-tetrahydro-3-pyridinecarboxylate

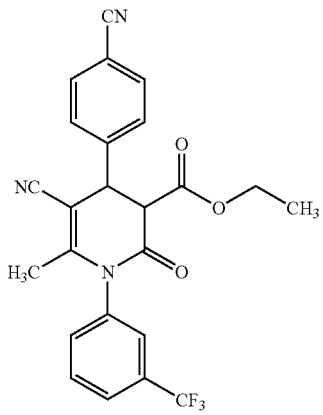

Example 11A (233 mg, 0.51 mmol) is dissolved in glacial acetic acid (5 ml) and water (1 ml). The mixture is stirred at reflux for 18 hours. After cooling to room temperature, the solvent is removed in vacuo and the residue is purified by column chromatography on silica with cyclohexane/ethyl acetate mixtures as eluent.

Yield: 105 mg (45% of th.) ¹H-NMR (300 MHz, CDCl₃): δ=1.3 (t, 3H); 2.0 (s, 3H); 3.9 (d, 1H); 4.3 (m, 2H); 4.5 (d, 1H); 7.4 (m, 2H); 7.5 (m, 2H); 7.6 (m, 1H); 7.7 (m, 2H) ppm.

Example 11

Ethyl 5-cyano-4-(4-cyanophenyl)-6-methyl-2-oxo-1-[3-(trifluoromethyl)phenyl]-1,2,3,4-tetrahydro-3-pyridinecarboxylate

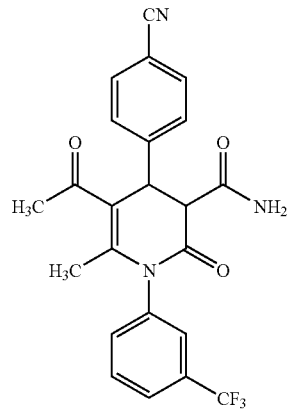

Example 7A (138 mg, 0.31 mmol) is dissolved in acetic acid (3 ml) and water (0.5 ml). The mixture is stirred at reflux for 18 hours. After cooling to room temperature, the solvent is removed in vacuo and the residue is purified by preparative HPLC.

Yield: 28 mg (20% of th.) ¹H-NMR (300 MHz, DMSO-d₆): δ=2.0 (s, 3H); 2.2 (s, 3H); 3.7 (d, 1H); 4.8 (d, 1H); 7.4 (br.s, 1H); 7.5 (m, 2H); 7.7 (m, 3H); 7.8 (m, 1H); 7.9 (m, 3H) ppm.

Example 12

5-Cyano-4-(4-cyanophenyl)-N,N,6-trimethyl-2-oxo-1-[3-(trifluoromethyl)phenyl]-1,2,3,4-tetrahydro-3-pyridinecarboxamide

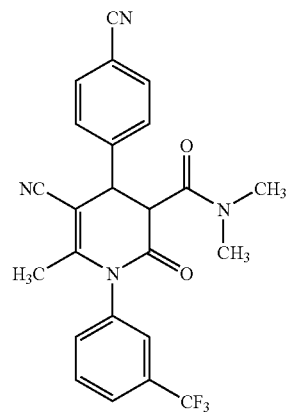

Example 12A (107 mg, 0.24 mmol) is dissolved in acetic acid (5 ml) and water (0.5 ml). The mixture is stirred at reflux for 18 hours. After cooling down to room temperature, the solvent is removed in vacuo and the residue is purified by preparative HPLC.

Yield: 69 mg (64% of th.) $^1$H-NMR (300 MHz, DMSO-$d_6$): δ=1.9 (s, 3H); 2.7 (s, 3H), 3.0 (s, 3H); 4.6 (d/d, 1H); 4.7 (d, 1H); 7.6 (m, 2H); 7.7 (m, 1H); 7.8 (m, 2H); 7.9 (m, 3H) ppm.

Example 13

5-Acetyl4-(4-cyanophenyl)-N,N,6-trimethyl-2-oxo-1-[3-(trifluoromethyl)phenyl]-1,2,3,4-tetrahydro-3-pyridinecarboxamide

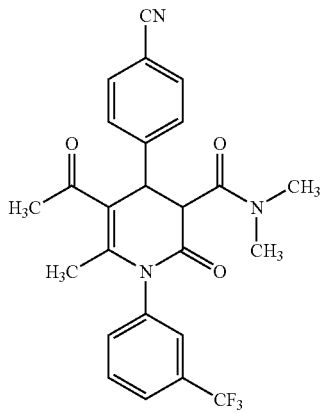

Example 8A (70 mg, 0.15 mmol) is dissolved in acetic acid (4 ml) and water (0.4 ml). The mixture is stirred at reflux for 18 hours. After cooling to room temperature, the solvent is removed in vacuo and the residue is purified by preparative HPLC.

Yield: 7 mg (10% of th.) $^1$H-NMR (300 MHz, DMSO-$d_6$): δ=2.0 (s, 3H); 2.1 (s, 3H); 2.9 (s, 3H); 3.2 (s, 3H); 4.3 (d, 1H); 4.6 (d, 1H); 7.6 (m, 2H); 7.7 (m, 2H); 7.7 (m, 1H); 7.8 (m, 1H); 7.9 (m, 2H) ppm.

Example 14

Ethyl 4-(4-cyanophenyl)-2-methyl-6-oxo-1-[3-(trifluoromethyl)phenyl]-1,4,5,6-tetrahydro-3-pyridinecarboxylate

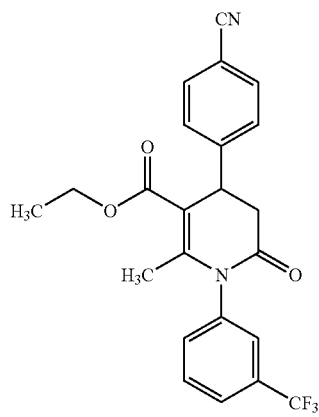

4-[(2,2-Dimethyl-4,6-dioxo-1,3-dioxan-5-ylidene)methyl]benzonitrile (Example 18A; 200 mg, 0.77 mmol) and ethyl (2E)-3-{[3-(trifluoromethyl)phenyl]amino}-2-butenoate (212.4 mg, 0.77 mmol) are dissolved in 1-methoxy-2-(2-methoxyethoxy)ethane (3 ml). The solution is stirred at reflux temperature overnight. The reaction mixture is cooled to room temperature and diluted with water (5 ml). After extraction with toluene (2×5 ml), it is dried with anhydrous sodium sulphate, filtered, and the solvent is removed in vacuo. The product is purified via preparative HPLC.

Yield: 28 mg (8% of th.) LC-MS (method 6): $R_t$=4.05 min MS (ESIpos): m/z=429 [M+H]$^+$.

Example 15

Diethyl 4-(5-cyano-1-benzofuran-2-yl)-6-methyl-2-oxo-1-[3-(trifluoromethyl)phenyl]-1,2,3,4-tetrahydro-3,5-pyridinedicarboxylate

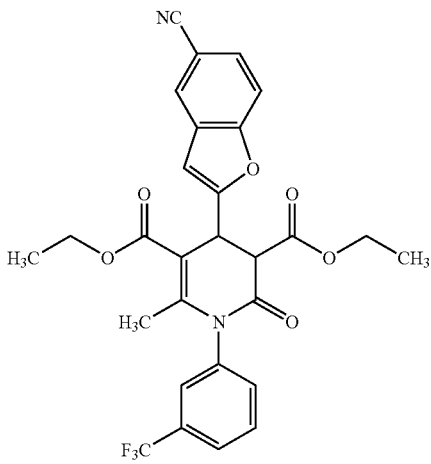

Example 20A (110 mg, 0.204 mmol) is dissolved in acetic acid (20 ml). The mixture is stirred at reflux for 18 hours. After cooling-to room temperature, the solvent is removed in vacuo and the residue is purified by preparative HPLC.

Yield: 10 mg (9% of th.) LC-MS (method 7): $R_t$=4.10 min MS (ESIpos): m/z=541 [M+H]$^{+1}$H-NMR (200 MHz, DMSO-$d_6$): δ=8.24–8.10 (m, 1H); 7.98–7.65 (m, 5H); 7.56–7.47 (m, 1H); 7.18–7.04 (m, 1H); 4.94 (br. d, 1H); 4.37–3.91 (m, 5H); 2.05 (s, 3H); 1.30–0.97 (m, 6H) ppm.

Example 16

Ethyl 4(4-cyanophenyl)-5-[(cyclopropylamino)carbonyl]-2-methyl-6-oxo-1-[3-(trifluoromethyl)phenyl]-1,4,5,6-tetrahydro-3-pyridinecarboxylate

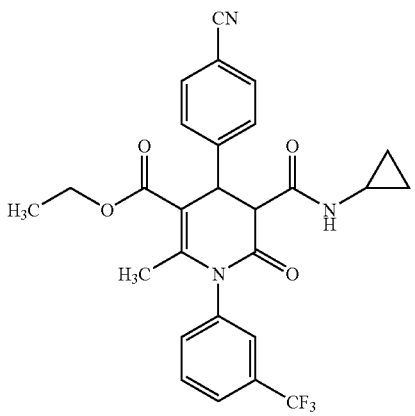

Example 21A (87 mg, 0.17 mmol) is dissolved in acetic acid (2 ml). The mixture is stirred at reflux for 18 hours. After cooling to room temperature, the solvent is removed in vacuo and the residue is purified by preparative HPLC.

Yield: 28 mg (33% of th.) $^1$H-NMR (200 MHz, DMSO-$d_6$): δ=0.3 (m, 1H); 0.5 (m, 1H); 0.7 (m, 1H); 1.1 (t, 3H); 2.1 (s, 3H); 2.7 (m, 1H); 3.6 (d, 1H); 4.1 (m, 2H); 4.6 (d, 1H); 7.6 (m, 2H); 7.7 (m, 2H); 7.8 (m, 1H); 7.9 (m, 3H); 8.6 (d, 1H) ppm.

Example 17

Ethyl 4-(4cyanophenyl)-5-[(isopropylamino)carbonyl]-2-methyl-6-oxo-1-[3-(trifluoromethyl)phenyl]-1,4,5,6-tetrahydro-3-pyridinecarboxylate

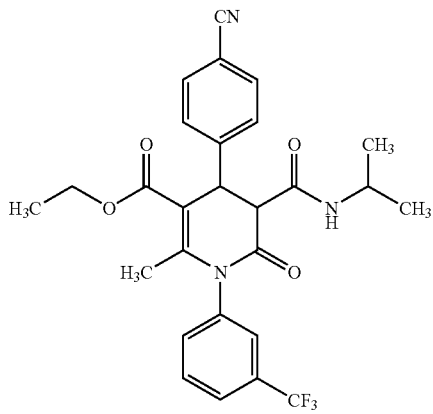

Example 22A (73 mg, 0.14 mmol) is dissolved in acetic acid (2 ml). The mixture is stirred at reflux for 18 hours. After cooling to room temperature, the solvent is removed in vacuo and the residue is purified by preparative HPLC.

Yield: 19 mg (26% of th.) $^1$H-NMR (300 MHz, DMSO-$d_6$): δ=1.1 (d, 3H; d, 3H); 1.2 (t, 3H); 2.1 (s, 3H); 3.6 (d, 1H); 3.9 (m, 1H); 4.1 (m, 2H); 4.7 (d, 1H); 7.5 (m, 2H); 7.7 (m, 2H); 7.8 (m, 1H); 7.9 (m, 3H); 8.3 (d, 1H) ppm.

Example 18 tert.-Butyl N-({5-cyano-4(4-cyanophenyl)-6-methyl-2-oxo-1-[3-(trifluoromethyl)-phenyl]-1,2,3,4-tetrahydro-3-pyridinyl}carbonyl)-β-alaninate

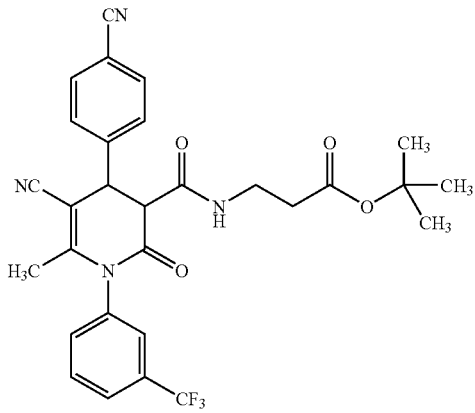

Example 2A (6.32 g, 28 mmol) is dissolved in ethanol (250 ml), and 4-cyanobenzaldehyde (3.67 g, 28 mmol), Example 24A (7.25 g, 28 mmol) and piperidine (0.24 g, 2.8 mmol) are added. The mixture is stirred at reflux for 18 hours. After cooling to room temperature, the precipitated product is filtered off Yield: 5.78 g (37% of th.) $^1$H-NMR (200 MHz, DMSO-$d_6$): δ=1.6 (s, 9H); 1.9 (s, 3H); 2.2 (m, 2H); 3.2 (m, 2E); 3.9 (d, 1H); 4.5 (d, 1H); 7.6 (m, 3E); 7.7 (m, 2H); 7.9 (m, 3H) ppm.

Example 19

N-({5-Cyano-4-(4-cyanophenyl)-6-methyl-2-oxo-1-[3-(trifluoromethyl)phenyl]-1,2,3,4-tetrahydro-3-pyridinyl}carbonyl)-β-alanine

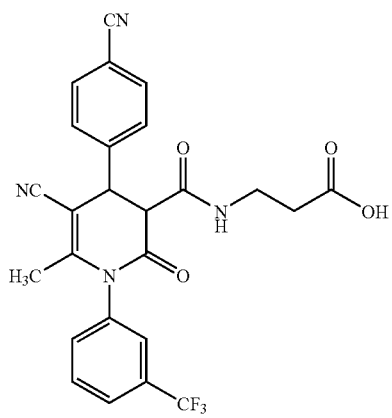

Example 18 (130 mg, 0.24 mmol) is dissolved in trifluoroacetic acid (1 ml) and stirred at room temperature for 30 mm. The solvent is removed in vacuo and the residue is purified by column chromatography (silica, eluent dichloromethane/methanol 100:1, 40:1).

Yield: 106 mg (91% ofth.) $^1$H-NMR (200 MHz, DMSO-$d_6$): δ=1.9 (s, 3H); 2.2 (m, 2H); 3.2 (m, 2H); 3.9 (d, 1H); 4.5 (d, 1H); 7.6 (m, 3H); 7.7 (m, 2H); 7.9 (m, 3H); 8.3 (t, 3H) ppm.

Example 20

5-Cyano-4-(4-cyanophenyl)-N-(2-methoxyethyl)-6-methyl-2-oxo-1-[3-(trifluoromethyl)phenyl]-1,2,3,4-tetrahydro-3-pyridinecarboxamide

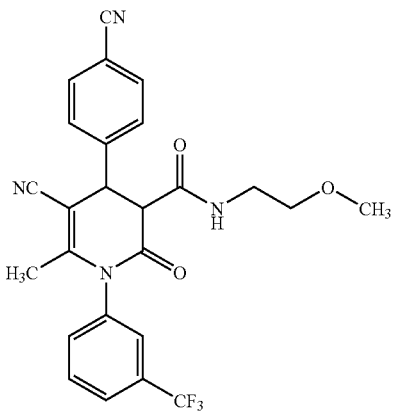

Example 2A (2.14 g, 9.5 mmol) is dissolved in ethanol (25 ml), and 4-cyanobenzaldehyde (1.24 g, 9.5 mmol), Example 23A (1.79 g, 9.5 mmol) and piperidine (0.08 g, 0.95 mmol) are added. The mixture is stirred at reflux for 18 hours. After cooling to room temperature, the solvent is removed in vacuo and the residue is purified by column chromatography (silica, eluent cyclohexane/ethyl acetate 5:1, 2:1, 1:1).

Yield: 1.60 g (35% of th.) $^1$H-NMR (300 MHz, DMSO-$d_6$): δ=1.9 (s, 3H); 3.2 (s, 3H; m, 2H); 3.3 (m, 2H); 3.9 (d, 1H); 4.5 (d, 1H); 7.6 (m, 3H); 7.7 (m, 2H); 7.9 (m, 3H); 8.3 (t, 3H) ppm.

Examples 21 and 22 tert.-Butyl N-({5-cyano-4-(4-cyanophenyl)-6-methyl-2-oxo-1-[3-(trifluoromethyl)-phenyl]-1,2,3,4-tetrahydro-3-pyridinyl}carbonyl)-L-alaninate

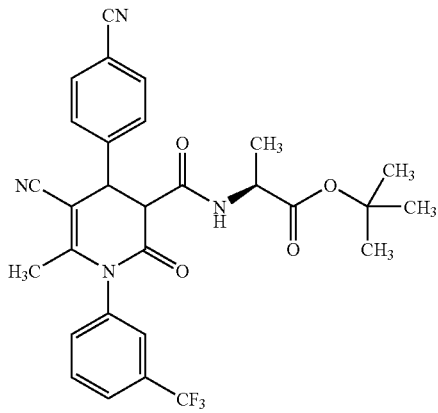

Example 2A (2.40 g, 10.6 mmol) is dissolved in ethanol (22 ml), and 4-cyanobenzaldehyde (1.39 g, 10.6 mmol), Example 25A (2.75 g, 10.6 mmol) and piperidine (0.09 g, 1.06 mmol) are added. The mixture is stirred at reflux for 18 hours. After cooling to room temperature, the solvent is removed in vacuo and the crude product is purified and separated into the diastereomers by column chromatography (silica, eluent toluene/ethyl acetate 10:1, 8:1).

Diastereomer 1 (Example 21):

Yield: 0.61 g (11% of th.) $^1$H-NMR (200 MHz, DMSO-$d_6$): δ=1.2 (d, 3H); 1.35 (s, 9H); 1.9 (s, 3H); 3.95 (d, 1H); 4.15 (m, 1H); 4.4 (d, 1H); 7.6 (m, 3H); 7.8 (m, 2H); 7.9 (m, 1H; m, 2J); 8.7 (d, 1H) ppm.

Diastereomer 2 (Example 22):

Yield: 1.2 g (21% of th.) $^1$H-NM (200 MHz, DMSO-$d_6$): δ=1.1 (d, 3H); 1.4 (s, 9H); 1.9 (s, 3H); 3.95 (d, 1H); 4.1 (m, 1H); 4.5 (d, 1H); 7.6 (m, 3H); 7.8 (m, 2H); 7.9 (m, 1H; m, 2H); 8.7 (d, 1H) ppm.

Example 23

N-({5-Cyano-4-(4-cyanophenyl)-6-methyl-2-oxo-1-[3-(trifluoromethyl)phenyl]-1,2,3,4-tetrahydro-3-pyridinyl}carbonyl)-L-alanine

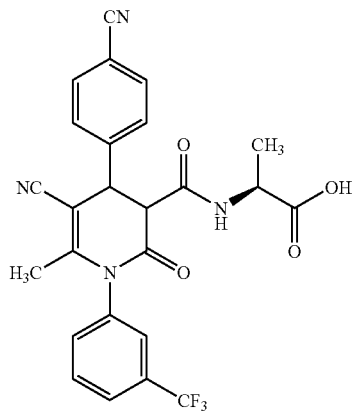

Example 22 (1.09 g, 2 mmol) is dissolved in trifluoroacetic acid (10 ml) and stirred at room temperature for 30 min. The solvent is removed in vacuo and the residue is purified by column chromatography (silica, eluent dichloromethane/methanol 80:1, 20:1).

Yield: 0.92 g (94% of th.) $^1$H-NMR (300 MHz, DMSO-$d_6$): δ=1.1 (d, 3H); 1.9 (s, 3H); 4.9 (d, 1H); 4.2 (quint, 1H); 4.5 (d, 1H); 7.7 (m, 3H); 7.8 (m, 2H); 7.9 (m, 3H); 8.6 (d, 1H) ppm.

Example 24

5-Cyano-4-(4-cyanophenyl)-6-methyl-2-oxo-N-[(1S)-1-phenylethyl]-1-[3-(trifluoromethyl)phenyl]-1,2,3,4-tetrahydro-3-pyridinecarboxamide

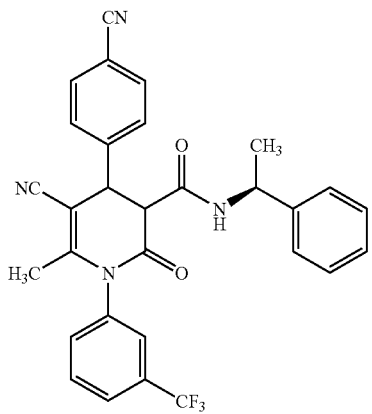

Example 2A (1.40 g, 6.2 mmol) is dissolved in ethanol (12 ml), and 4-cyanobenzaldehyde (0.82 g, 6.2 mmol), Example 27A (1.46 g, 6.2 mmol) and piperidine (53 mg, 0.62 mmol) are added. The mixture is stirred at reflux for 18 hours. After cooling to room temperature, the solvent is removed in vacuo and the crude product is purified and separated into the diastereomers by column chromatography (silica, eluent cyclohexane/ethyl acetate 10:1, 5:1, 2:1).

Yield: 0.31 g (10% of th.) (faster eluting diastereomer 1) $^1$H-NM (300 MHz, DMSO-$d_6$): δ=1.3 (d, 3H); 1.9 (s, 3H);

4.0 (d, 1H); 4.5 (d, 1H); 4.9 (quint, 1H); 6.9 (m, 2H); 7.2 (m, 3H); 7.6 (m, 2H); 7.65 (m, 1H); 7.8 (m, 2H); 7.9 (m, 3H); 8.6 (d, 1H) ppm.

Example 25

5-Cyano-4-(4-cyanophenyl)-6-methyl-2-oxo-N-[(1R)-1-phenylethyl]-1-[3-(trifluoromethyl)phenyl]-1,2,3,4-tetrahydro-3-pyridinecarboxamide

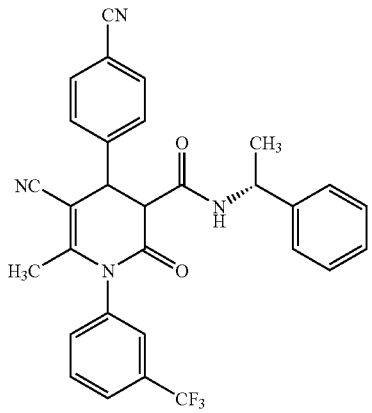

Example 2A (1.73 g, 7.7 mmol) is dissolved in ethanol (16 ml), and 4-cyanobenzaldehyde (1.0 g, 7.7 mmol), Example 28A (1.80 g, 7.7 mmol) and piperidine (130 mg, 1.53 mmol) are added. The mixture is stirred at reflux for 18 hours. After cooling to room temperature, the solvent is removed in vacuo and the crude product is purified and separated into the diastereomers by column chromatography (silica, eluent cyclohexane/ethyl acetate 10:1, 5:1, 2:1).

Yield: 0.25 g (6% of th.) (slower eluting diastereomer 2) $^1$H-NMR (400 MHz, DMSO-$d_6$): δ=1.15 (d, 3H); 1.9 (s, 3H); 4.0 (d, 1H); 4.6 (d, 1H); 4.8 (m, 1H); 7.2 (m, 1H); 7.3 (m, 4H); 7.6 (m, 2H); 7.7 (m, 2H); 7.8 (m, 1H); 7.9 (m, 2H); 8.7 (d, 1H) ppm.

Examples 26 and 27

Ethyl N-({5-cyano-4-(4-cyanophenyl)-6-methyl-2-oxo-1-[3-(trifluoromethyl)phenyl]-1,2,3,4-tetrahydro-3-pyridinyl}carbonyl)alaninate

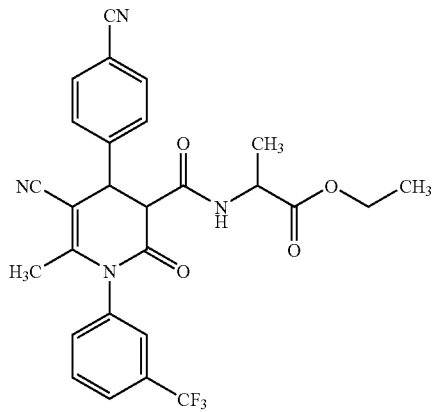

Example 2A (1.60 g, 7.1 mmol) is dissolved in ethanol (16 ml), and 4-cyanobenzaldehyde (0.93 g, 7.1 mmol), Example 26A (1.64 g, 7.1 mmol) and piperidine (0.06 g, 0.71 mmol) are added. The mixture is stirred at reflux for 18 hours. After cooling to room temperature, the solvent is removed in vacuo and the crude product is purified and separated into the diastereomers by column chromatography (silica, eluent cyclohexane/ethyl acetate 4:1, 2:1).

Diastereomer 1 (Example 26):

Yield: 0.12 g (3% of th.) $^1$H-NMR (200 MHz, DMSO-$d_6$): δ=1.1 (d, 3H); 1.2 (t, 3H); 1.9 (s, 3H); 4.0 (d, 1H); 4.1 (m, 2H); 4.2 (m, 1H); 4.5 (d, 1H); 7.6 (m, 3H); 7.7–7.8 (m, 3H); 7.9 (m, 2H); 8.8 (d, 1H) ppm.

Diastereomer 2 (Example 27):

Yield: 0.32 g (9% of th.) $^1$H-NMR (200 MHz, DMSO-$d_6$): δ=1.1 (t, 3H); 1.2 (d, 3H); 1.9 (s, 3H); 4.0 (m, 3H); 4.2 (m, 1H); 4.5 (d, 1H); 7.7 (m, 4H); 7.8 (m, 2H); 7.9 (m, 2H); 8.8 (d, 1H) ppm.

The following compounds are prepared analogously as described for Example 20A:

| Ex.-No. | Starting material | Structure | Analytical data |
|---|---|---|---|
| 28 | Example 2A; 4-bromo-benzaldehyde; methyl 3-amino-3-oxopropanoate | (structure shown) | LC-MS (method 4): $R_t$ = 3.73 min. MS (EI): m/z = 478 [M + H]$^+$ |

-continued

| Ex.-No. | Starting material | Structure | Analytical data |
|---|---|---|---|
| 29 | Example 2A; 4-cyano-benzaldehyde; Example 29A | (structure) | LC-MS (method 4): $R_t$ = 3.45 min. MS (EI): m/z = 439 $[M + H]^+$ |
| 30 | Example 2A; 4-cyano-2-methyl-benzaldehyde; methyl 3-amino-3-oxopropanoate | (structure) | LC-MS (method 4): $R_t$ = 3.54 min. MS (EI): m/z = 439 $[M + H]^+$ |
| 31 | Example 2A; 4-cyano-benzaldehyde; methyl 3-[(4-bromophenyl)-amino]-3-oxopropanoate | (structure) | LC-MS (method 4): $R_t$ = 4.32 min. MS (EI): m/z = 579/581 $[M + H]^+$ |

| Ex.-No. | Starting material | Structure | Analytical data |
|---|---|---|---|
| 32 | Example 2A; 4-cyano-benzaldehyde; ethyl 3-(ethylamino)-3-oxopropanoate | 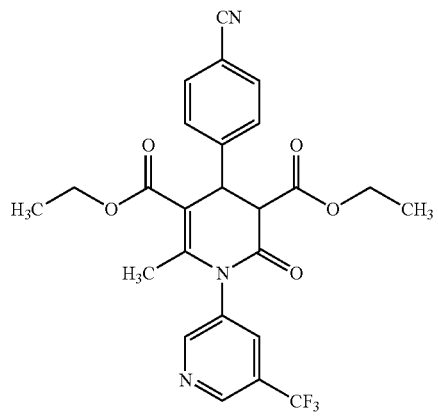 | LC-MS (method 7): $R_t$ = 3.60 min. MS (EI): m/z = 453 [M + H]$^+$ |

Example 33

Diethyl 4-(4-cyanophenyl)-6-methyl-2-oxo-5'-(trifluoromethyl)-3,4-dihydro-2H-1,3'-bipyridine-3,5-dicarboxylate

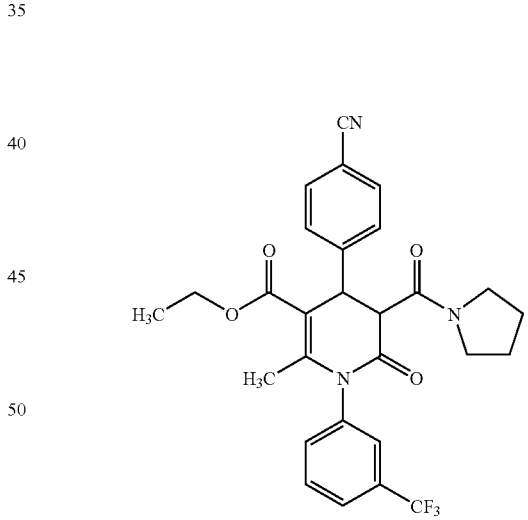

Example 33A (50 mg, 0.096 mmol), Amberlyst 15 (50 mg) and magnesium sulphate monohydrate (100 mg, 0.72 mmol) are dissolved in absolute ethanol (10 ml). The reaction mixture is refluxed overnight (18 hours) under argon, cooled to room temperature, filtered through celite and concentrated to afford a yellow oil which is purified by preparative HPLC using an acetonitrile/water (1:9 to 9:1) gradient.

Yield: 15 mg (20% of th.) HPLC (method 6): $R_f$=3.97 min. MS (ESIpos): m/z=502 [M+H]$^+$ $^1$H-NMR (200 MHz, DMSO-d$_6$): δ=9.08 (s, 1H); 8.74 (s, 1H); 8.67 (m, 1H); 7.85 (d, 2H); 7.65 (d, 2H); 4.76 (br. d, 1H); 4.38–3.78 (m, 5H); 2.13 (s, 3H); 1.29–0.80 (m, 6H) ppm.

Example 34

Ethyl 4-(4-cyanophenyl)-2-methyl-6-oxo-5-(1-pyrrolidinylcarbonyl)-1-[3-(trifluoromethyl)phenyl]-1,4,5,6-tetrahydro-3-pyridinecarboxylate Prepared according to the procedure described in Example 33 from Example 37A (100 mg, 0.184 mmol).

Yield: 38.7 mg (40% of th.) HPLC (method 5): $R_f$=4.8 min., λ$_{max}$ 196 nm MS (ESIpos): m/z=526 [M+H]$^+$ $^1$H-NMR (200 MHz, DMSO-d$_6$): δ=7.92–7.52 (m, 8H); 4.58 (d, 1H); 4.11–3.89 (m, 3H); 3.85–3.67 (m, 2H); 3.61–3.42 (m, 2H); 2.05 (s, 3H); 1.96–1.67 (m, 4H); 1.01 (t, 3H) ppm.

Example 35

Ethyl 4-(4-cyanophenyl)-5-{[(2-methoxyethyl)(methyl)amino]carbonyl}-2-methyl-6-oxo-1-[3-(trifluoromethyl)phenyl]-1,4,5,6-tetrahydro-3-pyridinecarboxylate

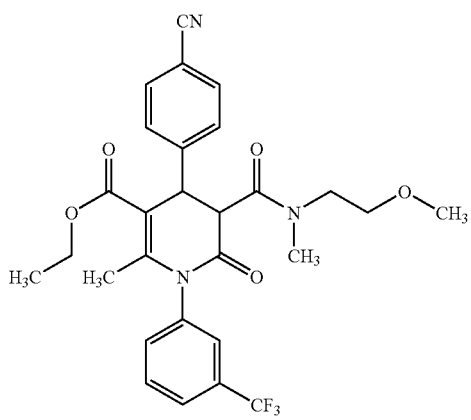

Prepared according to the procedure described in Example 33 from Example 39A (100 mg, 0.78 mmol).

Yield: 84.8 mg (88% of th.) HPLC (method 5): $R_t$=4.83 min., $\lambda_{max}$ 200 nm MS (ESIpos): m/z=544 [M+H]$^+$.

Example 36

Ethyl 4-(4-cyanophenyl)-5-[(diethylamino)carbonyl]-2-methyl-6-oxo-1-[3-(trifluoromethyl)phenyl]-1,4,5,6-tetrahydro-3-pyridinecarboxylate

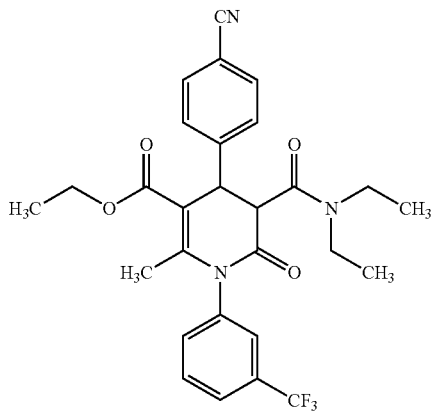

Prepared according to the procedure described in Example 33 from Example 41A (100 mg, 0.183 mmol).

Yield: 50 mg (52% of th.) HPLC (method 5): $R_t$=4.99 min., $\lambda_{max}$ 200 nm MS (ESIpos): m/z=528 [M+H]$^+$ $^1$H-NMR (300 MHz, DMSO-d$_6$): δ=7.87–7.49 (m, 8H); 4.58 (d, 1H); 4.25 (d, 1H); 3.99–3.82 (m, 2H); 3.56–3.09 (m, 4H); 1.98 (s, 3H); 1.02 (t, 3H); 0.98–0.86 (m, 6H) ppm.

Example 37

Ethyl 4-(4-cyanophenyl)-2-methyl-5-(4-morpholinylcarbonyl)-6-oxo-1-[3-(trifluoromethyl)phenyl]-1,4,5,6-tetrahydro-3-pyridinecarboxylate

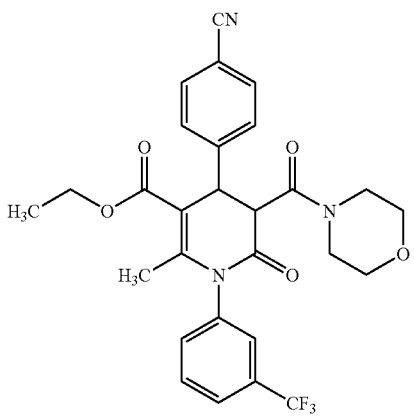

Prepared according to the procedure described in Example 33 from Example 43A (100 mg, 0.79 mmol).

Yield: 80 mg (75% of th.) HPLC (method 5): $R_t$=4.78 min., $\lambda_{max}$ 198 nm MS (ESIpos): m/z=542 [M+H]$^+$ $^1$H-NMR (300 MHz, DMSO-d$_6$): δ=7.90–7.32 (m, 8H); 4.55 (d, 1H); 4.37 (d, 1H); 4.09–3.89 (m, 2H); 3.73-3-35 (m, 8H); 2.02 (s, 3H); 1.04 (t, 3H) ppm.

Example 38

Ethyl 4-(4-cyanophenyl)-2-methyl-6-oxo-5-(1,3-thiazolidin-3-ylcarbonyl)-1-[3-(trifluoromethyl)phenyl]-1,4,5,6-tetrahydro-3-pyridinecarboxylate

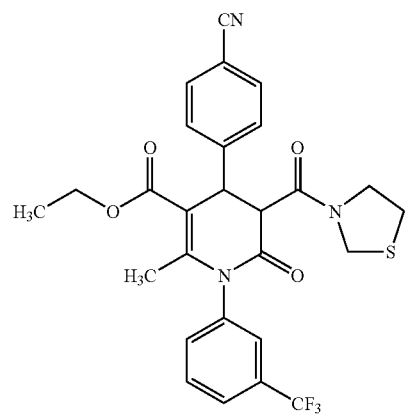

Prepared according to the procedure described in Example 33 from Example 45A (130 mg, 0.23 mmol).

Yield: 71 mg (57% of th.) HPLC (method 5): $R_t$=4.90 min., $\lambda_{max}$ 202 nm MS (ESIpos): m/z=544 [M+H]$^+$ $^1$H-NMR (200 MHz, DMSO-d$_6$): δ=7.97–7.53 (m, 8H); 4.99–4.19 (m, 4H); 4.17–2.89 (m, 6H); 2.04 (s, 3H); 1.01 (t, 3H) ppm.

Example 39

Ethyl 5',6-dicyano-6'-methyl-2'-oxo-1'-[3-(trifluoromethyl)phenyl]-1',2',3',4'-tetrahydro-3,4'-bipyridine-3'-carboxylate

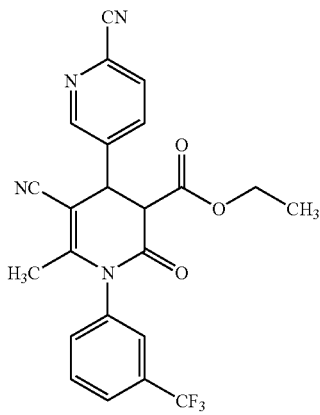

Example 2A (650 mg, 2.87 mmol), Example 52A (380 mg, 2.87 mmol), diethyl malonate (460 mg, 2.87 mmol) and piperidine (24 mg, 0.29 mmol) are refluxed in ethanol (7 ml) overnight (18 h). The reaction mixture is cooled to room temperature, diluted with DMSO (5 ml) and purified by preparative HPLC.

Yield: 454 mg (23% of th.) $^1$H-NMR (300 MHz, DMSO-$d_6$): δ=8.86 (s, 1H); 8.16 (m, 2H.); 7.93–7.34 (m, 4H); 4.74 (d, 1H); 4.5 (d, 1H); 4.26 (d, 3H); 1.95 (d, 3 H); 1.1 (t, 3H) ppm.

Example 40

2'-Methyl-6'-oxo-1'-[3-(trifluoromethyl)phenyl]-1',4',5',6'-tetrahydro-3,4'-bipyridine-3',6-dicarbonitrile

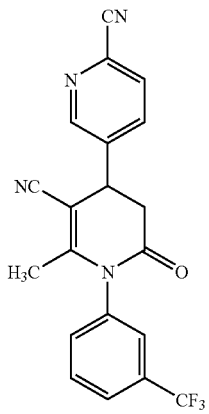

Example 39 (250 mg, 0.55 mmol), sodium chloride (325 mg, 5.5 mmol) and water (0.75 ml) are stirred in DMSO (3 ml) at 150° C. for two hours. The reaction mixture is cooled to room temperature, diluted with DMSO (5 ml) and purified by preparative HPLC (acetonitrile/water 1:9 to 9:1 gradient).

Yield: 98 mg (47% of th.) $^1$H-NMR (200 MHz, DMSO-$d_6$): δ=8.84 (s, 1H); 8.19–8.06 (m, 2H); 7.90–7.56 (m, 4H); 4.51–4.32 (m, 1H); 3.31–2.90 (m, 2H); 1.93 (s, 3H) ppm.

Example 41

Ethyl 4-(4-cyanophenyl)-2-methyl-5-[(4-methyl-1-piperazinyl)carbonyl]-6-oxo-1-[3-(trifluoromethyl)phenyl]-1,4,5,6-tetrahydro-3-pyridinecarboxylate

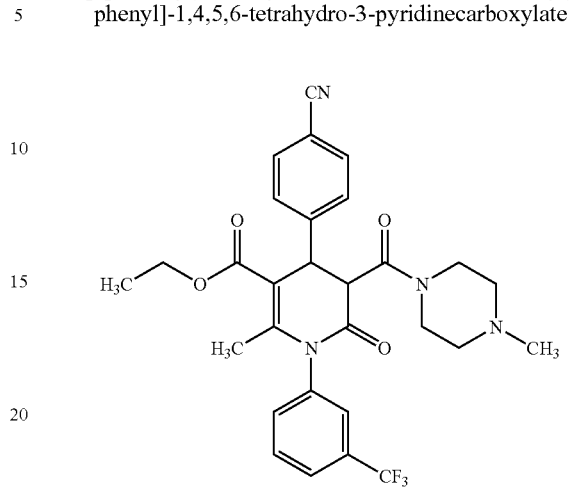

Prepared according to the procedure described in Example 33 from Example 49A (120 mg, 0.210 mmol).

Yield: 35 mg (30% of th.) $^1$H-NMR (200 MHz, DMSO-$d_6$): δ=7.89–7.66 (m, 4H); 7.63–7.42 (m, 4H); 4.55 (d, 1H); 4.36 (d, 1H); 4.10–3.89 (m, 2H); 3.67–3.34 (m, 4H); 2.2–2.4 (m, 4H); 2.16 (s, 3M); 2.02 (d, 3H); 1.04 (t, 3H) ppm.

Example 42

Diethyl 4-(4-chlorophenyl)-6-methyl-2-oxo-1-[3-(trifluoromethyl)phenyl]-1,2,3,4-tetrahydro-3,5-pyridinedicarboxylate

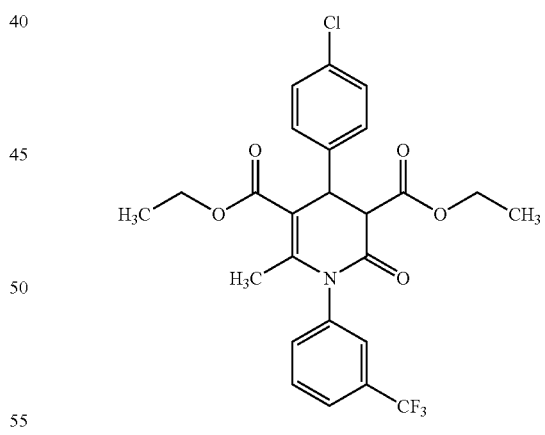

Example 54A (28.4 mg, 0.06 mmol) is dissolved in 0.5 ml tetrahydrofuran. The solution is cooled to −78° C., lithium diisopropylamide (2 M solution in THF/heptane, 0.14 ml) is added dropwise, and the reaction mixture is stirred at −78° C. for 1 hour. Ethyl chloroformate (10.8 mg, 0.1 mmol) is added, and the reaction mixture is stirred at −78° C. for an additional 4 hours. The mixture is kept at −22° C. overnight and is then quenched with saturated aqueous ammonium chloride solution. The solvent is removed in vacuo and the residue is purified by preparative HPLC.

Yield: 3.3 mg (10% of th.) LC-MS (method 6): $R_t$=4.57 min. $^1$H-NMR (200 MHz, CDCl$_3$): δ=1.21 (t, 3H); 1.33 (t, 3H); 2.14 (s, 3H); 3.79 (d, 1H); 3.99–4.42 (m, 4H); 4.80 (s, 1H); 7.19–7.75 (m, 8H) ppm.

Example 43

4-(4-Cyanophenyl)-2-methyl-6-oxo-1-[3-(trifluoromethyl)phenyl]-1,4,5,6-tetrahydro-3-pyridinecarbonitrile

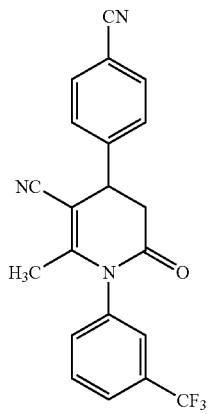

Example 19A (50 mg, 0.20 mmol) and Example 2A (35 mg, 0.16 mmol) are dissolved in 1.5 ml tert.-butanol, 1,8-diazabicyclo[5.4.0]undec-7-ene (2.36 mg, 0.02 mmol) is added, and the reaction mixture is refluxed overnight. Additional amounts of Example 19A (10 mg, 0.04 mmol) and 1,8-diazabicyclo[5.4.0]undec-7-ene (2.36 mg, 0.02 mmol) are added, and the reaction mixture is again refluxed overnight. The solvent is then removed in vacuo and the residue is purified by column chromatography (silica, eluent cyclohexane/ethyl acetate 3:1).

Yield: 20.8 mg (32% of th.) HPLC (method 5): $R_t$=4.63 min. MS (DCI): m/z=399 [M+NH$_4$]$^+$ $^1$H-NMR (200 MHz, CDCl$_3$): δ=2.02 (d, 3H); 3.02 (dd, 1H); 3.21 (dd, 1H); 4.07)dd, 1H); 7.35–7.80 (m, 8H) ppm.

Example 44

4-{5-Acetyl-6-methyl-2-oxo-1-[3-(trifluoromethyl)phenyl]-1,2,3,4-tetrahydro-4-pyridinyl}benzonitrile

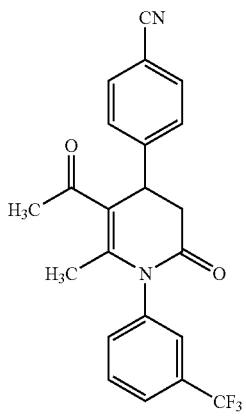

Example 4 (1.50 g, 3.2 mmol) is suspended in dioxane/water (2:1 by volume, 22.5 ml), sodium hydroxide (0.56 ml of a 45% aqueous solution, 6.4 mmol) is added, and the reaction mixture is stirred at room temperature for 4 hours. The mixture is acidified with 1 M hydrochloric acid to pH4 and extracted three times with dichloromethane. The combined organic phases are dried with sodium sulphate, and the solvent is removed in vacuo. The residue is purified by column chromatography (silica, eluent cyclohexane/ethyl acetate 3:1, 2:1, then dichloromethane/methanol/formic acid 12:1:0.1). The resulting crude product is further purified by preparative HPLC.

Yield: 146 mg (11% of th.) HPLC (method 5): $R_t$=4.65 min. MS (DCI): m/z=399 [M+H]$^+$ $^1$H-NMR (200 MHz, CDCl$_3$): δ=2.11 (s, 3H); 2.20 (s, 3H); 2.97 (dd, 1H); 3.21 (dd, 1H); 4.31 (m, 1H); 7.15–7.77 (m, 8H) ppm.

Example 45

4-{5-Acetyl-6-methyl-3-(4-morpholinylcarbonyl)-2-oxo-1-[3-(trifluoromethyl)-phenyl]-1,2,3,4-tetrahydro-4-pyridinyl}benzonitrile

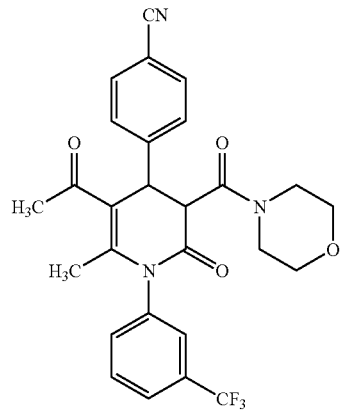

Example 4 (30 mg, 0.06 mmol) is dissolved in morpholine (0.5 ml, 5.7 mmol). The reaction mixture is stirred at 60° C. for 1.5 hours and at 80° C. overnight. The mixture is then allowed to stand at room temperature for 48 hours. The solvent is removed in vacuo and the resulting crude product is purified by preparative HPLC.

Yield: 4.5 mg (13% of th.) LC-MS (method 7): $R_t$=3.64 min. $^1$H-NMR (300 MHz, DMSO-d$_6$): δ=1.94 (s, 3H); 2.15 (s, 3H); 3.41–3.80 (m, 8H); 4.35 (d, 1H); 4.59 (d, 1H); 7.51–7.90 (m, 8H) ppm.

Example 46

Allyl 4-(4-cyanophenyl)-2-methyl-6-oxo-1-[3-(trifluoromethyl)phenyl]-1,4,5,6-tetrahydro-3-pyridinecarboxylate

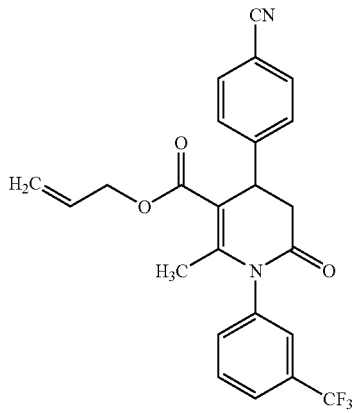

To a solution of allyl 2-acetyl-3-(4-cyanophenyl)-5-oxo-5-{[3-(trifluoromethyl)-phenyl]amino}pentanoate (Example 53A) (12.60 g, 27.49 mmol) in 400 ml ethanol are added Amberlyst-15 (12.60 g) and magnesium sulphate (25.20 g, 209.4 mmol). The reaction mixture is stirred at reflux temperature overnight and then cooled to room temperature. The solids are removed by filtration using a pad of kieselgur. The solvent is removed in vacuo and the crude material is purified by column chromatography on silica gel (eluent dichloromethane).

Yield: 7.24 g (60% of th.) LC-MS (method 8): $R_t$=4.20 min. MS (EI): m/z=441 [M+H]$^+$.

Example 47

4-(4-Cyanophenyl)-2-methyl-6-oxo-1-[3-(trifluoromethyl)phenyl]-1,4,5,6-tetrahydro-3-pyridinecarboxylic acid

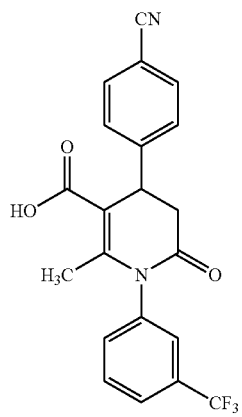

To a solution of allyl 4-(4-cyanophenyl)-2-methyl-6-oxo-1-[3-(trifluoromethyl)phenyl]-1,4,5,6-tetrahydro-3-pyridinecarboxylate (Example 46) (1.00 g, 2.27 mmol) and tetrakis(triphenylphosphin)-palladium(0) (68 mg, 0.059 mmol) in tetrahydrofuran (50 ml) is slowly added morpholine (3.36 g, 38.6 mmol). After stirring at room temperature for 1 h, the reaction mixture is quenched with water (50 ml). The basic solution (pH ca. 10) is neutralised with 1 N hydrochloric acid, and the aqueous phase is extracted with ethyl acetate (2×100 ml). The combined organic layers are washed with water, dried, and the solvent is removed in vacuo to yield pure product.

Yield: 600 mg (66% of th.) LC-MS (method 7): $R_t$=3.50 min. MS (EI): m/z=401 [M+H]$^+$ $^1$H-NMR (300 MHz, DMSO-d$_6$): δ=2.11 (s, 3H); 2.72 (dd, 1H); 3.18–3.42 (1H); 4.37 (d, 1H); 7.54–7.87 (8H); 12.50 (br. s, 1H) ppm.

Example 48

2-Hydroxyethyl 4-(4-cyanophenyl)-2-methyl-6-oxo-1-[3-(trifluoromethyl)phenyl]-1,4,5,6-tetrahydro-3-pyridinecarboxylate

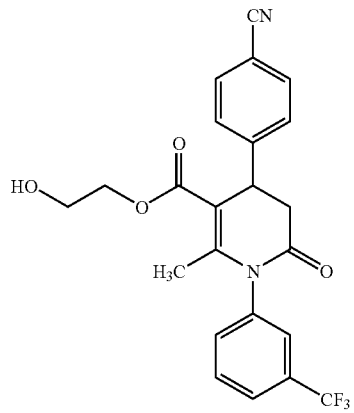

To a solution of 40 mg (0.1 mmol) of the compound of Example 47 in 0.3 ml dry dimethylformamide are added 48.6 mg (0.3 mmol) N,N-carbonyldiimidazole. After allowing the reaction mixture to stand for one hour, the reaction mixture is diluted with water and extracted with ethyl acetate. After drying with magnesium sulfate, the solvent is evaporated off in vacuo. To the residue are added 0.5 ml (555 mg, 8.95 mol) ethylene glycol and 10 µl (0.07 mmol) triethylamine. The reaction mixture is stirred at 100° C. for one hour. Then the reaction mixture is filtered and purified by preparative HPLC (column: Nucleosil 100-5 C 18 Nautilus 20 mm×50 mm, 5 µm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; wavelength: 220 nm; injection volume: approx. 550 µl; number of injections: 1). The product containing fractions are combined and concentrated in vacuo.

Yield: 13 mg (29.5% of th.) MS (ESIpos): m/z=445 [M+H]$^+$ $^1$H-NMR (300 MHz, DMSO-d$_6$): δ=7.85–7.45 (m, 8H); 4.7 (tr, 1H); 4.45 (d, 1H); 4.1 (d tr, 1H); 4.0 (d tr, 1H); 3.5 (q, 2H); 2.8 (dd, 1H); 2.1 (s, 3H) ppm.

Example 49

2-(Dimethylamino)ethyl 4-(4-cyanophenyl)-2-methyl-6-oxo-1-[3-(trifluoromethyl)-phenyl]-1,4,5,6-tetrahydro-3-pyridinecarboxylate

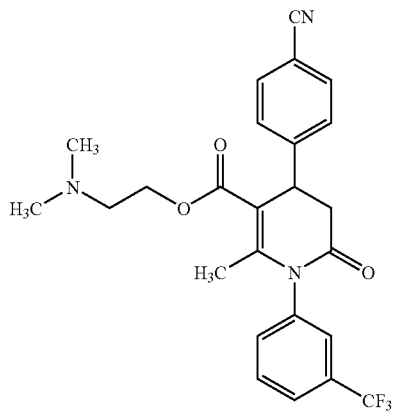

To a solution of 40 mg (0.1 mmol) of the compound of Example 47 in 0.3 ml dry dimethylformamide are added 48.6 mg (0.3 mmol) N,N-carbonyldiimidazole. After allowing the reaction mixture to stand for one hour, the reaction mixture is diluted with water and extracted with ethyl acetate. After drying with magnesium sulfate, the solvent is evaporated off in vacuo. To the residue are added 0.5 ml (443 mg, 4.98 mmol) 2-(dimethylamino)ethanol and 10 µl (0.07 mmol) triethylamine. The reaction mixture is stirred at 100° C. for one hour. Then the reaction mixture is filtered and purified by preparative HPLC (column: Nucleosil 100-5 C 18 Nautilus 20 mm×50 mm, 5 µm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; wavelength: 220 nm; injection volume: approx. 550 µl; number of injections: 1). The product containing fractions are combined and concentrated in vacuo.

Yield: 13 mg (27.5% of th.) MS (ESIpos): m/z=472 [M+H]$^+$ $^1$H-NMR (300 MHz, DMSO-d$_6$): δ=7.85–7.45 (m, 8H); 4.4 (d, 1H); 4.1 (m, 2H); 3.3 (dd, 1H); 2.8 (dd, 1H); 2.4 (tr, 2H); 2.1 (s, 3H); 2.05 (s, 6H) ppm.

Example 50

2-(1-Pyrrolidinyl)ethyl 4-(4-cyanophenyl)-2-methyl-6-oxo-1-[3-(trifluoromethyl)-phenyl]-1,4,5,6-tetrahydro-3-pyridinecarboxylate

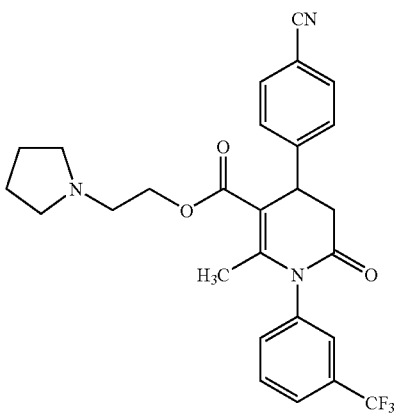

To a solution of 40 mg (0.1 mmol) of the compound of Example 47 in 0.3 ml dry dimethylformamide are added 48.6 mg (0.3 mmol) N,N-carbonyldiimidazole. After allowing the reaction mixture to stand for one hour, the reaction mixture is diluted with water and extracted with ethyl acetate. After drying with magnesium sulfate, the solvent is evaporated off in vacuo. To the residue are added 0.5 ml (492 mg, 4.28 mmol) 1-(2-hydroxyethyl)pyrrolidin and 10 µl (0.07 mmol) triethylamine. The reaction mixture is stirred at 100° C. for one hour. Then the reaction mixture is filtered and purified by preparative HPLC (column: Nucleosil 100-5 C 18 Nautilus 20 mm×50 mm, 5 µm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; wavelength: 220 nm; injection volume: approx. 550 µl; number of injections: 1). The product containing fractions are combined and concentrated in vacuo.

Yield: 10 mg (20.1% of th.) MS (ESIpos): m/z=498 [M+H]$^+$ $^1$H-NMR (300 MHz, DMSO-d$_6$): δ=7.85–7.45 (m, 8H); 4.4 (d, 1H); 4.1 (m, 2H); 3.3 (dd, 1H); 2.8 (dd, 1H); 2.6 (tr, 2H); 2.3 (m, 4H); 2.1 (s, 3H); 1.6 (m, 4H) ppm.

Example 51

2-(Acetylamino)ethyl 4-(4-cyanophenyl)-2-methyl-6-oxo-1-[3-(trifluoromethyl)-phenyl]-1,4,5,6-tetrahydro-3-pyridinecarboxylate

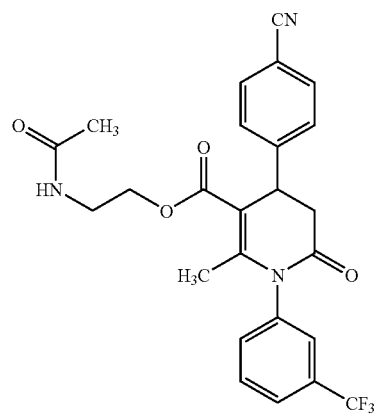

To a solution of 40 mg (0.1 mmol) of the compound of Example 47 in 0.3 ml dry dimethylformamide are added 48.6 mg (0.3 mmol) N,N-carbonyldiimidazole. After allowing the reaction mixture to stand for one hour, the reaction mixture is diluted with water and extracted with ethyl acetate. After drying with magnesium sulfate, the solvent is evaporated off in vacuo. To the residue are added 0.5 ml (560 mg, 5.44 mmol) N-2-hydroxyethyl-acetamide and 10 µl (0.07 mmol) triethylamine. The reaction mixture is stirred at 100° C. for one hour. Then the reaction mixture is filtered and purified by preparative HPLC (column: Nucleosil 100-5 C 18 Nautilus 20 mm×50 mm, 5 µm; solvent A: acetonitrile, solvent B: water+0.1% formic acid; gradient: 0 min 10% A, 2 min 10% A, 6 min 90% A, 7 min 90% A, 7.1 min 10% A, 8 min 10% A; wavelength: 220 nm; injection volume: approx. 550 µl; number of injections: 1). The product containing fractions are combined and concentrated in vacuo.

Yield: 8 mg (16.5% of th.) MS (ESIpos): m/z=486 [H]$^+$ $^1$H-NMR (300 MHz, DMSO-d$_6$): δ=7.85–7.45 (m, 9H); 4.4 (d, 1H); 4.1 (d tr, 1H); 3.9 (d tr, 1H); 3.2 (m, 3H); 2.8 (dd, 1H); 2.1 (s, 3H); 1.75 (s, 3H) ppm.

The following compounds are prepared analogously as described for Example 20:

| Ex.-No. | Starting material | Structure | Analytical data |
|---|---|---|---|
| 52 | Example 2A; 4-cyano-benzaldehyde; Example 61A | *(structure: 4-cyanophenyl dihydropyridinone with N-[2-(tert-butyldimethylsilyloxy)ethyl]carboxamide and 3-trifluoromethylphenyl N-substituent)* | LC-MS (method 8): $R_t$ = 4.08 min. MS (EI): m/z = 583 [M + H]$^+$ |
| 53 | Example 2A; Example 52A; N-ethyl-malonamic acid ethyl ester | *(structure: 6-cyanopyridin-3-yl dihydropyridinone with N-ethylcarboxamide and 3-trifluoromethylphenyl N-substituent)* | LC-MS (method 8): $R_t$ = 3.18 min. MS (EI): m/z = 454 [M + H]$^+$ |
| 54 | Example 2A; 4-nitro-benzaldehyde; N-ethyl-malonamic acid ethyl ester | *(structure: 4-nitrophenyl dihydropyridinone with N-ethylcarboxamide and 3-trifluoromethylphenyl N-substituent)* | LC-MS (method 8): $R_t$ = 3.40 min. MS (EI): m/z = 473 [M + H]$^+$ |

-continued

| Ex.-No. | Starting material | Structure | Analytical data |
|---|---|---|---|
| 55 | Example 2A; 4-nitro-benzaldehyde; malonamic acid ethyl ester | (structure) | LC-MS (method 8): $R_t$ = 3.22 min. MS (EI): m/z = 445 $[M + H]^+$ |
| 56 | Example 63A; 4-cyano-benzaldehyde; N-ethyl-malonamic acid ethyl ester | (structure) | LC-MS (method 8): $R_t$ = 3.33 min. MS (EI): m/z = 399 $[M + H]^+$ |
| 57 | Example 63A; 4-cyano-benzaldehyde; malonamic acid ethyl ester | (structure) | LC-MS (method 8): $R_t$ = 3.13 min. MS (EI): m/z = 371 $[M + H]^+$ |

-continued
| Ex.-No. | Starting material | Structure | Analytical data |
|---|---|---|---|
| 58 | Example 64A; 4-cyano-benzaldehyde; N-ethyl-malonamic acid ethyl ester | 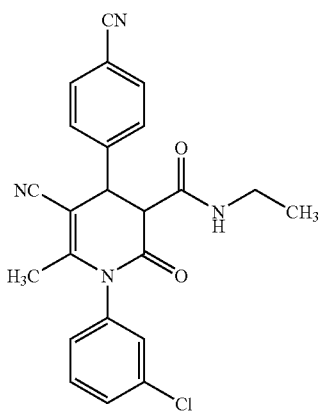 | LC-MS (method 8): $R_t$ = 3.38 min. MS (EI): m/z = 419 $[M + H]^+$ |
| 59 | Example 64A; 4-cyano-benzaldehyde; malonamic acid ethyl ester | 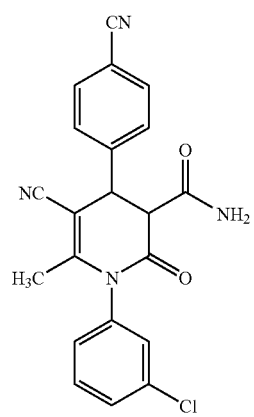 | LC-MS (method 8): $R_t$ = 3.17 min. MS (EI): m/z = 391 $[M + H]^+$ |
| 60 | Example 2A; 4-cyano-benzaldehyde; Example 55A | 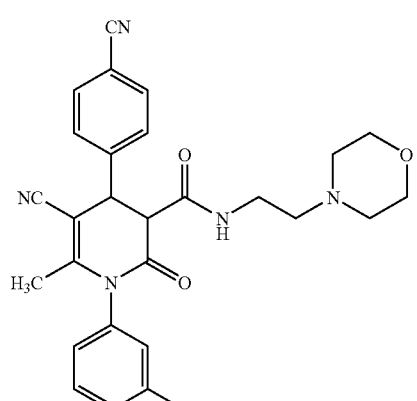 | HPLC (method 5): $R_t$ = 4.20 min. MS (EI): m/z = 538 $[M + H]^+$ |

-continued

| Ex.-No. | Starting material | Structure | Analytical data |
|---|---|---|---|
| 61 | Example 2A; 4-cyano-benzaldehyde; Example 56A | 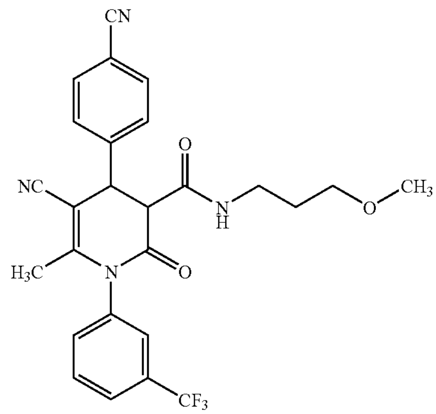 | HPLC (method 5): $R_t$ = 4.49 min. MS (EI): m/z = 497 [M + H]$^+$ |
| 62 | Example 2A; 4-cyano-benzaldehyde; Example 57A | 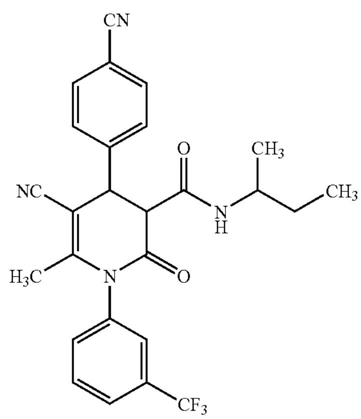 | LC-MS (method 8): $R_t$ = 3.63/3.65 min. MS (EI): m/z = 481 [M + H]$^+$ |
| 63 | Example 2A; 4-cyano-benzaldehyde; Example 58A | 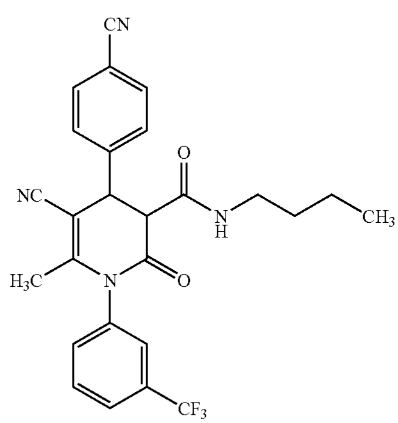 | LC-MS (method 8): $R_t$ = 3.80 min. MS (EI): m/z = 481 [M + H]$^+$ |

-continued

| Ex.-No. | Starting material | Structure | Analytical data |
|---|---|---|---|
| 64 | Example 2A; 4-cyano-benzaldehyde; Example 59A | 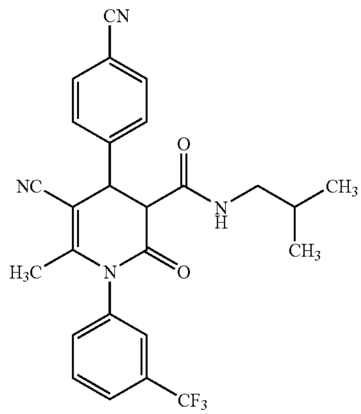 | LC-MS (method 7): $R_t$ = 3.80 min. MS (EI): m/z = 481 $[M + H]^+$ |
| 65 | Example 2A; 4-cyano-benzaldehyde; Example 60A | 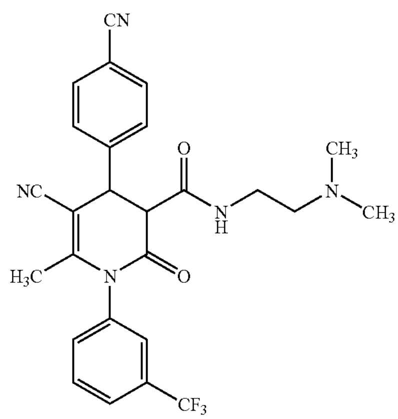 | LC-MS (method 8): $R_t$ = 2.46 min. MS (EI): m/z = 496 $[M + H]^+$ |
| 66 | Example 2A; 4-cyano-benzaldehyde; Example 62A | 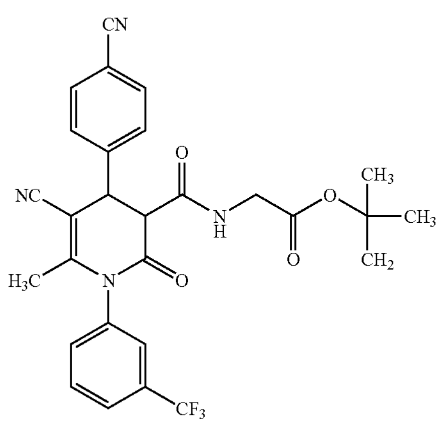 | LC-MS (method 5): $R_t$ = 4.89 min. MS (ESI): m/z = 539 $[M + H]^+$ |

Example 67

{[5-Cyano-4-(4-cyanophenyl)-6-methyl-2-oxo-1-[3-(trifluoromethyl)phenyl]-1,2,3,4-tetrahydropyridine-3-carbonyl]amino}acetic acid

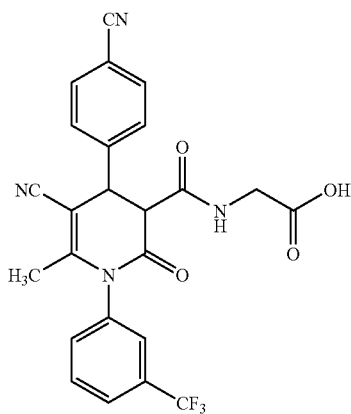

Example 66 (329 mg, 0.61 mmol) is dissolved in trifluoroacetic acid (3 ml) and stirred at room temperature for 30 min. The solvent is removed in vacuo and the residue is purified by column chromatography (silica, eluent dichloromethane/methanol 50:1).

Yield: 158 mg (54% of th.) $^1$H-NMR (200 MHz, DMSO-$d_6$): δ=1.9 (s, 3H); 3.8 (m, 2H); 4.0 (d, 1H); 4.5 (d, 1H); 7.6 (m, 3H); 7.7 (m, 2H); 7.9 (m, 3H); 8.7 (t, 1H) ppm.

Example 68

5-Cyano-4-(4-cyanophenyl)-6-methyl-2-oxo-1-[3-(trifluoromethyl)phenyl]-1,2,3,4-tetrahydropyridine-3-carboxylic acid (2-hydroxyethyl)amide

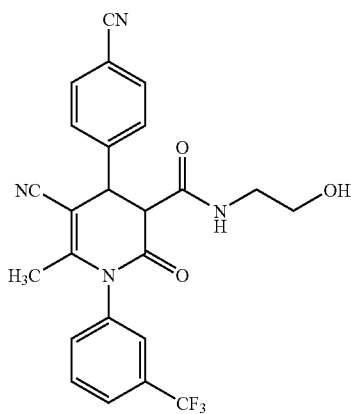

Example 52 (50 mg, 0.09 mmol) is dissolved in tetrahydrofuran (2 ml), 34 mg (0.13 mmol) tetra-n-butylammonium fluoride are added and the mixture is stirred at room temperature for 48 hours. The solvent is removed in vacuo and the residue is purified by preparative HPLC.

Yield: 18 mg (45% of th.) $^1$H-NMR (300 MHz, DMSO-$d_6$): δ=1.9 (s, 3H); 3.1 (m, 2H); 3.3 (m, 2H); 3.9 (d, 1H); 4.5 (d, 1H); 4.6 (t, 1H); 7.6 (m, 31H); 7.8 (m, 2H); 7.9 (m, 3H); 8.3 (t, 1H) ppm.

Example 69

4-(4-Cyanophenyl)-2-methyl-6-oxo-1-[3-(trifluoromethyl)phenyl]-1,4,5,6-tetrahydropyridine-3-carboxylic acid cyclopropylamide

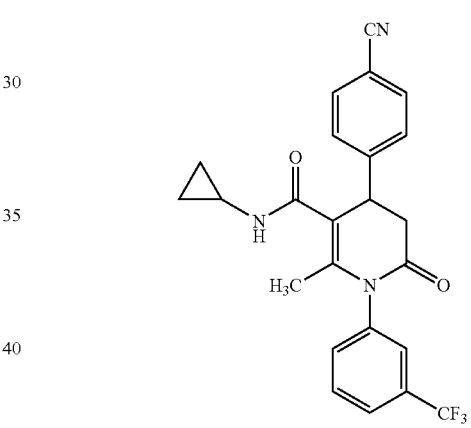

50 mg (0.12 mmol) of Example 47 are dissolved in 2 ml tetrahydrofuran, and 1.5 mg (0.01 mmol) 4-N,N-dimethylaminopyridine, 19 mg (0.15 mmol) N,N-diisopropylethylamine and 78 mg (0.15 mmol) benzotriazol-1-yloxy-tris(pyrrolidino)phosphonium hexafluorophosphate are added. The reaction mixture is stirred at room temperature for 15 minutes, then cyclopropylamine (14 mg, 0.25 mmol) is added. The reaction mixture is stirred at room temperature for 1 hour, then water and ethyl acetate are added. The organic phase is dried over sodium sulfate and evaporated to dryness in vacuo. The residue is further purified by preparative HPLC.

Yield: 43 mg (78% of th.) $^1$H-NMR (400 MHz, DMSO-$d_6$): δ=0.3 (m, 2H); 0.6 (m, 2H); 1.7 (s, 3H); 2.6 (m, 1H); 2.7 (d/d, 1H); 3.2 (d/d, 1H); 4.2 (d/d, 1H); 7.5 (m, 4H); 7.75 (m, 2H); 7.8 (m, 2H); 8.2 (d, 1H) ppm.

The following compounds are prepared analogously as described for Example 69:

| Ex.-No. | Starting material | Structure | Analytical data |
|---|---|---|---|
| 70 | Example 47; 1-benzyl-piperidin-4-ylamine | 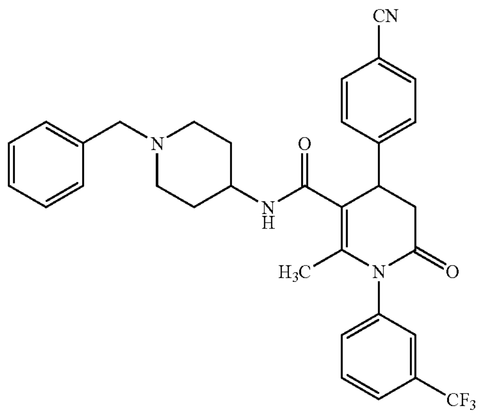 | LC-MS (method 11): $R_t$ = 3.61 min. MS (EI): m/z = 573 [M + H]$^+$ |
| 71 | Example 47; 2-chloro-benzylamine | 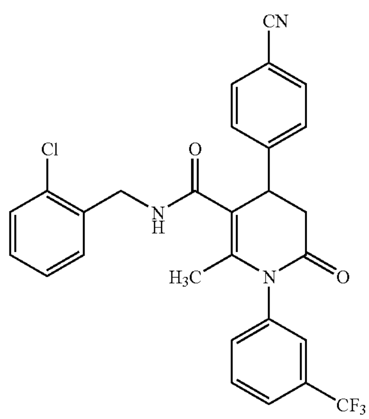 | LC-MS (method 11): $R_t$ = 4.32 min. MS (EI): m/z = 524 [M + H]$^+$ |
| 72 | Example 47; 2-(2-fluoro-phenyl)-ethylamine | 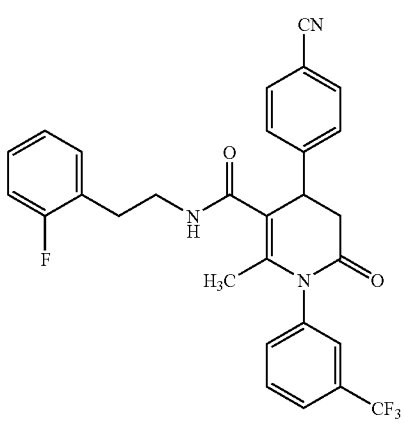 | LC-MS (method 11): $R_t$ = 4.30 min. MS (EI): m/z = 522 [M + H]$^+$ |

| Ex.-No. | Starting material | Structure | Analytical data |
|---|---|---|---|
| 73 | Example 47; 2-fluoro-benzylamine | 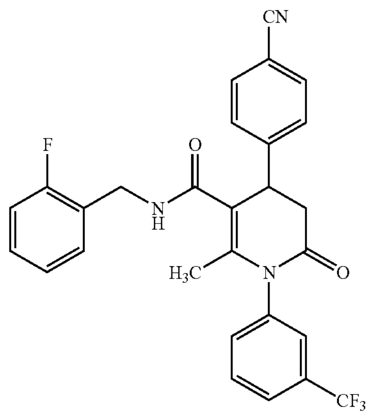 | LC-MS (method 11): $R_t$ = 4.26 min. MS (EI): m/z = 508 $[M + H]^+$ |
| 74 | Example 47; $N^1,N^1$-dimethyl-ethane-1,2-diamine | 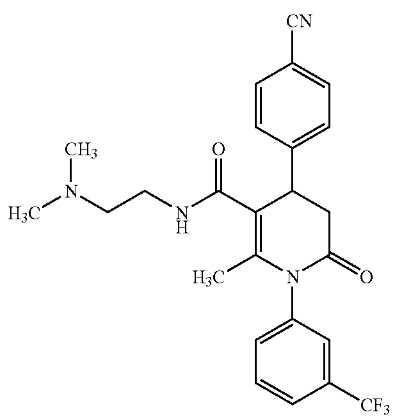 | LC-MS (method 11): $R_t$ = 3.20 min. MS (EI): m/z = 471 $[M + H]^+$ |
| 75 | Example 47; 2-methoxy-ethylamine | 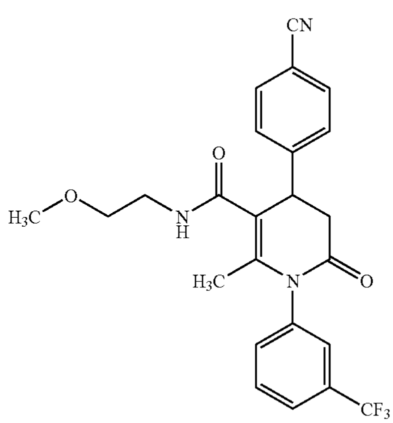 | LC-MS (method 11): $R_t$ = 4.09 min. MS (EI): m/z = 458 $[M + H]^+$ |

-continued

| Ex.-No. | Starting material | Structure | Analytical data |
|---|---|---|---|
| 76 | Example 47; isobutyl-amine | 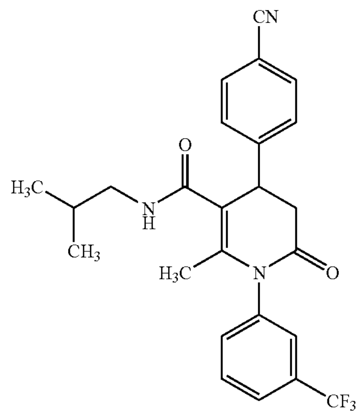 | LC-MS (method 11): $R_t$ = 4.33 min. MS (EI): m/z = 456 $[M + H]^+$ |
| 77 | Example 47; ethylamine (2 M solution in THF) | 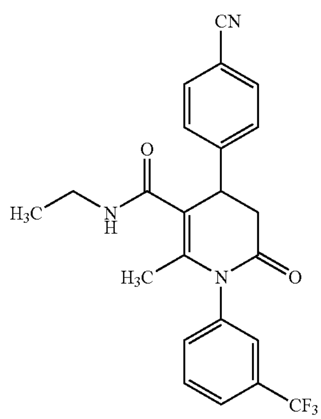 | LC-MS (method 11): $R_t$ = 4.15 min. MS (EI): m/z = 428 $[M + H]^+$ |
| 78 | Example 47; methylamine (2 M solution in THF) | 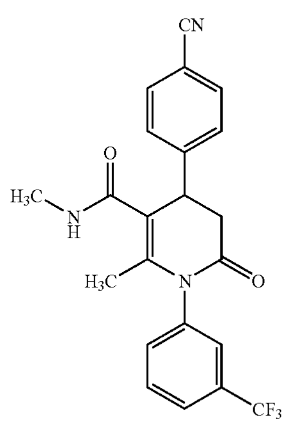 | LC-MS (method 11): $R_t$ = 4.09 min. MS (EI): m/z = 414 $[M + H]^+$ |

-continued

| Ex.-No. | Starting material | Structure | Analytical data |
|---|---|---|---|
| 79 | Example 23; morpholine | *(structure shown: dihydropyridinone with 4-cyanophenyl, 3-trifluoromethylphenyl, and alanine-morpholine amide substituents)* mixture of diastereomers | LC-MS (method 8): $R_t$ = 3.60 min. MS (EI): m/z = 566 [M + H]$^+$ |
| 80 | Example 23; dimethylamine (2 M solution in THF) | *(structure shown: dihydropyridinone with 4-cyanophenyl, 3-trifluoromethylphenyl, and alanine-N,N-dimethylamide substituents)* mixture of diastereomers | LC-MS (method 8): $R_t$ = 3.62 min. MS (EI): m/z = 524 [M + H]$^+$ |
| 81 | Example 23; cyclopropylamine | *(structure shown: dihydropyridinone with 4-cyanophenyl, 3-trifluoromethylphenyl, and alanine-cyclopropylamide substituents)* mixture of diastereomers | LC-MS (method 8): $R_t$ = 3.35/3.38 min. MS (EI): m/z = 536 [M + H]$^+$ |

-continued
| Ex.-No. | Starting material | Structure | Analytical data |
|---|---|---|---|
| 82 | Example 23; 2-methoxy-ethylamine | 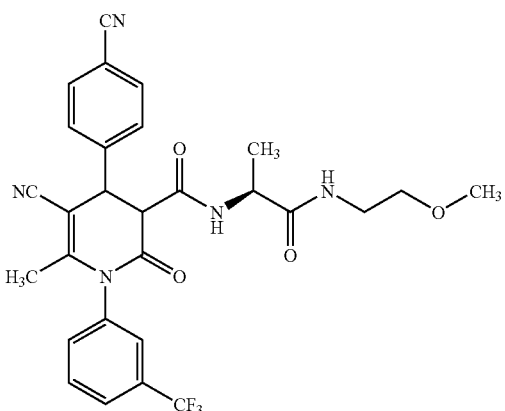<br>mixture of diastereomers | LC-MS (method 8):<br>$R_t$ = 3.30 min.<br>MS (EI): m/z = 554 [M + H]$^+$ |
| 83 | Example 23; methylamine (2 M solution in THF) | 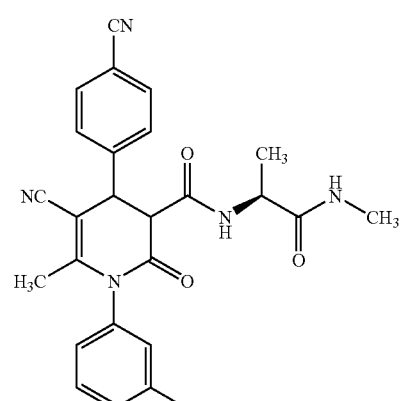<br>mixture of diastereomers | LC-MS (method 8):<br>$R_t$ = 3.24 min.<br>MS (EI): m/z = 510 [M + H]$^+$ |
| 84 | Example 19; morpholine | 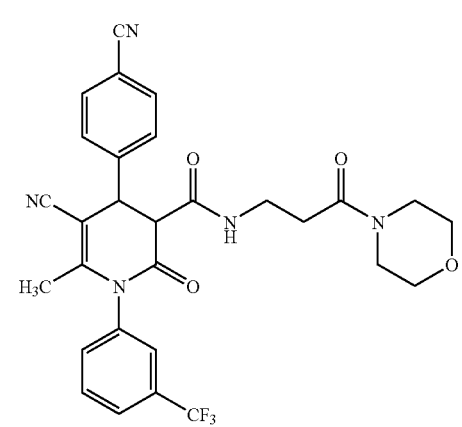 | LC-MS (method 8):<br>$R_t$ = 3.26 min.<br>MS (EI): m/z = 566 [M + H]$^+$ |

| Ex.-No. | Starting material | Structure | Analytical data |
|---|---|---|---|
| 85 | Example 19; dimethyl-amine (2 M solution in THF) | 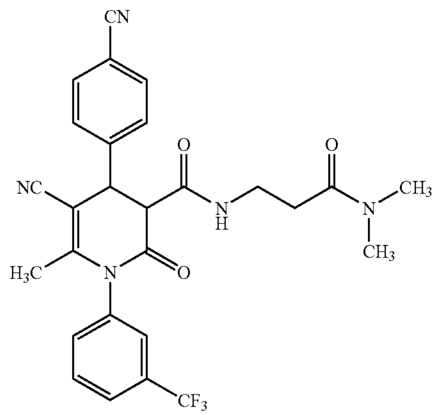 | LC-MS (method 8): $R_t$ = 3.27 min. MS (EI): m/z = 524 $[M + H]^+$ |
| 86 | Example 19; cyclopropyl-amine | 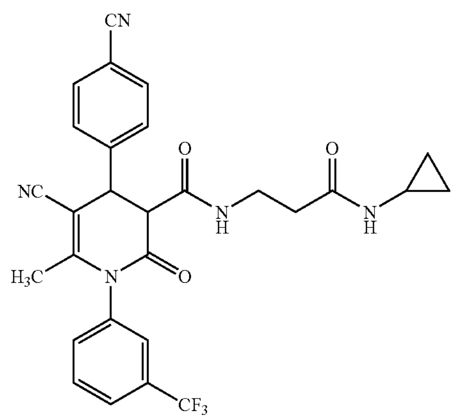 | LC-MS (method 8): $R_t$ = 3.28 min. MS (EI): m/z = 536 $[M + H]^+$ |
| 87 | Example 19; 2-methoxy-ethylamine | 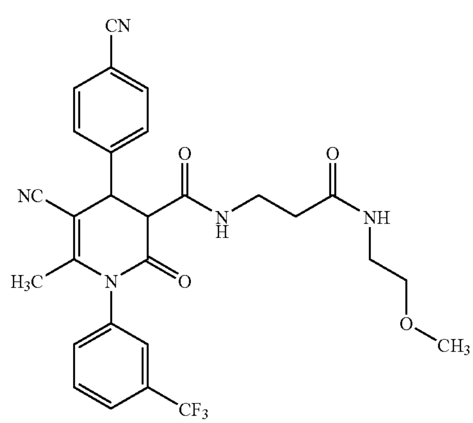 | LC-MS (method 8): $R_t$ = 3.22 min. MS (EI): m/z = 554 $[M + H]^+$ |

| Ex.-No. | Starting material | Structure | Analytical data |
|---|---|---|---|
| 88 | Example 19; methylamine (2 M solution in THF) | 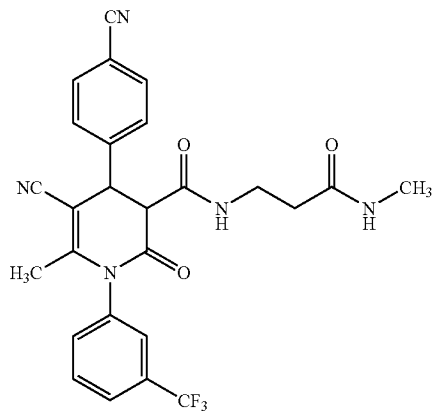 | LC-MS (method 8): $R_t$ = 3.17 min. MS (EI): m/z = 510 [M + H]$^+$ |

Example 89

4-(4-Cyanophenyl)-5-cyclopropanecarbonyl-2-methyl-6-oxo- 1-[3-(trifluoromethyl)-phenyl]-1,4,5,6-tetrahydropyridine-3-carboxylic acid ethyl ester

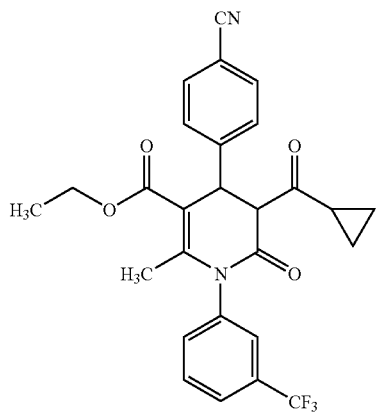

150 mg (0.35 mmol) of Example 14 are dissolved in 5 ml tetrahydrofuran. At −78° C., 389 μl (0.7 mmol) lithiumdiisopropylamide (1.8 M solution in tetrahydrofuran) are added slowly. After stirring at −78° C. for 30 minutes, 55 mg (0.53 mmol) cyclopropylcarbonyl chloride are added. The solution is allowed to warm up to room temperature over night and is then quenched with methanol. After evaporation to dryness in vacuo, the product is further purified by column chromatography (silica, eluent dichloromethane/methanol mixtures).

Yield: 119 mg (68% of th.) LC-MS (method 11): $R_t$=4.32 min. MS (EI): m/z=497 [M+H]$^+$.

The following compounds are prepared analogously as described for Example 89:

| Ex.-No. | Starting material | Structure | Analytical data |
|---|---|---|---|
| 90 | Example 14; 2-methoxy-ethyl chloroformate | 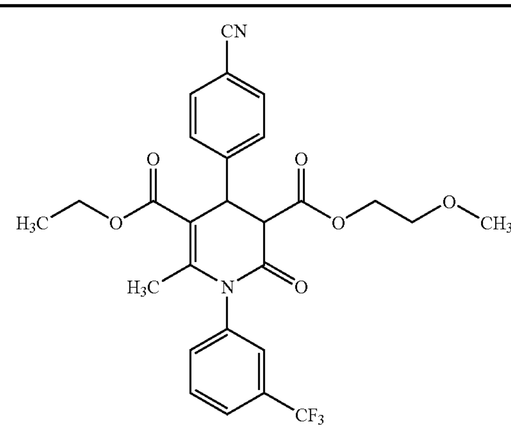 | LC-MS (method 7): $R_t$ = 3.8 min. MS (EI): m/z = 531 [M + H]$^+$ |

-continued

| Ex.-No. | Starting material | Structure | Analytical data |
|---|---|---|---|
| 91 | Example 14; phenyl chloroformate | 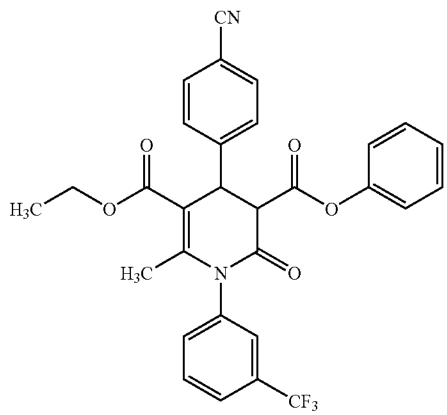 | LC-MS (method 4): $R_t$ = 4.06 min. MS (EI): m/z = 549 $[M + H]^+$ |
| 92 | Example 14; allyl chloroformate | 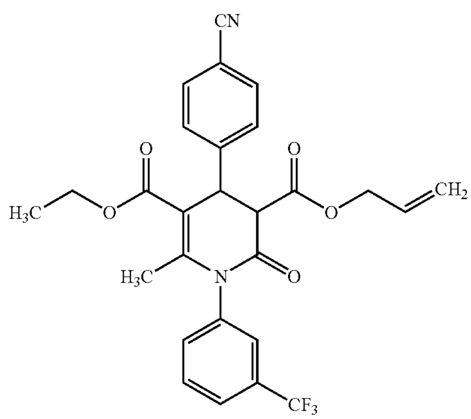 | LC-MS (method 11): $R_t$ = 4.37 min. MS (EI): m/z = 513 $[M + H]^+$ |
| 93 | Example 14; 4-acetyl-piperazine-1-carbonyl chloride | 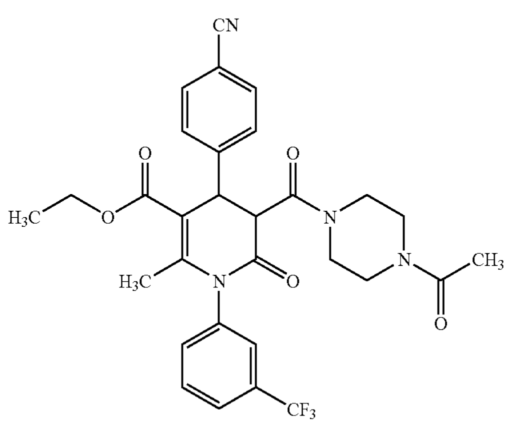 | LC-MS (method 11): $R_t$ = 4.09 min. MS (EI): m/z = 583 $[M + H]^+$ |

-continued

| Ex.-No. | Starting material | Structure | Analytical data |
|---|---|---|---|
| 94 | Example 14; diisopropyl-carbamoyl-chloride | 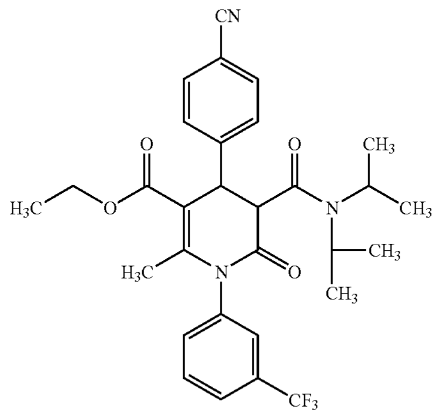 | LC-MS (method 4): $R_t$ = 4.11 min. MS (EI): m/z = 556 $[M + H]^+$ |
| 95 | Example 14; N-methyl-N-phenyl carbamoyl chloride | 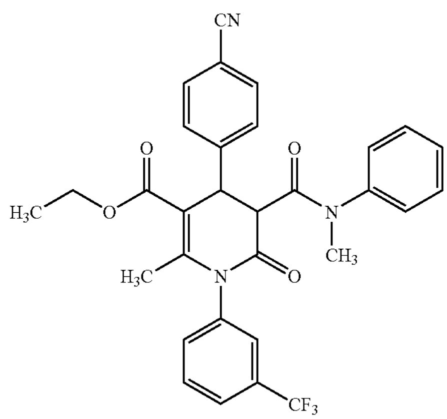 | LC-MS (method 4): $R_t$ = 4.02 min. MS (EI): m/z = 562 $[M + H]^+$ |
| 96 | Example 14; benzoyl chloride | 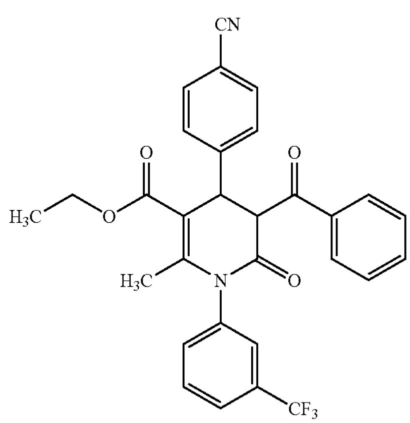 | LC-MS (method 11): $R_t$ = 4.54 min. MS (EI): m/z = 533 $[M + H]^+$ |

| ExNo. | Starting material | Structure | Analytical data |
|---|---|---|---|
| 97 | Example 14; butyryl chloride | 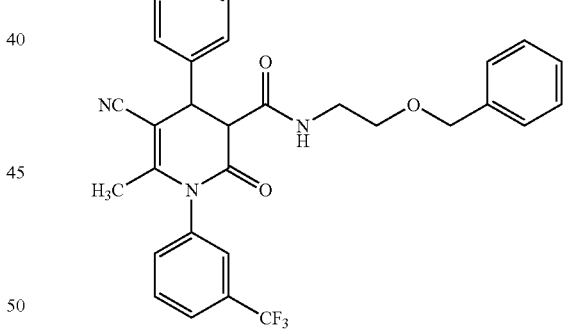 | LC-MS (method 11): $R_t$ = 4.54 min. MS (EI): m/z = 499 $[M + H]^+$ |

Example 98

(−)-5-Cyano-4-(4-cyanophenyl)-6-methyl-2-oxo-1-[3-(trifluoromethyl)phenyl]-1,2,3,4-tetrahydro-3-pyridinecarboxamide

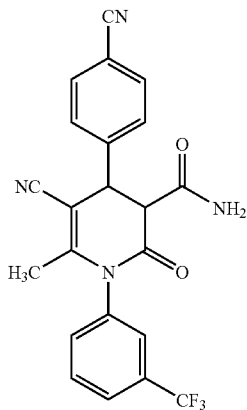

The enantiomers of Example 7 are separated by preparative HPLC on a chiral phase [column KBD 7644 (chiral silica gel selector based on the monomer N-methacryloyl-D-valin-3-pentylamide, cf. EP-A-379 917), eluent: iso-hexane/tetrahydrofuran→tetrahydrofuran→iso-hexane/tetrahydrofuran, temperature 23° C., detection 254 nm].

(−)-Enantiomer:

$^1$H-NMR data: see Example 7

$[\alpha]^{20}$=−171.6° ($\lambda$=589 nm, methanol, c=525 mg/100 ml).

Example 99

N-[2-(Benzyloxy)ethyl]-5-cyano-4-(4-cyanophenyl)-6-methyl-2-oxo-1-[3-(trifluoromethyl)phenyl]-1,2,3,4-tetrahydro-3-pyridinecarboxamide 80 mg (0.17 mmol) of Example 68 are dissolved in 2 ml tetrahydrofuran, and sodium hydride (8 mg, 0.2 mmol, 60% suspension in paraffine) is added. The reaction mixture is stirred for 1 hour, then benzylbromide (29 mg, 0.17 mmol) is added. After further stirring at room temperature for 1 hour, methanol is added and the mixture is purified by preparative HPLC.

Yield: 21 mg (22% of th.) LC-MS (method 8): $R_t$=3.75 min. MS (EI): m/z=559 $[M+H]^+$.

Example 100

2-[({5-Cyano-4-(4-cyanophenyl)-6-methyl-2-oxo-1-[3-(trifluoromethyl)phenyl]-1,2,3,4-tetrahydro-3-pyridinyl}carbonyl)amino]ethyl methanesulfonate

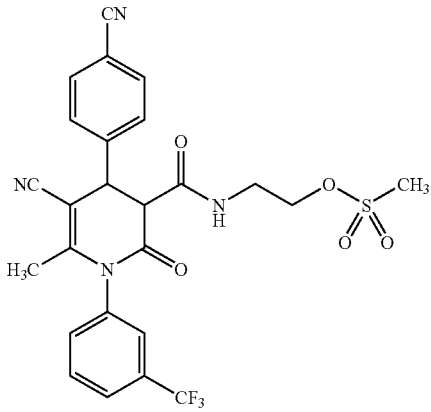

80 mg (0.17 mmol) of Example 68 are dissolved in 2 ml tetrahydrofuran, and sodium hydride (8 mg, 0.2 mmol, 60% suspension in paraffine) is added. The reaction mixture is stirred for 1 hour, then methylsulfonylchloride (20 mg, 0.17 mmol) is added. After further stirring at room temperature for 1 hour, methanol is added and the mixture is purified by preparative HPLC.

Yield: 26 mg (28% of th.) LC-MS (method 8): $R_t$=2.99 min. MS (EI): m/z=547 [M+H]$^+$.

C. Operative Examples Relating to Pharmaceutical Compositions

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate. Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension:

Composition:

1000 mg of the compound of Example 1, 1000 mg of ethanol (96%), 400 mg of Rhodigel (xanthan gum from FMC, Pennsylvania, USA) and 99 g of water. A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

We claim:

1. A compound of the general formula (I)

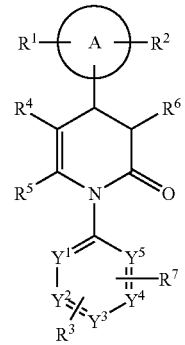

wherein

A represents an aryl or heteroaryl ring, $R^1$, $R^2$ and $R^3$ independently from each other represent hydrogen, halogen, nitro, cyano, trifluoromethyl, $C_1$–$C_6$-alkyl, hydroxy, $C_1$–$C_6$-alkoxy or trifluoromethoxy, wherein $C_1$–$C_6$-alkyl and $C_1$–$C_6$-alkoxy can be further substituted with one to three identical or different radicals selected from the group consisting of hydroxy and $C_1$–$C_4$-alkoxy, $R^4$ represents $C_1$–$C_6$-alkylcarbonyl, $C_1$–$C_6$-alkoxycarbonyl, $C_2$–$C_6$-alkenoxycarbonyl, hydroxycarbonyl, aminocarbonyl, mono- or di-$C_1$–$C_6$-alkylaminocarbonyl, $C_3$–$C_6$-cycloalkylaminocarbonyl, N-(heterocyclyl)-aminocarbonyl or cyano, wherein $C_1$–$C_6$-alkylcarbonyl, $C_1$–$C_6$-alkoxycarbonyl, mono- and di-$C_1$–$C_6$-alkylaminocarbonyl can be substituted with one to three identical or different radicals selected from the group consisting of hydroxy, $C_1$–$C_4$-alkoxy, hydroxycarbonyl, $C_1$–$C_4$-alkoxycarbonyl, amino, mono- and di-$C_1$–$C_4$-alkylamino, aminocarbonyl, mono- and di-$C_1$–$C_4$-alkylaminocarbonyl, $C_1$–$C_4$-alkylcarbonylamino, phenyl, heteroaryl and heterocyclyl, and wherein phenyl can be further substituted with halogen and wherein N-(heterocyclyl)-aminocarbonyl can be further substituted with $C_1$–$C_4$-alkyl or benzyl, $R^5$ represents $C_1$–$C_4$-alkyl, $R^6$ represents hydrogen, cyano, aminocarbonyl, mono- or di-$C_1$–$C_6$-alkylaminocarbonyl, $C_3$–$C_8$-cycloalkylaminocarbonyl, arylaminocarbonyl, N-aryl-N—$C_1$–$C_6$-alkylaminocarbonyl, $C_1$–$C_6$-alkylcarbonyl, $C_3$–$C_8$-cycloalkylcarbonyl, arylcarbonyl, hydroxycarbonyl, $C_1$–$C_6$-alkoxycarbonyl, $C_2$–$C_6$-alkenoxycarbonyl or aryloxycarbonyl, wherein mono- and di-$C_1$–$C_6$-alkylaminocarbonyl, arylaminocarbonyl, $C_1$–$C_6$-alkylcarbonyl and $C_1$–$C_6$-alkoxycarbonyl can be substituted with one to three identical or different radicals selected from the group consisting of halogen, hydroxy, $C_1$–$C_4$-alkoxy, benzyloxy, tri-($C_1$–$C_6$-alkyl)-silyloxy, $C_1$–$C_4$-alkylsulfonyloxy, hydroxycarbonyl, $C_1$–$C_4$-alkoxycarbonyl, amino, mono- and di-$C_1$–$C_4$-alkylamino, aminocarbonyl, mono- and di-$C_1$–$C_4$-alkylaminocarbonyl, $C_3$–$C_6$-cycloalkylaminocarbonyl, heterocyclylcarbonyl, $C_1$–$C_4$-alkylcarbonylamino, phenyl, heteroaryl and heterocyclyl, and wherein mono- and di-$C_1$–$C_4$-alkylaminocarbonyl can be further substituted with hydroxy or $C_1$–$C_4$-alkoxy, or R$^6$ represents a moiety of the formula

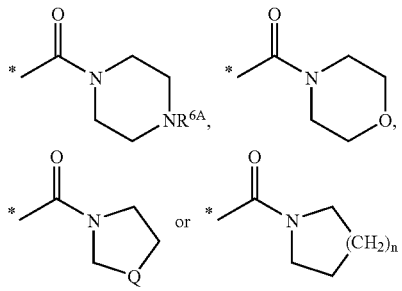

wherein R$^{6A}$ is selected from the group consisting of hydrogen, C$_1$–C$_6$-alkyl and C$_1$–C$_4$-alkylcarbonyl, Q represents O or S, and n represents an integer of 1 or 2, or R$^6$ represents a moiety of the formula

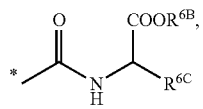

wherein R$^{6B}$ is selected from the group consisting of hydrogen and C$_1$–C$_6$-alkyl, and R$^{6C}$ is an amino acid side chain, R$^7$ represents hydrogen, halogen, nitro, cyano, trifluoromethyl, C$_1$–C$_6$-alkyl, hydroxy, C$_1$–C$_6$-alkoxy or trifluoromethoxy, wherein C$_1$–C$_6$-alkyl and C$_1$–C$_6$-alkoxy can be further substituted with one to three identical or different radicals selected from the group consisting of hydroxy and C$_1$–C$_4$-alkoxy, and Y$^1$, Y$^2$, Y$^3$, Y$^4$ and Y$^5$ independently from each other represent CH or N, wherein the ring contains either 0, 1 or 2 nitrogen atoms, with the understanding that in this context CH also stands for a ring carbon atom, which is substituted with a substituent R$^3$ or R$^7$, or a salt thereof.

2. The compound of general formula (I) according to claim 1, wherein

A represents an aryl or heteroaryl ring,

R$^1$, R$^2$ and R$^3$ independently from each other represent hydrogen, halogen, nitro, cyano, trifluoromethyl, C$_1$–C$_6$-alkyl, hydroxy, C$_1$–C$_6$-alkoxy or trifluoromethoxy, wherein C$_1$–C$_6$-alkyl and C$_1$–C$_6$-alkoxy can be further substituted with one to three identical or different radicals selected from the group consisting of hydroxy and C$_1$–C$_4$-alkoxy, R$^4$ represents C$_1$–C$_6$-alkylcarbonyl, C$_1$–C$_6$-alkoxycarbonyl, hydroxycarbonyl, aminocarbonyl, mono- or di-C$_1$–C$_4$-alkylaminocarbonyl or cyano, wherein C$_1$–C$_6$-alkylcarbonyl, C$_1$–C$_6$-alkoxycarbonyl, mono- and di-C$_1$–C$_4$-alkylaminocarbonyl can be substituted with one to three identical or different radicals selected from the group consisting of hydroxy, C$_1$–C$_4$-alkoxy, hydroxycarbonyl, C$_1$–C$_4$-alkoxycarbonyl, amino, mono- and di-C$_1$–C$_4$-alkylamino, aminocarbonyl, mono- and di-C$_1$–C$_4$-alkylaminocarbonyl, C$_1$–C$_4$-alkylcarbonylamino and heteroaryl, R$^5$ represents C$_1$–C$_4$-alkyl, R$^6$ represents hydrogen, cyano, aminocarbonyl, mono- or di-C$_1$–C$_4$-alkylaminocarbonyl, C$_3$–C$_8$-cycloalkylaminocarbonyl, C$_1$–C$_6$-alkylcarbonyl, hydroxycarbonyl or C$_1$–C$_6$-alkoxycarbonyl, wherein mono- and di-C$_1$–C$_4$-alkylaminocarbonyl, C$_1$–C$_6$-alkylcarbonyl and C$_1$–C$_6$-alkoxycarbonyl can be substituted with one to three identical or different radicals selected from the group consisting of hydroxy, C$_1$–C$_4$-alkoxy, hydroxycarbonyl, C$_1$–C$_4$-alkoxycarbonyl, amino, mono- and di-C$_1$–C$_4$-alkylamino, aminocarbonyl, mono- and di-C$_1$–C$_4$-alkylaminocarbonyl, C$_1$–C$_4$-alkylcarbonylamino, phenyl and heteroaryl, or R$^6$ represents a moiety of the formula

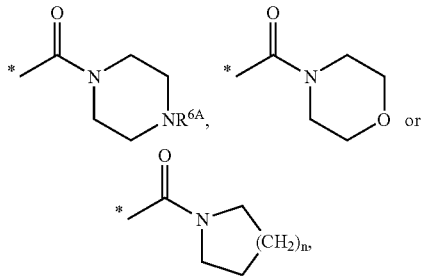

wherein R$^{6A}$ is selected from the group consisting of hydrogen and C$_1$–C$_6$-alkyl, and n represents an integer of 1 or 2, or R$^6$ represents a moiety of the formula

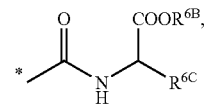

wherein R$^{6B}$ is selected from the group consisting of hydrogen and C$_1$–C$_6$-alkyl, and R$^{6C}$ is an amino acid side chain, R$^7$ represents hydrogen, halogen, nitro, cyano, trifluoromethyl, C$_1$–C$_6$-alkyl, hydroxy, C$_1$–C$_6$-alkoxy or trifluoromethoxy, wherein C$_1$–C$_6$-alkyl and C$_1$–C$_6$-alkoxy can be further substituted with one to three identical or different radicals selected from the group consisting of hydroxy and C$_1$–C$_4$-alkoxy, and Y$^1$, Y$^2$, Y$^3$, Y$^4$ and Y$^5$ independently from each other represent CH or N, wherein the ring contains either 0, 1 or 2 nitrogen atoms, with the understanding that in this context CH also stands for a ring carbon atom, which is substituted with a substituent R$^3$ or R$^7$.

3. The compound of general formula (I) according to claim 1, wherein

A represents an aryl ring,

R$^1$, R$^2$ and R$^3$ independently from each other represent hydrogen, fluoro, chloro, bromo, nitro, cyano, methyl, ethyl, trifluoromethyl or trifluoromethoxy, R$^4$ represents C$_1$–C$_6$-alkylcarbonyl, C$_1$–C$_6$-alkoxycarbonyl or cyano, wherein C$_1$–C$_6$-alkylcarbonyl and C$_1$–C$_6$-alkoxycarbonyl can be substituted with one to two identical or different radicals selected from the group consisting of hydroxy, methoxy, hydroxycarbonyl, methoxycarbonyl, amino, mono- and di-C$_1$–C$_4$-alkylamino, R$^5$ represents methyl or ethyl, R$^6$ represents hydrogen, cyano, aminocarbonyl, mono- or di-C$_1$–C$_4$-alkylaminocarbonyl, hydroxycarbonyl or C$_1$–C$_6$-alkoxycarbonyl, or R⁶ represents a moiety of the formula wherein $R^{6A}$ is selected from the group consisting of hydrogen, methyl and ethyl, and n represents an integer of 1 or 2, or R⁶ represents a moiety of the formula wherein $R^{6B}$ is selected from the group consisting of hydrogen, methyl and ethyl, and $R^{6C}$ is an amino acid side chain, R⁷ represents hydrogen, halogen, nitro, cyano, trifluoromethyl, trifluoromethoxy, methyl or ethyl, and $Y^1$, $Y^2$, $Y^3$, $Y^4$ and $Y^5$ each represent CH, with the understanding that in this context CH also stands for a ring carbon atom, which is substituted with a substituent $R^3$ or $R^7$.

4. The compound of general formula (I) according to claim 1, wherein

A represents a phenyl ring,

R¹ represents hydrogen or methyl,

R² represents cyano, bromo or nitro,

R³ represents hydrogen,

R⁴ represents $C_1$–$C_4$-alkylcarbonyl, $C_1$–$C_4$-alkoxycarbonyl or cyano, wherein $C_1$–$C_4$-alkylcarbonyl and $C_1$–$C_4$-alkoxycarbonyl can be substituted with hydroxycarbonyl or $C_1$–$C_4$-alkoxycarbonyl, R⁵ represents methyl, R⁶ represents hydrogen, cyano, aminocarbonyl, mono- or di-$C_1$–$C_4$-alkylaminocarbonyl, hydroxycarbonyl or $C_1$–$C_6$-alkoxycarbonyl, R⁷ represents trifluoromethyl or nitro, and $Y^1$, $Y^2$, $Y^3$, $Y^4$ and $Y^5$ each represent CH, with the understanding that in this context CH also stands for a ring carbon atom, which is substituted with a substituent $R^3$ or $R^7$.

5. The compound of general formula (I) according to claim 1, wherein A is phenyl.

6. The compound of general formula (I) according to claim 1, wherein R¹ is hydrogen.

7. The compound of general formula (I) according to claim 1, wherein R² is cyano.

8. The compound of general formula (I) according to claim 1, wherein R³ is hydrogen.

9. The compound of general formula (I) according to claim 1, wherein R⁴ is $C_1$–$C_6$-alkylcarbonyl, $C_1$–$C_6$-alkoxycarbonyl or cyano.

10. The compound of general formula (I) according to claim 1, wherein R⁵ is methyl.

11. The compound of general formula (I) according to claim 1, wherein R⁶ is hydrogen, cyano, aminocarbonyl, mono- and di-methyl- or -ethylaminocarbonyl, methoxycarbonyl or ethoxycarbonyl.

12. The compound of general formula (I) according to claim 1, wherein R⁷ is trifluoromethyl or nitro.

13. A compound of general formula (IA)

(IA)

wherein R¹, R³, R⁴ and R⁶ have the meaning indicated in claim 1.

14. A Process for synthesizing the compound of general formula (I) or (IA), respectively, as defined in claims 1 or 13, wherein

[A] a compound of the general formula (II)

(II)

wherein R¹ to R⁷, A and Y¹ to Y⁵ have the meaning indicated in claim 1, is hydrolyzed with water, or

[B] a compound of the general formula (III)

(III)

wherein $R^3$, $R^4$, $R^5$, $R^7$, and $Y^1$ to $Y^5$ have the meaning indicated in claim 1, is reacted with a compound of the general formula (IX)

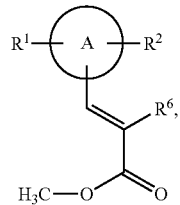

(IX)

wherein $R^1$, $R^2$, $R^6$ and A have the meaning indicated in claim 1,
or

[C] a compound of the general formula (III)

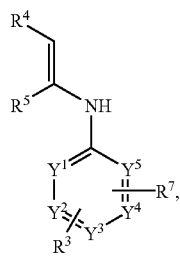

(III)

wherein $R^3$, $R^4$, $R^5$, $R^7$, and $Y^1$ to $Y^5$ have the meaning indicated in claim 1, are reacted with a compound of the general formula (VIII)

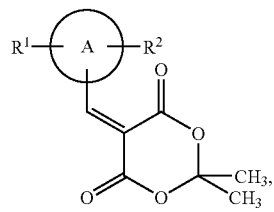

(VIII)

wherein $R^1$ and $R^2$ have the meaning indicated in claim 1.

15. A pharmaceutical composition containing at least one compound of general formula (I) or (IA), as defined in claim 1 or 13, and a pharmacologically acceptable diluent.

16. A process for the preparation of compositions according to claim 15 characterized in that the compounds of general formula (I) or (IA), as defined in claim 1 or 13, together with customary auxiliaries are brought into a suitable application form.

17. A method of treating chronic obstructive pulmonary disease, acute coronary syndrome, acute myocardial infarction or development of heart failure in humans and animals, comprising administering a neutrophil elastase inhibitory amount of at least one compound according to any of claim 1 or 13.

\* \* \* \* \*